US008278284B2

(12) United States Patent
Miyazaki et al.

(10) Patent No.: US 8,278,284 B2
(45) Date of Patent: Oct. 2, 2012

(54) THERAPEUTIC AGENTS FOR DISEASES ASSOCIATED WITH APOPTOTIC DEGENERATION IN OCULAR TISSUE CELLS THAT USE SIV-PEDF VECTORS

(76) Inventors: Masanori Miyazaki, Kasuya-gun (JP); Yoshikazu Yonemitsu, Fukuoka (JP); Yasuhiro Ikeda, Fukuoka (JP); Katsuo Sueishi, Fukuoka (JP); Toshiaki Tabata, Tsukuba (JP); Akihiro Iida, Tsukuba (JP); Yasuji Ueda, Tsukuba-gun (JP); Mamoru Hasegawa, Tsukuba (JP)

( * ) Notice: Subject to any disclaimer, the term of this patent is extended or adjusted under 35 U.S.C. 154(b) by 1031 days.

(21) Appl. No.: 11/884,738

(22) PCT Filed: Feb. 21, 2006

(86) PCT No.: PCT/JP2006/303032

§ 371 (c)(1),
(2), (4) Date: Apr. 15, 2008

(87) PCT Pub. No.: WO2006/090689

PCT Pub. Date: Aug. 31, 2006

(65) Prior Publication Data

US 2009/0233988 A1 Sep. 17, 2009

(30) Foreign Application Priority Data

Feb. 23, 2005 (JP) ................................ 2005-047951

(51) Int. Cl.
*A61K 48/00* (2006.01)
*A01N 63/00* (2006.01)
*C12P 19/34* (2006.01)

(52) U.S. Cl. ..................... 514/44 R; 424/93.1; 435/91.1

(58) Field of Classification Search ........................ None
See application file for complete search history.

(56) References Cited

U.S. PATENT DOCUMENTS

| | | | |
|---|---|---|---|
| 6,979,568 | B1 | 12/2005 | Nakajima et al. |
| 2004/0234948 | A1 | 11/2004 | Hanazono et al. |
| 2005/0191747 | A1 | 9/2005 | Luo et al. |

FOREIGN PATENT DOCUMENTS

| | | |
|---|---|---|
| EP | 1 398 041 | 3/2004 |
| WO | WO 00/78987 | 12/2000 |
| WO | WO 02/101057 | 12/2002 |

OTHER PUBLICATIONS

Streck et al., 2005, J. Pediatric Surg., vol. 40, pp. 236-243.*
Miyazaki et al., 2003, Gene Therapy, vol. 10, pp. 1503-1511.*
Nakajima et al., 2000, Human Gene Therapy, vol. 11, pp. 1863-1874.*
Sirven et al., 2000, Blood, vol. 96(13), pp. 4103-4110.*
1996, Giavedoni et al., J. Virology, vol. 70(4), pp. 2247-2251.*
Schwartz, "Visual Perception: A Clinical Orientation (Fourth Edition)," McGraw Hill Professional, p. 8 (2009).
Miyazaki et al., "Saru Yurai Lentivirus (SIV) Vector o Mochiita Shikiso Johi Yurai Inshi (PEDF) Idenshi Donyu ni yoru RCS Rat no Shisaibo Hensei Yokusei Koka," Momaku Myakurakumaku • Shishinkei Ishukusho ni Kansuru Kenkyu Heisei 14 Nendo Sokatsu • Buntan Kenkyu Hokokusho, 2003, pp. 143 to 146.
International Search Report for PCT/JP2006/303032, mailed May 16, 2006.
Barry et al., "Lentivirus Vectors Encoding Both Central Polypurine Tract and Posttranscriptional Regulatory Element Provide Enhanced Transduction and Transgene Expression," *Hum. Gene Ther.* 12(9):1103-1108 (2001).
Dawson et al., "Pigment Epithelium-Derived Factor: A Potent Inhibitor of Angiogenesis," *Science* 285(5425):245-248 (1999).
Dull et al., "A Third-Generation Lentivirus Vector with a Conditional Packaging System," *J. Virol.* 72(11):8463-8471 (1998).
Ikeda et al., "Simian Immunodeficiency Virus-Based Lentivirus Vector for Retinal Gene Transfer: A Preclinical Safety Study in Adult Rats," *Gene Ther.* 10(14):1161-1169 (2003).
Kim et al., "Minimal Requirement for a Lentivirus Vector Based on Human Immunodeficiency Virus Type 1," *J. Virol.* 72(1):811-816 (1998).
Maik-Rachline et al., "Extracellular Phosphorylation Converts Pigment Epithelium-Derived Factor from a Neurotrophic to an Antiangiogenic Factor," *Blood* 105(2):670-678 (2005).
Miyazaki et al., "Simian Lentiviral Vector-Mediated Retinal Gene Transfer of Pigment Epithelium-Derived Factor Protects Retinal Degeneration and Electrical Defect in Royal College of Surgeons Rats," *Gene Ther.* 10(17):1503-1511 (2003).
Nakajima et al., "Development of Novel Simian Immunodeficiency Virus Vectors Carrying a Dual Gene Expression System," *Hum. Gene Ther.* 11(13):1863-1874 (2000).
Ogata et, al., "Pigment Epithelium Derived Factor as a Neuroprotective Agent Against Ischemic Retinal Injury," *Curr. Eye Res.* 22(4):245-252 (2001). Takita et al., "Retinal Neuroprotection Against Ischemic Injury Mediated by Intraocular Gene Transfer of Pigment Epithelium-Derived Factor," *Invest. Ophthalmol. Vis. Sci.* 44(10):4497-4504 (2003).
Tombran-Tink et al., "PEDF: A Pigment Epithelium-Derived Factor with Potent Neuronal Differentiative Activity," *Exp. Eye Res.* 53(3):411-414 (1991).
Volpert et al., "Inducer-Stimulated Fas Targets Activated Endothelium for Destruction by Anti-Angiogenic Thrombospondin-1 and Pigment Epithelium-Derived Factor," *Nat. Med.* 8(4):349-357 (2002).
Yabe et, al., "$NF_{\kappa}B$ Activation is Required for the Neuroprotective Effects of Pigment Epithelium-Derived Factor (PEDF) on Cerebellar Granule Neurons," *J. Biol. Chem.* 276(46):43313-43319 (2001).

(Continued)

*Primary Examiner* — Peter Paras, Jr.
*Assistant Examiner* — David A Montanari
(74) *Attorney, Agent, or Firm* — Clark & Elbing LLP

(57) ABSTRACT

The present invention provides novel methods for treating diseases associated with apoptotic degeneration in ocular tissue cells by effective administration of pigment epithelium derived factor (PEDF). The present inventors studied PEDF as a means to prevent ganglion cell death, the final pathology of glaucoma. The present invention is particularly focused on SIV vectors for effective methods for delivering PEDF, and constructed an SIV-PEDF vector. When the SIV-PEDF vector was administered subretinally to an ischemia reperfusion model and NMDA-induced model, a significant suppression effect on ganglion cell death was observed. The present inventors therefore discovered that the SIV-PEDF vector is an effective pharmaceutical agent for treating diseases associated with apoptotic degeneration in ocular tissue cells, such as glaucoma.

7 Claims, 13 Drawing Sheets

OTHER PUBLICATIONS

Yabe et, al., "Treatment of Cerebellar Granule Cell Neurons with the Neurotrophic Factor Pigment Epithelium-Derived Factor In Vitro Enhances Expression of other Neurotrophic Factors as well as Cytokines and Chemokines," *J. Neurosci. Res.* 77(5):642-652 (2004).

International Search report for PCT/JP2006/303032 mailed May 16, 2006.

Hasegawa, "Health, Labour and Science Research Grants for Research on HIV/AIDS, Comprehensive Research Report," DNAVEC Research, Inc.

English translation of Hasegawa, "Health, Labour and Science Research Grants for Research on HIV/AIDS, Comprehensive Research Report," DNAVEC Research, Inc.

Semkova et al., "Gene Transfer of Retinal Ganglion Cells (RGCs) by High-Capacity Adenovirus (HC-Ad) Vector Expressing Pigment Epithelium-Derived Factor (PEDF) Protects them Against Neurodegeneration In Vivo," *Invest. Ophthalmol. Vic. Sci.* 44: E-Abstract 148 (2003).

Goreham-Voss et al., "Optimizing Non-Primate Lentiviral Vectors for Gene Transfer of CFTR to Airway Epithelia," *Mol. Ther.* 13(Supplement 1):S313, Abstract 808 (2006).

* cited by examiner (a)

| | MOI | | | |
|---|---|---|---|---|
| | 0.3 | 1.5 | 7.5 | 15.0 |
| cPPT(−),WPRE(−) | 1.2 | 1.5 | 3.3 | 4.8 |
| cPPT(+),WPRE(−) | 1.7 | 3.6 | 11.1 | 17.9 |
| cPPT(−),WPRE(+) | 2.2 | 3.5 | 7.5 | 8.4 |
| cPPT(+),WPRE(+) | 3.4 | 12.2 | 31.9 | 48.8 |

(b)

| | cPPT(−) | cPPT(+) |
|---|---|---|
| WPRE(−) | 6.1 | 6.8 |
| WPRE(+) | 10.5 | 19.6 |

FIG. 7

THERAPEUTIC AGENTS FOR DISEASES ASSOCIATED WITH APOPTOTIC DEGENERATION IN OCULAR TISSUE CELLS THAT USE SIV-PEDF VECTORS

CROSS-REFERENCE TO RELATED APPLICATIONS

This application is the U.S. National Stage of International Application PCT/JP2006/303032, filed Feb. 21, 2006, which claims the benefit of Japanese Application Serial No. JP 2005-047951, filed Feb. 23, 2005.

TECHNICAL FIELD

The present invention relates to methods for treating glaucoma using a lentiviral vector carrying a neurotrophic factor.

BACKGROUND ART

Glaucoma involves at least one characteristic change in the optic nerve heads or visual field, and is characterized by both functional and structural abnormalities of eyes. Usually, the optic nerve injury can be improved or prevented from progressing by sufficiently decreasing the ocular pressure. However, glaucoma can lead to blindness if not appropriately treated. Blindness due to glaucoma is the second most common cause of acquired blindness in Japan.

Glaucoma can be classified into primary glaucoma, secondary glaucoma, and developmental glaucoma. Primary glaucoma can be further categorized into primary open-angle glaucoma (broadly defined), primary angle-closure glaucoma, and mixed glaucoma. Broadly-defined primary open-angle glaucoma includes primary open-angle glaucoma (narrowly defined) and normal tension glaucoma. Normal tension glaucoma is a disease in which the optic nerve is damaged, although the intraocular pressure is within the normal range (21 mmHg or less, 15.5 mmHg on average). Approximately 5.8% of people who are 40 years old or older are said to be affected by glaucoma. Since, according to the statistics in 2000, the 40 and older population in Japan is approximately 65 million, the number of people affected by glaucoma who are 40 years old or older is estimated to be over 3.7 million.

"Intraocular pressure" is an important risk factor in the occurrence and progression of optic nerve injury associated with glaucoma. Conventionally, decreasing intraocular pressure has been recognized as the only reliable therapeutic method. Therapeutic methods for decreasing the intraocular pressure generally involve eye drops (β-blockers, prostaglandin-related agents, carbonic anhydrase inhibitors, and such), oral or injection agents (carbonic anhydrase inhibitors, or hypertonic agents), and surgery (laser surgery, or invasive surgery).

However, factors other than "intraocular pressure", such as impaired microcirculation and fragility of the optic nerves, have also been suggested to be involved in glaucoma, and the limit of intraocular pressure-lowering therapies has been pointed out. Therefore, there is a need to develop therapeutic methods for glaucoma apart from intraocular pressure-lowering therapies. One such method that has attracted attention involves inhibiting retinal ganglion cell death (apoptosis), the final pathology of glaucoma; namely, retinal ganglion cell protection therapy.

Meanwhile, neurotrophic factors promote growth and differentiation of undifferentiated neuroblasts, as well as the survival and maintenance of the function of mature neurons. Pigment epithelium-derived factor (PEDF) is one of the neurotrophic factors. To date, two biological activities for PEDF have been reported: neurodifferentiation/neuroprotection activity and antiangiogenic activity. PEDF was originally purified in 1989 from the culture supernatant of human embryonic retinal pigment epithelial cells as a factor that promotes neurodifferentiation of human Y-79 retinoblastoma cells (Non-Patent Document 1). It has since been reported to have effects of inducing differentiation and suppressing injury-induced neuronal apoptosis of various nerve cells, in both in vitro and in vivo systems. The underlying mechanisms have been examined using cultured immature cerebellar granule cells. It has been reported that activation of the transcription factor, NFκB, is involved in these mechanisms and that the expression of the anti-apoptotic genes, Bcl-2 and Bcl-x, and the neurotrophic factors, NGF and BDNF, is also induced (Non-Patent Document 2). Meanwhile, in a microarray study for cultured immature cerebellar granule cells, it has been reported that PEDF addition induces the expression of various neurotrophic factors (NGF, neurotrophin-3, and GDNF), though neurotrophic factors induced in the analysis using neutralizing antibodies do not influence the neuroprotective effect of PEDF (Non-Patent Document 3), which suggests that the protective effect is a direct action of PEDF. Furthermore, in 1999, it was reported that PEDF suppressed FGF-2-induced migration of vascular endothelial cells in a concentration-dependent manner in in vitro systems. This effect was higher than angiostatin or endostatin. In addition, PEDF was also shown to significantly suppress FGF2-induced corneal neovascularization in vivo (Non-Patent Document 4). Thereafter, a number of reports have been made on the phenomena of suppressing various angiogenesis models and tumor angiogenesis. Their mechanisms have not been elucidated in detail, but the following possibilities are contemplated: (1) since PEDF induces the expression of FasL in vascular endothelial cells, and Fas is highly expressed in vascular endothelial cells that are in the process of neogenesis, Fas/FasL-mediated apoptosis of endothelial cells may suppress angiogenesis (Non-Patent Document 5); (2) extracellular phosphorylation may be involved (Non-Patent Document 6); and (3) binding with extracellular substrates may be involved.

Based on the apoptosis-suppressing effects described above, methods for protecting ganglion cells using neurotrophic factors have been examined. To date, two studies of PEDF gene therapy using retinal ischemia reperfusion models have been reported. In these studies, the cell injury-suppressing effect of PEDF was examined using "retinal ischemia reperfusion model" rats, whose ganglion cells are damaged and have undergone apoptotic death as in glaucoma. In the above-mentioned studies, a PEDF protein (Non-Patent Document 7) or an adenoviral vector carrying PEDF (Non-Patent Document 8) was administered to the vitreous body of the animals, and retinal ganglion cell injury due to ischemia reperfusion was suppressed histologically.

However, neurotrophic factors have a large molecular weight. It is difficult to continuously deliver large molecular weight proteins to the retina using the current drug delivery systems. Furthermore, since genes introduced by adenoviral vectors exist as episomes in nuclei and are thus not incorporated into chromosomal DNA, transgenes that do not have autonomous replication ability are diluted as the cells grow, and expression of the transgenes becomes transient. Considering that glaucoma is a chronic disease, administration methods that are expected to provide only transient effects cannot be considered as suitable therapeutic methods for glaucoma. On the other hand, retroviral vectors may generally enable long-term expression of genes by being stably incorporated into the chromosomes of dividing cells; however, there is so far no known study of glaucoma therapy that uses retroviral vectors into which PEDF has been inserted.

[Patent Document 1] International Application No. PCT/JP2002/005225; WO2002/101057

[Patent Document 2] International Application No. PCT/JP00/03955; WO00/078987

[Non-Patent Document 1] Tombran-Tink J, Chader G G; Johnson L V. PEDF: a pigment epithelium-derived factor with potent neuronal differentiative activity. Exp Eye Res. 1991 September; 53(3):411-4.

[Non-Patent Document 2] Yabe T, Wilson D, Schwartz J P. NFkappaB activation is required for the neuroprotective effects of pigment epithelium-derived factor (PEDF) on cerebellar granule neurons. J Biol. Chem. 2001 November 16; 276(46):43313-9.

[Non-Patent Document 3] Yabe T, Herbert J T, Takanohashi A, Schwartz J P. Treatment of cerebellar granule cell neurons with the neurotrophic factor pigment epithelium-derived factor in vitro enhances expression of other neurotrophic factors as well as cytokines and chemokines. J Neurosci Res. 2004 September 1; 77(5):642-52.

[Non-Patent Document 4] Dawson D W, Volpert O V, Gillis P, Crawford S E, Xu H, Benedict W, Bouck N P. Pigment epithelium-derived factor: a potent inhibitor of angiogenesis. Science. 1999 July 9; 285(5425):245-8.

[Non-Patent Document 5] Volpert O V, Zaichuk T, Zhou W, Reiher F, Ferguson T A, Stuart P M, Amin M, Bouck N P. Inducer-stimulated Fas targets activated endothelium for destruction by anti-angiogenic thrombospondin-1 and pigment epithelium-derived factor. Nat. Med. 2002 April; 8(4):349-57.

[Non-Patent Document 6] Maik-Rachline C; Shaltiel S, Seger R. Extracellular phosphorylation converts pigment epithelium-derived factor from a neurotrophic to an antiangiogenic factor. Blood. 2005 January 15; 105(2):670-8. Epub 2004 Sep. 16.

[Non-Patent Document 7] Ogata N, Wang L, Jo N, Tombran-Tink J, Takahashi K, Mrazek D, Matsumura M. Pigment epithelium derived factor as a neuroprotective agent against ischemic retinal injury. Curr Eye Res. 2001 April; 22(4):245-52.

[Non-Patent Document 8] Takita H, Yoneya S, Gehlbach P L, Duh E J, Wei L L, Mori K. Retinal neuroprotection against ischemic injury mediated by intraocular gene transfer of pigment epithelium-derived factor. Invest Opthalmol Vis Sci. 2003 October; 44(10):4497-504.

[Non-Patent Document 9] Miyazaki M, Ikeda Y, Yonemitsu Y, Goto Y, Sakamoto T, Tabata T, Ueda Y, Hasegawa M, Tobimatsu S, Ishibashi T, Sueishi K. Simian lentiviral vector-mediated retinal gene transfer of pigment epithelium-derived factor protects retinal degeneration and electrical defect in Royal College of Surgeons rats. Gene Ther. 2003 August; 10(17):1503-11.

DISCLOSURE OF THE INVENTION

Problems to be Solved by the Invention

The present invention was achieved in view of the above circumstances. An objective of the present invention is to construct pharmaceutical agents for treating diseases associated with apoptotic degeneration in ocular tissue cells, such as glaucoma, by effectively delivering PEDF.

Means for Solving the Problems

Upon dedicated research to solve the above-mentioned objective, the present inventors focused on vectors of monkey-derived lentiviruses, which are retroviral vectors, and particularly on vectors of the simian immunodeficiency virus (SIV), as a means for administering PEDF. The present inventors considered that a gene transfer method in which an SIV vector is subretinally administered allows a therapeutic gene to be stably expressed for a long period in the retina, and this can exceed the limits of the current drug delivery systems. More specifically, gene transfer using an SIV vector is expected to (i) not be affected by the blood-retinal barrier (BRB), (ii) be able to maintain a therapeutically-effective concentration and reduce side-effects, and (iii) be able to reduce the cost incurred by frequent administration of therapeutic preparations. Furthermore, the present inventors have administered an SIV vector carrying PEDF to retinitis pigmentosa model animals and elucidated a significant suppressive effect against the death (apoptosis) of visual cells (Non-Patent Document 9). Accordingly, administration of SIV vectors carrying neurotrophic factors may become an effective neuroprotective therapy against retinal ganglion cell death associated with glaucoma.

To examine the applicability of an SIV vector carrying PEDF (hereinafter referred to as "SIV-PEDF vector") to glaucoma therapy, the present inventors used an improved SIV vector. The improved SIV vector has been modified to increase the safety and performance of conventional SIV vectors. The first modification, directed at increasing the efficiency of gene transfer and expression, involved the introduction of the central polypurine tract (cPPT) sequence and the woodchuck hepatitis virus posttranscriptional regulatory element (WPRE) sequence into a gene transfer vector for producing the SIV vector. The second modification, directed at increasing the safety, involved the removal of the auxiliary factors (vif, vpr, and tat) from a packaging vector and the transfer of the rev sequence to another vector.

The present inventors examined the application of the above-mentioned improved SIV-PEDF vector to glaucoma using ischemia reperfusion model animals and NMDA-induced model animals. Because it is difficult to cause small animals to develop glaucoma in a strict sense, the above models, in which ganglion cells typically injured by glaucoma are artificially injured, are usually used in the study of glaucoma. In the ischemia reperfusion models, the ganglia are suddenly injured by increasing the ocular pressure to produce an ischemic condition and performing reperfusion. In the NMDA-induced models, only the ganglion cells are selectively injured by administered NMDA. Studies were carried out as follows. The SIV-PEDF vector was administered subretinally to the animals (rats), and then ganglion cells were injured by ischemia reperfusion or NMDA. Thereafter, 4',6-diamidino-2-phenylindole (DAPI) was injected into both superior colliculi to label the ganglion cells, and the number of labeled ganglion cells was measured. As a result, it was observed that the decrease in the number of ganglion cells was significantly suppressed in the SIV-PEDF vector-administered group for both models. From these results, it was demonstrated for the first time that the SIV-PEDF vector can effectively protect ganglion cells and is therefore an effective therapeutic agent for glaucoma. Furthermore, the SIV-PEDF vector of the present invention may be effective for other ophthalmic diseases associated with apoptotic degeneration as in glaucoma. Thus, the present invention relates to treatment of diseases associated with apoptotic degeneration in ocular tissue cells using an SIV-PEDF vector, and more specifically, provides the following inventions:

(1) a pharmaceutical agent for treating a disease associated with apoptotic degeneration in ocular tissue cells, which comprises a recombinant simian immunodeficiency virus vector carrying a pigment epithelium derived factor (PEDF) gene, and a pharmaceutically acceptable vehicle;

(2) the pharmaceutical agent of (1), wherein the simian immunodeficiency virus vector comprises a cPPT sequence and/or a WPRE sequence;

(3) the pharmaceutical agent of (1) or (2), wherein the simian immunodeficiency virus vector is pseudotyped with VSV-G;

(4) the pharmaceutical agent of any one of (1) to (3), wherein the simian immunodeficiency virus vector is derived from an agm strain;

(5) the pharmaceutical agent of any one of (1) to (4), wherein the disease associated with apoptotic degeneration in ocular tissue cells is any one of glaucoma, retinitis pigmentosa, retinal detachment, and retinal ischemic disease;

(6) a method for treating a disease associated with apoptotic degeneration in ocular tissue cells, which comprises administering a recombinant simian immunodeficiency virus vector carrying a PEDF gene;

(7) the method of (6), which comprises the step of administering a recombinant simian immunodeficiency virus vector carrying a PEDF gene by subretinal administration, intravitreal administration, or intracameral administration;

(8) a method for producing the pharmaceutical agent of any one of (1) to (5), which uses a gene transfer vector comprising a nucleotide sequence in which a PEDF gene is inserted in the nucleotide sequence of SEQ ID NO: 1;

(9) the method of (8), which uses a gene transfer vector comprising the nucleotide sequence of SEQ ID NO: 2;

(10) the method of (8) or (9), which comprises the step of introducing said gene transfer vector into a packaging cell into which a packaging vector comprising the nucleotide sequence of SEQ ID NO: 3 has been introduced;

(11) a vector encoding a simian immunodeficiency virus genomic RNA, which comprises the nucleotide sequence of SEQ ID NO: 1, or said sequence to which a foreign gene sequence is inserted;

(12) the vector of (11), wherein the foreign gene is PEDF;

(13) a simian immunodeficiency virus comprising a genomic RNA transcribed from the vector of (11) or (12); and

(14) the simian immunodeficiency virus of (13), which is pseudotyped with VSV-G

BRIEF DESCRIPTION OF THE DRAWINGS

FIG. 7 presents the results of comparing protein expression levels per cell in transgenic cells when each of the gene transfer vectors carrying cPPT alone, WPRE alone, and both cPPT and WPRE was used for infection at MOI of 15. The numbers represent the relative values of fluorescence intensity (a measure of comparing protein expression levels).

BEST MODE FOR CARRYING OUT THE INVENTION

Figure 1:
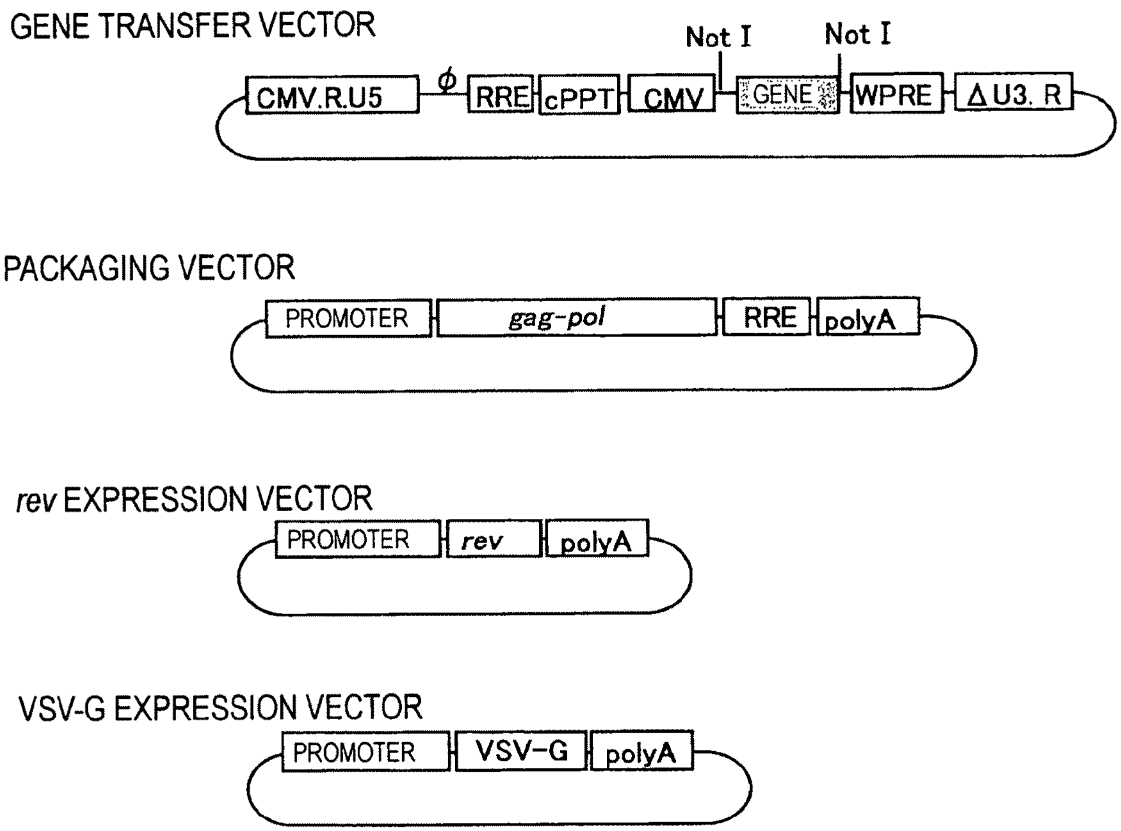
FIG. 1 presents the structures of the improved gene transfer vector, improved packaging vector, rev expression vector, and VSV-G expression vector.

The present invention relates to pharmaceutical agents for treating diseases associated with apoptotic degeneration in ocular tissue cells, which include a recombinant simian immunodeficiency virus vector carrying a pigment epithelium-derived factor (PEDF) gene and a pharmaceutically acceptable vehicle.

The life cycle of viruses can be divided mainly into an infection phase and growth phase. Generally, viral vectors are characterized in that they can utilize the viral infection system to efficiently introduce genes into host cells. To ensure safety, the self-replication ability of many viral vectors are eliminated by removing their growth system, thereby preventing them from growing in the transfected cells.

The structure of vector particles is briefly described below. Vector particles have a protein outer shell called a capsid. The capsid is composed of structural proteins, which are gag gene products. A membrane structure called an envelope is present outside the capsid. The envelope has the function of determining the type of cell that can be infected. Two copies of vector genomic RNA, and a reverse transcriptase, a pol gene product, are present in the capsid. When viral vectors infect host cells, the vector genomic RNA is reverse transcribed by its own reverse transcriptase mentioned above, and then incorporated into the host chromosome to become a proviral DNA, thereby establishing the infection.

Generally, viral vectors can be prepared using packaging vectors and gene transfer vectors. Packaging vectors carry viral DNA in which the packaging signal has been removed. The viral DNA includes viral protein sequences. When packaging vectors are introduced into hosts, due to the lack of a packaging signal, empty viral particles are formed in the host cells (packaging cells). On the other hand, gene transfer vectors carry virus-derived gene sequences that are necessary for being incorporated into host chromosomal DNA, and a foreign gene to be introduced. When such a gene transfer vector is introduced into packaging cells, vector genomic DNA provided by the gene transfer vector is integrated into the host chromosome, and then vector genomic RNA is produced by transcription. This vector genomic RNA is incorporated into viral particles produced by packaging cells, and viral particles capable of introducing nucleic acid molecules into hosts are produced.

In the present invention, the term "viral vector" refers to a viral particle which lacks self-replicating ability, but is capable of transferring nucleic acid molecules into a host. The "recombinant" viral vector refers to a viral vector constructed using genetic recombination technology. Viral vectors constructed using packaging cells and DNA encoding a viral genome are encompassed by the term "recombinant viral vectors".

In the present invention, the term "simian immunodeficiency virus (SIV) vector" refers to a vector in which, among the nucleic acid molecules in the viral particle, sequences necessary to function as a viral vector are based on the SIV genome. As used herein, "sequences necessary to function as a viral vector" refer to the sequences of, in order from the 5' side, the R region and U5 region in the 5' LTR; packaging signal (ϕ); RRE; and U3 region except the promoter region, and R region in the 3' LTR. The nucleotide sequence from the 5' LTR region to the packaging signal is shown in SEQ ID NO: 4, the RRE sequence is shown in SEQ ID NO: 5, and the nucleotide sequence from the U3 region lacking the promoter region to the R region in 3' LTR is shown in SEQ ID NO: 6. The SIV vectors of the present invention can be modified, so long as they fall within the above-mentioned definition. For example, so long as the "sequences necessary to function as a virus vector" are derived from SIV, the vectors may contain other SIV-derived sequences or non-SIV-derived sequences. Sequences that are preferably contained in the vectors include, for example, cPPT, the internal promoter (CMV), and WPRE, which are discussed in further detail later.

In the present invention, the simian immunodeficiency virus (SIV) includes all SIV strains and subtypes. Examples of isolated SIV strains include, but are not limited to, SIVagm, SIVcpz, SIVmac, SIVmnd, SIVsm, SIVsnm, and SIVsyk.

Simian immunodeficiency viruses (SIVs) were discovered as HIV-like viruses in monkeys. SIVs constitute the primate lentivirus group together with HIVs (E. Ido and M. Hayami, "Genes, Infection and Pathogenicity of Simian Immunodeficiency Virus", Tanpakushitsu Kakusan Koso (Protein, Nucleic acid and Enzyme), Vol. 39, No. 8, 1994). This group is further divided into four major subgroups: (1) the HIV-1 group, including HIV-1, which causes human acquired immune deficiency syndrome (AIDS), and SIVcpz, which was isolated from chimpanzees; (2) the HIV-2 group, including SIVsmm isolated from sooty mangabeys (*Cercocebus atys*), SIVmac isolated from rhesus monkeys (*Macaca mulatta*), and HIV-2, which shows pathogenicity in humans at low frequency (Jaffar, S. et al., J. Acquir. Immune Defic. Syndr. Hum. Retrovirol., 16 (5), 327-32, 1997); (3) the SIVagm group, represented by SIVagm isolated from African green monkeys (*Cercopithecus aethiops*); and (4) the SIVmnd group, represented by SIVmnd isolated from mandrills (*Papio sphinx*).

No pathogenicity in natural hosts has been reported for SIVagm and SIVmnd among those described above (Ohta, Y. et al., Int. J. Cancer, 15, 41(1), 115-22, 1988; Miura, T. et al., J. Med. Primatol., 18 (3-4), 255-9, 1989; M. Hayami, Nippon Rinsho, 47, 1, 1989). In particular, the TYO-1 strain of the SIVagm virus, which was used in the Examples herein, has been reported to show no pathogenicity to natural hosts or to experimentally infected crab-eating monkeys (*Macaca facicularis*) and rhesus monkeys (*Macaca mulatta*) (Ali, M. et al., Gene Therapy, 1(6), 367-84, 1994; Honjo, S. et al., J. Med. Primatol., 19 (1), 9-20, 1990). There are no reports of SIVagrn infection and disease occurrence in humans, and its virulence against humans is not known. In general, however, primate lentiviruses have strict species-specificity, and there are few cases in which a virus was transmitted from a natural host to a different species and caused a disease. Moreover, the disease tends to occur at low frequency or progress slowly (Novembre, F. J. et al. J. Virol., 71 (5), 4086-91, 1997). Accordingly, viral vectors that are produced based on SIVagm, in particular based on the SIVagm TYO-1 strain, may be safer than vectors based on HIV-1 or other lentiviruses, and are thus preferably used in the present invention. The genomic nucleotide sequence of the SIVagm TYO-1 strain is shown in SEQ ID NO: 7.

The simian immunodeficiency virus vectors of the present invention may optionally contain a portion of a genomic RNA sequence derived from another retrovirus. For example, the simian immunodeficiency virus vectors of the present invention may also include vectors composed of a chimeric sequence in which a portion of the simian immunodeficiency virus genome has been replaced with a portion of the genomic sequence of another lentivirus, such as the human immunodeficiency virus (HIV), feline immunodeficiency virus (FIV) (Poeschla, E. M. et al., Nature Medicine, 4 (3), 354-7, 1998), or caprine arthritis encephalitis virus (CAEV) (Mselli-Lakhal, L. et al., Arch. Virol., 143(4), 681-95, 1998).

In the present invention, a recombinant simian immunodeficiency virus vector carrying a pigment epithelium derived factor (PEDF) gene (i.e., an SIV-PEDF vector) refers to recombinant SIV vectors carrying a PEDF gene. The cDNA sequence of human PEDF (hPEDF) is shown in SEQ ID NO:

8. Types and structures of the SIV-PEDF vectors of the present invention are not limited, so long as they fall within the definition described above. However, preferred examples include SIV vectors produced using a gene transfer vector containing a nucleotide sequence in which a PEDF gene sequence has been inserted into the nucleotide sequence of SEQ ID NO: 1; and more preferred examples include SIV vectors produced using a gene transfer vector containing the nucleotide sequence of SEQ ID NO: 2.

The SIV-PEDF vector of the present invention may be pseudotyped with VSV-G. The term "pseudotyping with VSV-G" refers to incorporating the VSV-G protein, a surface glycoprotein of vesicular stomatitis virus (VSV), into the envelope of the vector. The VSV-G protein may be derived from an arbitrary VSV strain. Examples of VSV-G proteins include, but are not limited to, proteins derived from the Indiana serotype strain (J. Virology 39: 519-528 (1981)). Alternatively, the VSV-G protein can be a modified VSV-G protein derived from the original protein by, for example, substituting, deleting, and/or adding one or more amino acids. VSV-G-pseudotyped vectors can be prepared by allowing the VSV-G protein to be present during viral production. Viral particles produced in packaging cells can be pseudotyped with VSV-G by expressing VSV-G in these cells. This can be facilitated by, for example, transfection of a VSV-G expression vector, or induced expression of the VSV-G gene integrated into the host's chromosomal DNA. Since VSV-G protein is present on the membrane as a stable glycoprotein homotrimer, vector particles suffer little deterioration during purification and thus can be concentrated to high concentrations using centrifugation (Yang, Y et al., Hum Gene Ther: September, 6(9), 1203-13. 1995).

The SIV-PEDF vector of the present invention may further contain envelope proteins from other viruses. For example, an envelope protein derived from a virus which infects human cells is preferred as such a protein. Examples of such proteins include, but are not limited to, retroviral amphotropic envelope proteins. For example, the envelope protein derived from murine leukemia virus (MuLV) 4070A strain can be used as such a retroviral amphotropic envelope protein. Alternatively, the envelope protein derived from MuMLV 10A1 can also be used (for example, pCL-10A1 (Imgenex) (Naviaux, R. K. et al., J. Virol. 70: 5701-5705 (1996)). Also included are proteins from the herpes virus family, such as the gB, gD, gH, and gp85 proteins derived from the herpes simplex virus, and the gp350 and gp220 proteins from the EB virus. Proteins from the Hepadna virus family may include the S protein of hepatitis B virus.

In the recombinant simian immunodeficiency virus vector of the present invention, the LTR (long terminal repeat) may also be modified. The LTR is a retrovirus-specific sequence, which is present at both ends of the viral genome. The 5' LTR serves as a promoter, enhancing proviral mRNA transcription. Thus, it may be possible to enhance mRNA transcription of the gene transfer vector, improve packaging efficiency, and increase vector titer if the portion exhibiting the 5' LTR promoter activity in the gene transfer vector that encodes viral RNA genome packaged into viral particles, is substituted with another promoter having stronger promoter activity. Furthermore, for example, in the case of lentiviruses, viral tat is known to enhance 5' LTR transcription activity, and therefore, substitution of the 5' LTR for a promoter not present on the tat protein will enable the exclusion of tat from the packaging vector. The RNA of viruses which have infected or invaded cells is reverse transcribed, and the subsequent linking of the LTRs at both ends forms a closed circular structure. Then, viral integrase couples with the linkage site and this structure is then integrated into cell chromosomes. The transcribed proviral mRNA is the region ranging from the 5' LTR transcription initiation site to the 3' LTR polyA sequence located downstream. The 5' LTR promoter portion is not packaged in the virus particle. Thus, even if the promoter is replaced with another sequence, the portion integrated into target cell chromosomes is unchanged. Given the facts as described above, it is proposed that substitution of the 5' LTR promoter will yield a safer vector with a higher titer. Thus, substitution of the promoter at the 5' end of a gene transfer vector can increase the titer of a packagable vector.

Safety can also be improved by preventing transcription of the full-length vector mRNA in target cells. This is achieved using a self-inactivating vector (SIN vector) prepared by partially eliminating the 3' LTR sequence. The lentivirus provirus invading the target cell chromosomes has its 5' end bound to the U3 portion of its 3' LTR. Thus, following reverse-transcription, transcripts of the gene transfer vector are integrated into target cell chromosomes such that the U3 portion is at the 5' end. From this point begins the transcription of RNA with a structure similar to the gene transfer vector transcripts. If there were lentivirus or related proteins in target cells, it is possible that the transcribed RNA would be re-packaged and infect other cells. There is also a possibility that the 3' LTR promoter might express host genes located adjacent to the 3' end of the viral genome (Rosenberg, N., Jolicoeur, P., Retroviral Pathogenesis. Retroviruses. Cold Spring Harbor Laboratory Press, 475-585, 1997). These are already considered to be problems of retroviral vectors, and the SIN vector was developed as a way of overcoming these problems (Yu, S. F. et al., Proc. Natl. Acad. Sci. USA, 83(10), 3194-8, 1986). When the 3'LTR U3 portion is deleted from a gene transfer vector, target cells lack the promoters of 5' LTR and 3' LTR, preventing the transcription of the full-length viral RNA and host gene. Furthermore, since only the genes of interest are transcribed from endogenous promoters, highly safe vectors capable of high expression can be expected. Such vectors are preferred in the present invention. SIN vectors can be constructed according to methods known in the art, or methods as described in Examples 1 to 4 of WO 2002/101057 (Patent Document 1), which is a patent application by the present inventors.

One problem encountered in gene therapy using viral vectors that have the LTR sequence in its genome, (including retroviral vectors) is a gradual decrease in expression of the introduced gene. One factor behind this may be that when such a vector is integrated into the host genome, a host mechanism methylates the LTR, suppressing expression of the introduced gene (Challita, P. M. and Kohn, D. B., Proc. Natl. Acad. Sci. USA 91:2567, 1994). One advantage of SIN vectors is that LTR methylation hardly reduces gene expression level. This is because the vector loses most of the LTR sequence upon integration into the host genome. The present inventors revealed that an SIN vector, prepared by substituting another promoter sequence for the 3' LTR U3 region of the gene transfer vector, maintained a stable expression for more than two months after gene transfer into primate ES cells (Patent Document 1). Thus, an SIN vector designed to self-inactivate by the modification of the LTR U3 region is particularly suitable in the present invention. Specifically, the present invention includes modified vectors in which one or more nucleotides in the 3' LTR U3 region have been substituted, deleted, and/or added. The U3 region may simply be deleted, or another promoter may be inserted into this region. Such promoters include, for example, the CMV promoter, the EF1 promoter, and the CAG promoter.

It is preferable to design the PEDF gene encoded by the vector of the present invention in such a way that it can be transcribed by a promoter other than LTR. For example, when the LTR U3 region is replaced with a non-LTR promoter as described above, it is preferable that the modified LTR drives the expression of the PEDF gene. Alternatively, as shown in the Examples, the expression of the PEDF gene can be induced independently of the LTR by placing a non-LTR promoter in a position other than the LTR region, and placing the PEDF gene downstream of this position. The present inventors showed that an SIV vector in which the expression of the PEDF gene is regulated by a non-LTR promoter ensures long-term stable expression of the PEDF gene in ES cells (Patent Document 1). Similarly, a vector in which a non-LTR promoter is placed upstream of the PEDF gene, and where the PEDF gene is transcribed under the control of that promoter, is particularly suitable in the present invention. Such non-LTR promoters include the CMV promoter, EF1 promoter, and CAG promoter. The CMV promoter in particular is preferable. The nucleotide sequence of the CMV promoter used in the Examples is shown in SEQ ID NO: 9. Such a vector is highly effective when constructed based on the SIN vector described above.

A risk that has been pointed out concerning lentivirus vectors such as the HIV vector is that they may produce replicable viral particles if the host genome already has the HIV provirus, and recombination occurs between the foreign vector and the endogenous provirus. This is predicted to become a serious problem in the future, when the HIV vector is used in HIV patients. The SIV vector used in the present invention has low sequence homology with HIV, and cannot replicate as a virus because 80% or more of the virus-derived sequence has been removed from the vector. Thus, this vector does hardly pose this risk and is therefore safer than other lentivirus vectors. The SIV-PEDF vector of the present invention is a vector in which a certain percentage or more of the SIV genomic sequence has been removed except for the "sequences necessary to function as a virus vector" described above. The preferred SIV vector of the present invention is a replication-incompetent virus from which 40% or more, more preferably 50% or more, still more preferably 60% or more, even more preferably 70% or more, and most preferably 80% or more of the genomic sequence of the original SIV has been removed.

Retroviruses can be produced by transcribing in host cells a gene transfer vector DNA which contains a packaging signal. This allows the formation of virus particles in the presence of the gag, pol and envelope proteins. The gag and pol proteins in the packaging cells can be supplied using packaging vectors. The envelope proteins may be supplied by packaging vectors or other vectors. For example, the envelope proteins may be supplied using a VSV-G expression vector as described in the Examples herein.

The gene transfer vector of the present invention has, at its most basic level, a 5' LTR, a packaging signal sequence, a PEDF or FGF2 gene, and a 3' LTR sequence. The LTR sequences may contain modifications made to the LTR sequences of the SIV vectors mentioned above. In addition, the cPPT sequence, CMV sequence, RRE sequence or such described above may be incorporated into the vector. The packaging signal sequence encoded by the gene transfer vector DNA should preferably be sufficient in length to maintain the structure formed by the sequence. However, in order to suppress the frequency of wild-type virus formation, which occurs due to recombination of the vector DNA packaging signal and the packaging vector supplying the gag and pol proteins, it is also necessary to keep sequence overlapping between these vector sequences to a minimum. Therefore, when it comes to the construction of the gene transfer vector DNA, it is preferable to use a sequence which is as short as possible and yet still contains the sequence essential for packaging, to ensure packaging efficiency and safety.

For example, when the packaging vector is derived from SIVagm, the virus from which the packaging signal to be used in the gene transfer vector DNA is derived is limited to SIV, because HIV-derived gene transfer vectors are not packaged. However, the SIV-derived gene transfer vector is also packagable when an HIV-derived packaging vector is used. Thus, the frequency of recombinant virus formation can be reduced if the vector particles are formed by combining the gene transfer vector and packaging vector, wherein each vector is derived from a different type of lentivirus. SIV vectors thus produced are also included in vectors of the present invention. In such cases, it is preferable to use combinations of primate lentiviruses (for example, HIV and SIV).

In a preferred gene transfer vector DNA, the gag protein has been modified such that it is not expressed. Viral gag protein may be detected by a living body as a foreign substance, and thus serves as a potential antigen. Alternatively, the protein may affect cellular functions. To prevent gag protein expression, nucleotides downstream of the gag start codon can be added or deleted, introducing modifications which will cause a frameshift. It is also preferable to delete portions of the coding region of the gag protein. The 5' portion of the coding region of the gag protein is known to be essential for virus packaging. Thus, in a gene transfer vector, it is preferable that the coding region for the gag protein is deleted at the C terminus. It is preferable to delete as large a portion of the gag coding region as possible, so long as the deletion does not considerably affect the packaging efficiency. It is also preferable to replace the start codon (ATG) of the gag protein with a codon other than ATG. The replacement codon can be selected appropriately so as not to greatly affect the packaging efficiency. A viral vector can be produced by introducing the constructed gene transfer vector DNA, which includes the packaging signal, into appropriate packaging cells. The viral vector particles produced can be recovered from, for example, the culture supernatant of packaging cells.

Furthermore, a gene transfer vector DNA is preferably modified to increase the transfer and expression efficiency of the PEDF gene. An example of a modification that increases the transfer efficiency is introduction of a cPPT (central polypurine tract) sequence. cPPT is a sequence originally present in the SIV genome. cPPT has been reported for HIV viruses since quite some time ago (P. Chameau et al.: J. Virol. 65: 2415-2431, 1991), and it has been reported that cPPT introduced in HIV vectors improves the transfer of the vector genome to nuclei and increases the gene transfer efficiency (A. Sirven et al.: Blood 96:4103-4110, 2000). The nucleotide sequence of cPPT used in the Examples is shown in SEQ ID NO: 10. Meanwhile, an example of a modification that increases the expression efficiency is introduction of a woodchuck hepatitis virus posttranscriptional regulatory element (WPRE) sequence. WPRE is a factor that has a function of increasing gene expression efficiency (U.S. Pat. No. 6,284, 469: RNA export element and methods of use). In other lentiviral vectors, simultaneous introduction of the two factors, cPPT and WPRE, has been reported to further enhance the effects of each factor (S C. Barry et al.: Hum. Gene Ther. 12:1103-1108, 2001). The nucleotide sequence of WPRE used in the Examples is shown in SEQ ID NO: 11. In the SIV-PEDF vectors of the present invention, cPPT can be positioned as in ordinary lentiviral vectors. For example, cPPT may be placed between the promoter and the foreign gene, or placed upstream of the RRE sequence; however, it is preferably placed upstream of the above-described non-LTR promoter, which drives the transcription of PEDF. WPRE can be positioned downstream of the PEDF gene. Specific preferred examples of such gene transfer vectors include SIV vectors produced using a gene transfer vector containing a nucleotide sequence in which a PEDF gene has been inserted into the nucleotide sequence of SEQ ID NO: 1. More preferred examples include SIV vectors produced using a gene transfer vector containing the nucleotide sequence of SEQ ID NO: 2.

In the present invention, packaging vectors in which sequences not necessary for PEDF gene transfer have been removed may be used. Examples of unnecessary sequences include vif and vpr, which are called accessory genes, and the regulatory genes tat and rev. Accessory gene products have been reported to be not essential in vectors (V. Kim et al.: J. Virol 72: 811-816, 1998), and therefore accessory gene-deleted vectors have been recently used to improve safety. Furthermore, even safer vectors called third generation vectors have been developed by deleting tat and transferring rev to a different plasmid. When rev is removed from the packaging vector, a rev expression vector can be constructed separately and used to produce SIV-PEDF vectors of the present invention. The nucleotide sequence of rev of the SIVagm TYO-1 strain is shown in SEQ ID NO: 12. Packaging vectors constructed as described above may contain, for example, a promoter sequence, a virus core protein sequence (gag), a reverse transcriptase sequence (pol), and a polyA sequence. The packaging vector may further contain an RRE sequence as well as the above components, as indicated in the Examples below. In addition, the rev expression vector may be constructed such that a promoter for regulating the rev sequence is positioned upstream of the rev sequence, and a polyA sequence is positioned downstream of the rev sequence.

There is no limitation on the type of packaging cell, so long as the cell line is generally used in viral production. When used for human gene therapy, a human- or monkey-derived cell is suitable. Human cell lines that can be used as packaging cells include, for example, 293 cells, 293T cells, 293EBNA cells, SW480 cells, u87MG cells, HOS cells, C8166 cells, MT-4 cells, Molt-4 cells, HeLa cells, HT1080 cells, TE671 cells, etc. Monkey cell lines include, for example, COS1 cells, COS7 cells, CV-1 cells, BMT10 cells, etc.

The SIV-PEDF vectors of the present invention can be substantially purified. The purification can be achieved using known purification and separation methods, such as filtration, centrifugation, and column purification. For example, a vector can be precipitated and concentrated by filtering a vector solution with a 0.45-μm filter, and then centrifuging it at 42500×g at 4° C. for 90 minutes.

The SIV-PEDF vectors of the present invention can be used to treat and prevent diseases associated with apoptotic degeneration in ocular tissue cells. As described in the Examples herein, the present inventors have confirmed, using disease model animals, that the SIV-PEDF vectors are very effective for retinal ganglion cell protection. The final pathology of glaucoma is apoptosis of retinal ganglion cells. Thus, the SIV-PEDF vectors of the present invention are effective in suppressing the progress of, preventing, and treating glaucoma by suppressing apoptosis of retinal ganglion cells. Furthermore, the vectors may be widely used for treating diseases, other than glaucoma, associated with apoptotic degeneration in ocular tissue cells. The SIV-PEDF vectors of the present invention can be appropriately combined with desired pharmaceutically acceptable carriers or vehicles if necessary to prepare pharmaceutical agents for treating diseases associated with apoptotic degeneration in ocular tissue cells. The term "pharmaceutically acceptable carrier" refers to a material that can be administered in conjunction with the vector and does not significantly inhibit gene transfer mediated by the vector. Specifically, the vector can be appropriately combined with, for example, sterilized water, physiological saline, culture medium, serum, and phosphate buffered saline (PBS). In addition, a stabilizer, biocide, and such can also be included. When administering a pharmaceutical agent of the present invention composed of SIV-PEDF for treating diseases associated with apoptotic degeneration in ocular tissue cells, the route of administration is not particularly limited, so long as it yields retinal ganglion cell-protecting effect, but is preferably subretinal administration, intravitreal administration, or intracameral administration, and is more preferably subretinal administration or intravitreal administration. The dose of the pharmaceutical agent composed of SIV-PEDF of the present invention (per human eye) is, as a guide, for example, $2.5\times10^5$ TU to $2.5\times10^8$ TU, or preferably $5.0\times10^5$ TU to $5.0\times10^7$ TU.

All prior art references cited herein are incorporated herein by reference.

EXAMPLES

Herein below, the present invention will be specifically described with reference to Examples, but it is not to be construed as being limited thereto.

Example 1

Construction of VSV-G Pseudotyped SIV Vectors

The four types of plasmids (gene transfer vector, packaging vector, rev expression vector, and VSV-G expression vector) used for vector construction are shown in FIG. 1. Three of these vectors—the gene transfer vector, packaging vector, and rev expression vector—were produced by improving conventional vector plasmids (PCT/JP00/03955). For the VSV-G expression vector, a conventional vector was used without modification.

Various commercially available kits were used for plasmid production. The restriction enzymes used were from New England Biolabs, and kits from QIAGEN (QIAquick PCR purification kit, QIAquick Nucleotide Removal kit, QIAquick Gel extraction kit, Plasmid Maxi kit) were used to extract, purify and recover plasmid DNAs. EX Taq enzyme from TaKaRa was used for PCR, and the primers used were synthesized by an outside manufacturer (Sigma Genosys Japan). Alkaline phosphatase (*E. coli* C75) from TaKaRa was used for dephosphorylation of DNA ends. DNA Ligation kit ver. 2 from TaKaRa was used for ligation, and DH5α COMPETENT high from TOYOBO was used for transformation.

1-1. Improving the Gene Transfer Vector

Figure 2A:
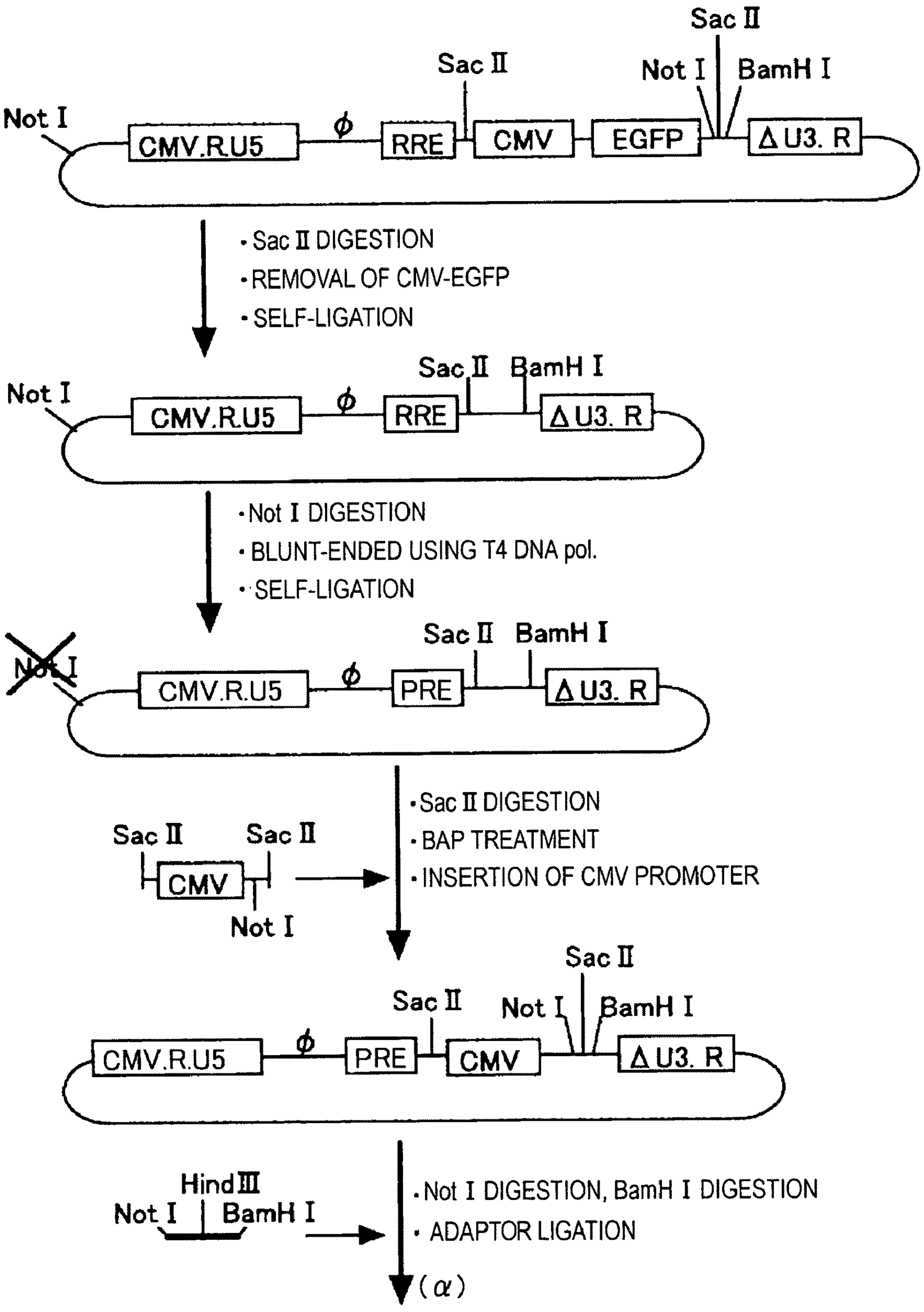
FIG. 2A illustrates the steps for constructing an improved gene transfer vector from a conventional gene transfer vector. (α) indicates continuation to the steps of FIG. 2B.
Figure 2B:
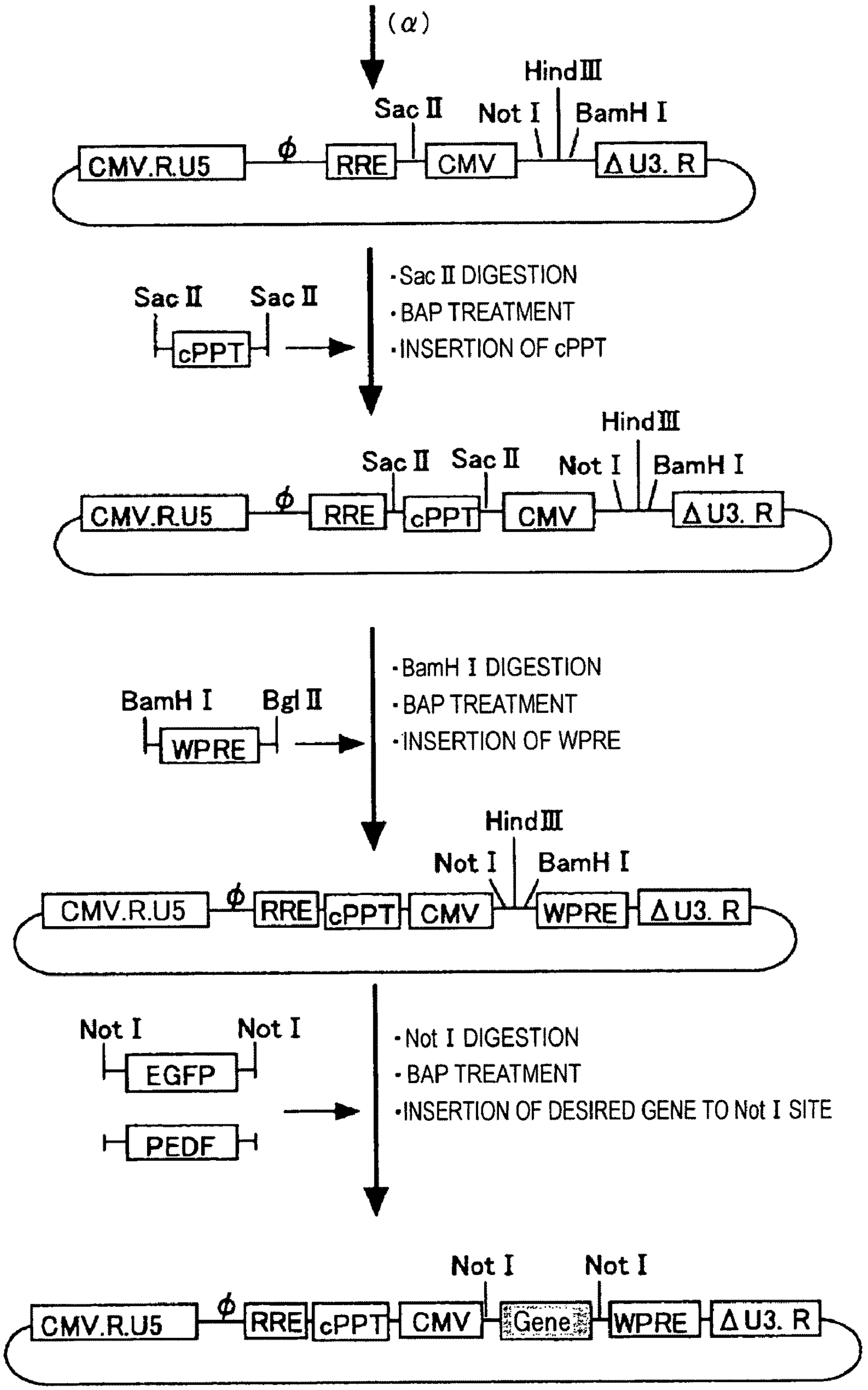
FIG. 2B is the continuation of FIG. 2A. (α) indicates continuation from the steps of FIG. 2A.

Central polypurine tract (cPTT) and woodchuck hepatitis virus posttranscriptional regulatory element (WPRE) were introduced into a conventional gene transfer vector to improve the performance of the gene transfer vector (FIG. 2). The conventional gene transfer vector used was based on SIVagm, a nonpathogenic clone of African green monkey immunodeficiency virus, and included a 5' LTR region, RRE, cytomegalovirus (CMV) promoter, enhanced green fluorescent protein (EGFP) gene, and 3' LTR in this order. The conventional gene transfer vector was constructed by the present inventors, and the method for construction and such have been previously reported in the literature (Patent Document 2). SEQ ID NO: 13 shows the nucleotide sequence of the conventional gene transfer vector.

The specific method used to modify the vector is as follows: First, the conventional gene transfer vector was digested with restriction enzyme Sac II. The sample was electrophoresed to remove the CMV promoter and the EGFP gene, and then self-ligated. Next, to remove the Not I site of the plasmid, the above vector was digested with Not I, blunt-ended using T4 DNA polymerase, and then self-ligated.

Thereafter, the vector mentioned above was digested with restriction enzyme Sac II, and treated with BAP to dephosphorylate the digested ends. PCR was performed using the conventional gene transfer vector as a template and using primers 1F (SEQ ID NO: 14) and 1R (SEQ ID NO: 15), and the PCR product was digested with Sac II to produce a fragment with a Sac II site added to the ends of the CMV promoter (SEQ ID NO: 9). This CMV promoter fragment was inserted into the Sac II site of the BAP-treated vector mentioned above.

The vector was digested sequentially with Not I and BamH I, and the digested site was then ligated with an adaptor produced by annealing two synthetic oligo DNAs, 2F (SEQ ID NO: 16) and 2R (SEQ ID NO: 17), to modify the restriction enzyme sites. The vector was digested with restriction enzyme Sac II, and treated with BAP to dephosphorylate the digested ends.

To obtain a cPTT fragment (SEQ ID NO: 10) to be inserted, PCR was performed using plasmid pSA212, into which the SIVagmTY01 genome (SEQ ID NO: 7) was incorporated, as a template and using primers 3F (SEQ ID NO: 18) and 3R (SEQ ID NO: 19). The ends of the PCR amplified fragment were digested with Sac II to produce a fragment with Sac II sites added to both ends of cPPT. The cPPT fragment was ligated to the Sac II site of the above BAP-treated vector.

The vector was digested with BamH I and treated with BAP to dephosphorylate the digested ends. To obtain a WPRE fragment to be inserted, PCR was performed using a plasmid carrying WPRE cDNA (SEQ ID NO: 11) as a template and using primers 4F (SEQ ID NO: 20) and 4R (SEQ ID NO: 21). The ends of the obtained PCR amplification product were digested with BamH I and Bgl II to produce a fragment with restriction enzyme sites added to the ends of WPRE. The above WPRE fragment was ligated to the BamH I site of the vector to complete an improved gene transfer vector (SEQ ID NO: 1) that has no inserted gene.

Gene fragments to be inserted were produced and inserted into the Not I site of the above improved gene transfer vector. An EGFP fragment was prepared by performing PCR using a plasmid carrying the EGFP cDNA (SEQ ID NO: 22) as a template and using primers 5F (SEQ ID NO: 23) and 5R (SEQ ID NO: 24), and then digesting the PCR product with NotI. A PEDF fragment was prepared by performing PCR using a plasmid carrying the hPEDF cDNA (SEQ ID NO: 8) as a template and using primers 7F (SEQ ID NO: 25) and 7R (SEQ ID NO: 26), cloning the PCR product into the pGEM-T Easy vector (Promega) by the TA cloning method, and then cutting out the fragment with Not I.

Furthermore, in addition to the construction of the plasmid carrying cPPT and WPRE, gene transfer vectors carrying cPPT or WPRE alone were prepared in order to confirm the effects of cPPT and WPRE.

1-2. Improving the Packaging Vector

Figure 3:
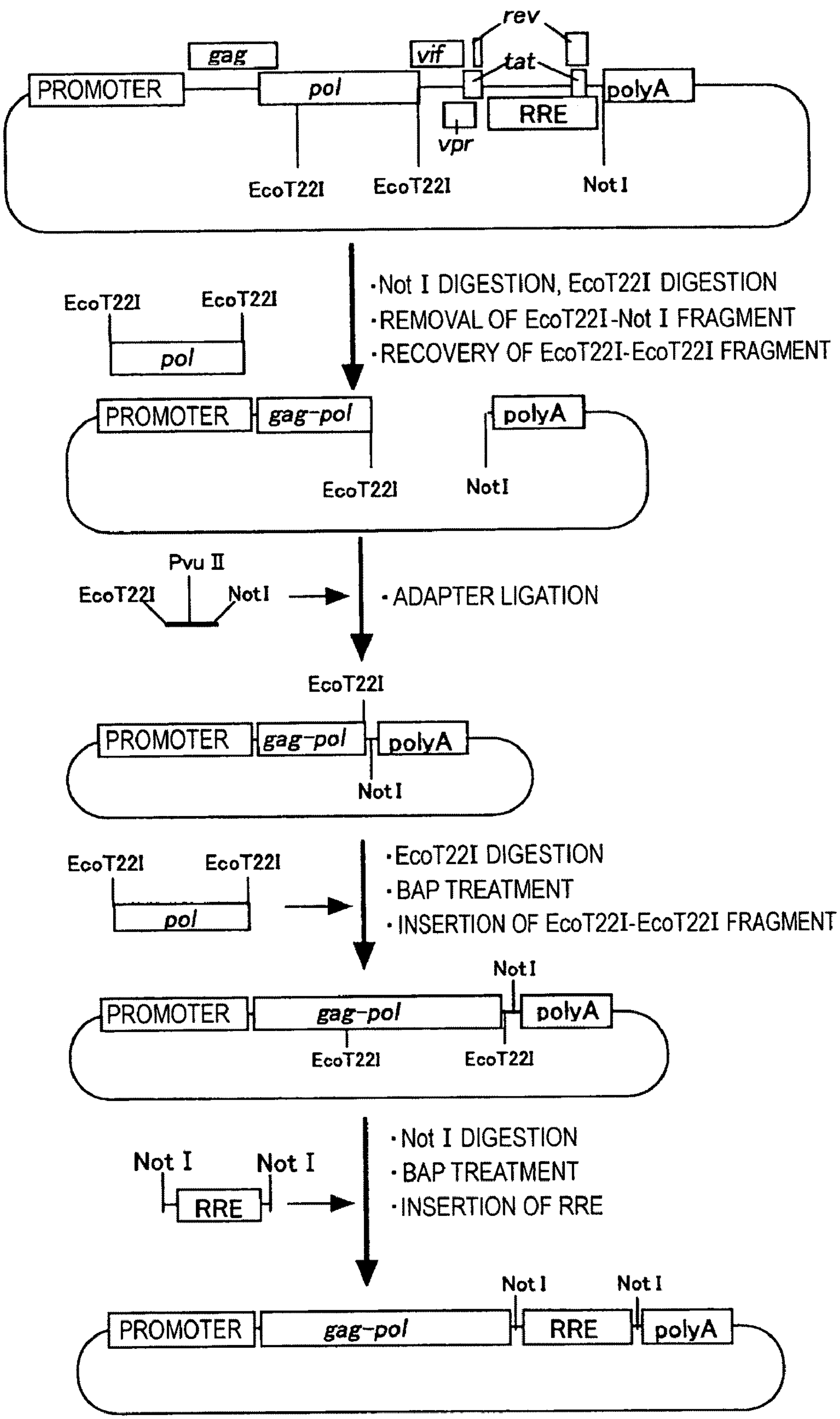
FIG. 3 describes the steps for constructing an improved packaging vector from a conventional packaging vector.

Conventional packaging vectors include vif and vpr, which are called accessory genes, and regulatory gene tat and rev, in addition to gag and pol. However, since accessory gene products were found not to be essential for the vectors (V. Kim et al.: J. Virol. 72:811-816, 1998), vectors in which the accessory genes have been deleted have been recently used for improved safety. Furthermore, even safer vectors called third generation vectors have been developed by further deleting tat and transferring rev to a different plasmid. At present, it has become essential to convert vectors into third generation vectors. Accordingly, in the present invention as well, the auxiliary genes (vif, vpr, and tat) were removed from the conventional packaging vector (SEQ ID NO: 27), and rev was transferred to a different plasmid, for achieving high safety (FIG. 3). The basis of this method has been previously reported with HIV vectors (T. Dull, et al.: J. Virol 72:8463-8471, 1998).

Specifically, the plasmid of the packaging vector was first digested with restriction enzyme Not I, and then digested with EcoT22I. The sample was electrophoresed to remove the EcoT22I-Not I fragment, and then the large vector fragment and the EcoT22I-EcoT22I fragment, a part of the pol gene, were recovered.

An adaptor produced by annealing two synthetic oligo DNAs, 1F (SEQ ID NO: 28) and 1R (SEQ ID NO: 29), was ligated to the EcoT22I-Not I site of the above vector. Subsequently, the vector was digested with EcoT22I, and treated with BAP to dephosphorylate the digested ends. The EcoT22I fragment of the pol gene recovered in advance was inserted into the BAP-treated EcoT22I site.

The above vector was digested with Not I, and treated with BAP to dephosphorylate the digested ends. To obtain an RRE fragment, PCR was performed using the conventional packaging vector (SEQ ID NO: 27) as a template and using primers 8F (SEQ ID NO: 30) and 8R (SEQ ID NO: 31), and the PCR product was cloned into the pGEM-T Easy vector (Promega) by the TA cloning method. The RRE fragment was cut out with Not I. The RRE fragment was ligated to the dephosphorylated Not I site of the vector to complete the improved packaging vector (SEQ ID NO: 3).

1-3. Construction of the rev Expression Vector

Figure 4A:
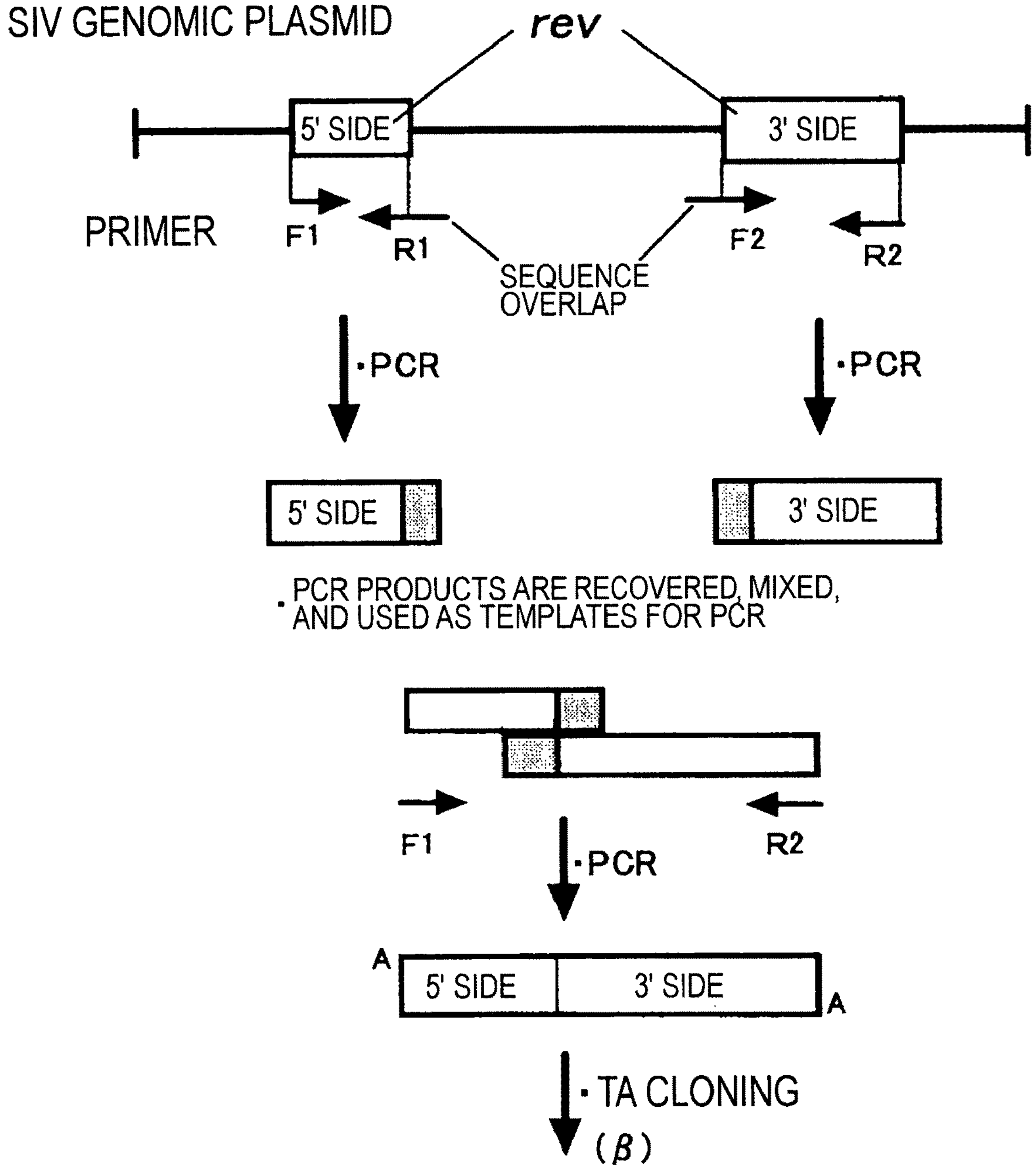
FIG. 4A describes the steps for constructing a rev expression vector. (β) indicates continuation to the steps of FIG. 4B.
Figure 4B:
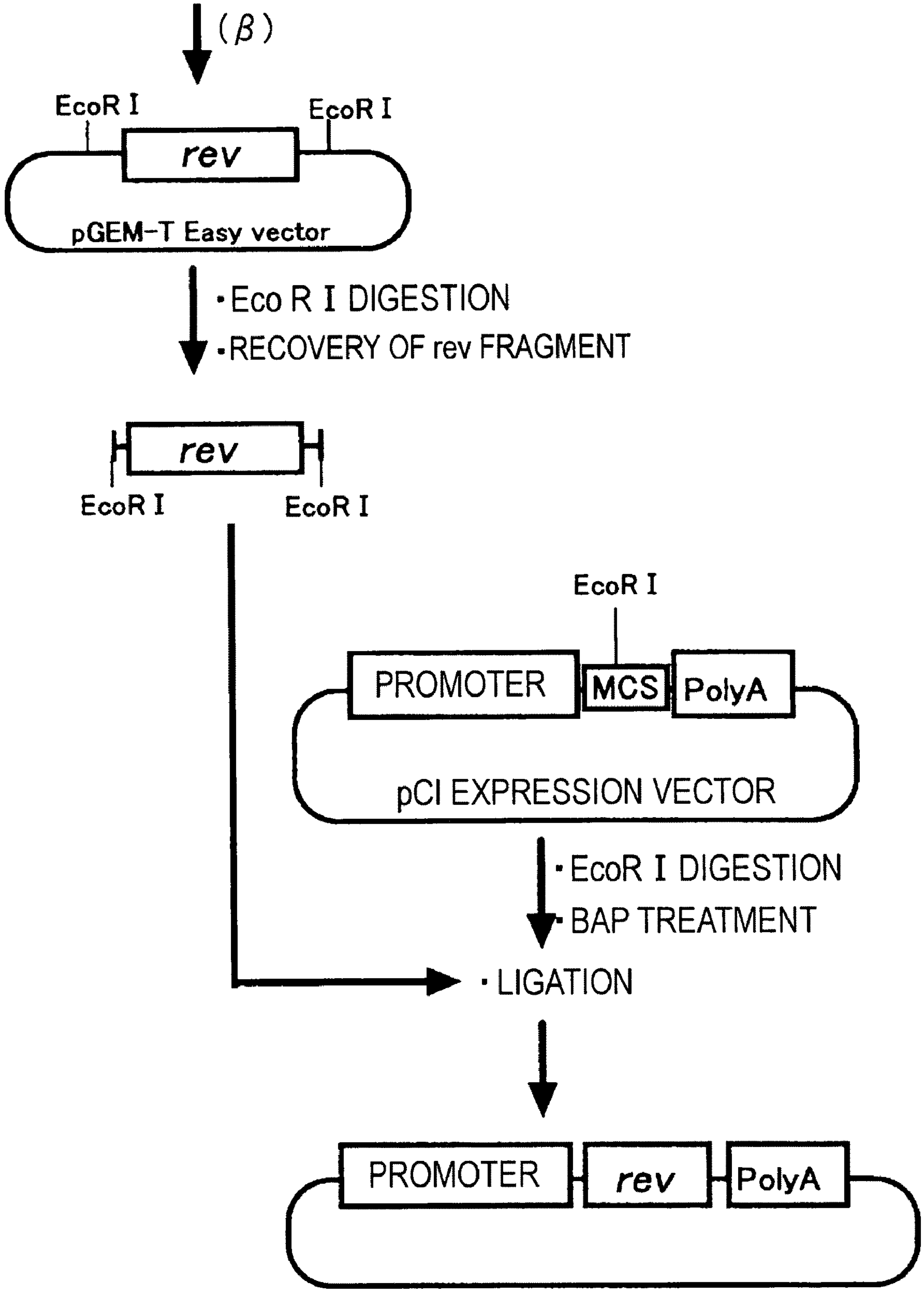
FIG. 4B is the continuation of FIG. 4A. (β) indicates continuation from the steps of FIG. 4A.

Previously, the rev protein has been supplied by conventional packaging vectors. However, with the above improvements of the packaging vector, a new expression vector was constructed in order to supply the rev protein from a separate expression plasmid. Although rev is separated into two parts by an intron in the genome, the parts were combined together and inserted into the expression plasmid (FIG. 4).

First, a conventional packaging vector was used as a template, and two fragments were produced by PCR. The 5'-side fragment was amplified using primers 1F (SEQ ID NO: 32) and 1R (SEQ ID NO: 33), and the 3'-side fragment was amplified using primers 2F (SEQ ID NO: 34) and 2R (SEQ ID NO: 35). The two PCR fragments were recovered, mixed, and used as PCR templates. They were amplified using primers 1F and 2R to obtain the desired rev gene fragment (SEQ ID NO: 12) in which the two fragments were linked. The PCR-amplified rev fragment was cloned into the pGEM-T Easy vector by the TA cloning method. Next, the vector was digested with EcoR I, and the rev fragment to which EcoR I sites were added was recovered. Meanwhile, the pCI vector for protein expression (Promega) was digested with EcoR I, and the digested sites were treated with BAP. The recovered rev fragment and the pCI expression vector were ligated to produce the rev expression vector.

Example 2

Evaluation of Function of the SIV Vector Carrying cPPT and WPRE

To investigate the effect of the introduced cPPT and WPRE, vectors carrying cPPT or WPRE alone were produced as well as those carrying cPPT and WPRE simultaneously, and these were compared to the conventional type control. All gene transfer vectors used carried EGFP. The packaging vector used was a conventional type (SEQ ID NO: 27).

2-1. Preparation of SIV Vectors

Human fetal kidney cell-derived cell line 293T cells were plated in 15-cm plastic dishes at approximately $1\times10^7$ cells per dish (a density to reach 70-80% on the following day) and cultured for 24 hours in 20 mL of D-MEM medium (Gibco BRL) containing 10% fetal calf serum. After culturing the cells for 24 hours, the medium was replaced with 10 mL of OPTI-MEM medium (Gibco BRL), and the cells were used for transfection.

After 6 μg of the gene transfer vector, 3 μg of the packaging vector, and 1 μg of the VSV-G expression vector were dissolved in 1.5 mL of OPTI-MEM medium per dish, 40 μL of PLUS Reagent (Invitrogen) was added and stirred. Then the mixture was left to stand at room temperature for 15 minutes. The gene transfer vector used was a vector carrying both cPPT and WPRE, cPPT alone, or WPRE alone, or a conventional-type vector (not carrying cPPT nor WPRE). After 60 μL of Lipofectamine Reagent (Invitrogen) diluted in 1.5 mL of OPTI-MEM medium was added, the mixture was stirred and then left to stand at room temperature for 15 minutes.

The above DNA complex was added dropwise to the cells in the 15-cm dishes, and mixed by gentle shaking. The cells were then incubated for three hours at 37° C. in a 5% $CO_2$ incubator. After the incubation, 13 mL of D-MEM medium containing 20% fetal calf serum was added to the dishes and cultured. On the next day of transfection, the medium was replaced with 30 mL of fresh D-MEM medium containing 10% fetal calf serum, and the cells were cultured. Two days after transfection, the supernatant was collected and filtered through a 0.45 μm filter to obtain a vector solution.

2-2. Measurement of SIV Vector Titers

There are two types of titers for the SIV vectors: the functional titer (TU/mL) calculated from the number of cells expressing the protein of the carried gene, and the particle titer (particles/mL) calculated from the number of vector particles. Since the performance of cPPT and WPRE would be evaluated in cells infected with the same particle titer, particle titers were measured by the dot blotting method as described below.

First, RNAs were extracted from the vector solution produced as above using a commercially available kit (QIAamp Viral RNA mini kit, QIAGEN). Next, RNAs were blotted on Hybond N+ membranes (Amersham) using a slot blotter. At the same time, plasmid DNA whose number of moles had been calculated was also blotted for preparing a calibration curve. The method for treating the RNAs followed the protocol accompanying the membrane. DNA was heated and rapidly cooled. After alkaline fixation of the membrane, hybridization was carried out. The DIG label-based detection system from Roche was used for hybridization. Probes were produced using DIG-labeled NTPs, and DIG Easy Hyb, DIG Wash, and Block Buffer Set (Roche) were used for the procedures after hybridization. Anti-DIG AP conjugate antibody (Roche) and CSPD (Roche) were used for chemiluminescence, and signals were detected and quantified using a luminoimage analyzer (Fuji Film: LAS-1000).

2-3. Gene Transfer into Cells by SIV Vectors and its Evaluation

The four vectors, whose particle titers had been measured, were infected into cells at different multiplicities of infection (MOIs) as described below and subjected to FACS analysis. 293T cells were plated onto 6-well plastic culture plates at $1\times10^6$ cells per well, and the cells were incubated overnight at 37° C. in 5% $CO_2$. On the following day, the number of cells per well of the plate was calculated using a hemocytometer. The medium in the plate was removed, and the vectors diluted with 2 mL of fresh D-MEM medium containing 10% fetal calf serum were added at MOIs (particles/cell) of 0.3, 1.5, 7.5, and 15. One day after infection, the cell culture medium was exchanged with 2 mL of fresh medium. Two days after infection, EGFP that was transferred by the vector was observed under a fluorescence microscope to measure the percentage of EGFP-positive cells. Then, fluorescence intensities (values indicating EGFP protein levels) were also measured.

2-4. Results of Evaluating Vector Function

Figure 5:
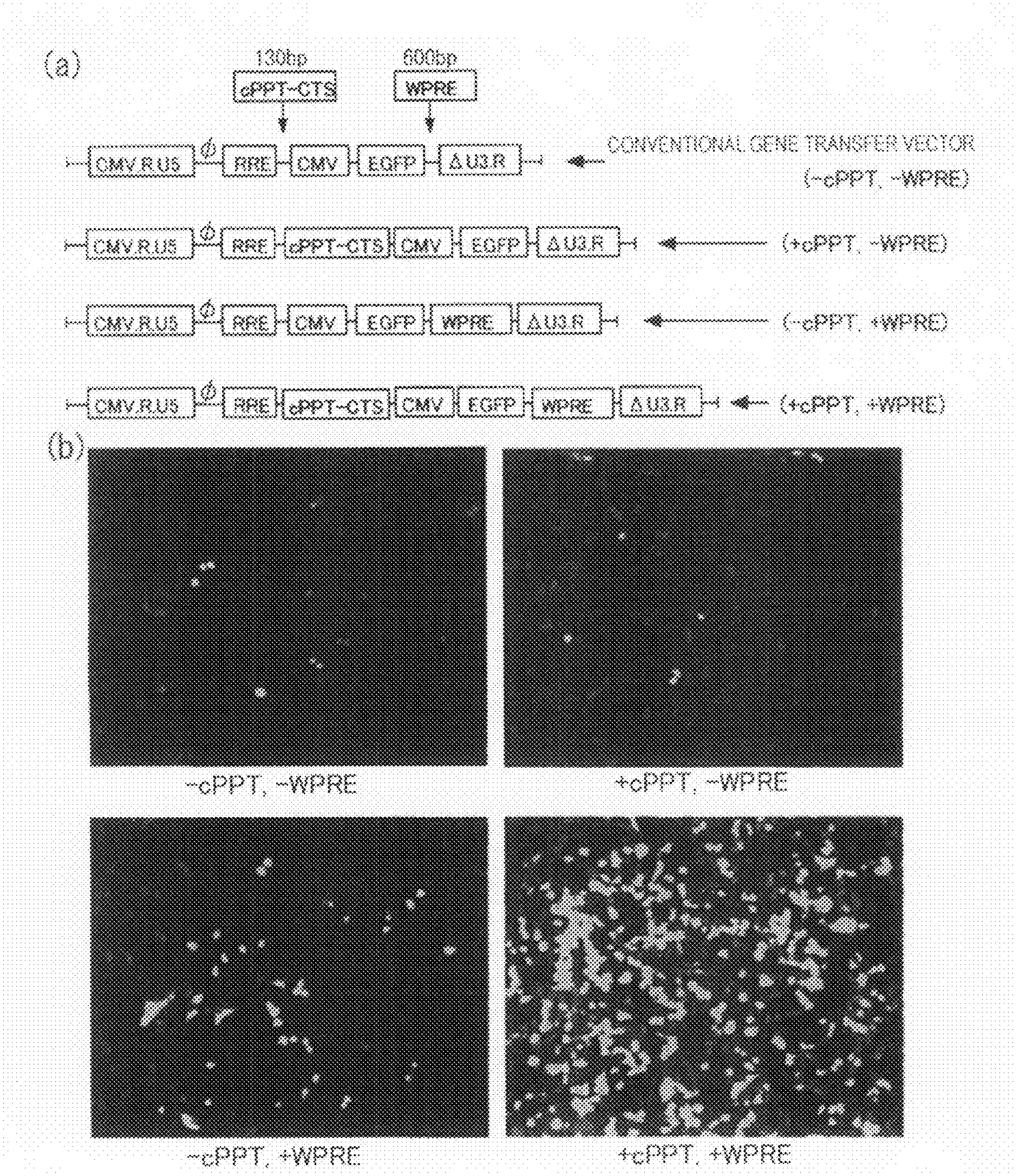
FIG. 5 (*a*) illustrates the structures of conventional gene transfer vectors carrying cPPT alone, WPRE alone, and both cPPT and WPRE. Part (b) is a set of photographs showing the productivity of SIV vectors that is observed when each of the gene transfer vectors carrying cPPT alone, WPRE alone, and both cPPT and WPRE was used for infection of cells at MOI of 15. Upper left: conventional vector without cPPT and WPRE (control) (−cPPT, −WPRE); upper right: vector carrying cPPT alone (+cPPT, −WPRE); lower left: vector carrying WPRE alone (−cPPT, +WPRE); and lower right: vector carrying both cPPT and WPRE (+cPPT, +WPRE).

Four types of vectors were produced: a conventional-type gene transfer vector as a control, vector carrying cPPT alone, vector carrying WPRE alone, and vector carrying both cPPT and WPRE. A schematic diagram of the vector design is shown in FIG. 5-(*a*).

When particle titers of the produced vectors were measured, no difference in productivity of vector particles was shown among the four types. The vectors were transferred into 293T cells at the same MOI based on the number of vector particles (the number of vector particles infected into a single cell), and observed under a fluorescence microscope. As shown in FIG. 5-(*b*), the conventional-type control lacking cPPT and WPRE (−cPPT, and −WPRE) at a MOI of 15 resulted in small number of EGFP-positive cells and weak fluorescence. The vector carrying cPPT alone (+cPPT, −WPRE) increased the number of EGFP-positive cells. For the vector carrying WPRE alone (−cPPT, +WPRE), the number of EGFP-positive cells showed only slight increase as compared to the control, but the fluorescence of the EGFP protein was enhanced. For the vector carrying both cPPT and WPRE (+cPPT, +WPRE), the two factors exhibited synergistic effects and greatly increased both the number of positive cells and fluorescence intensity as compared to the vector carrying cPPT or WPRE alone. The result was much higher than expected.

Figure 6:
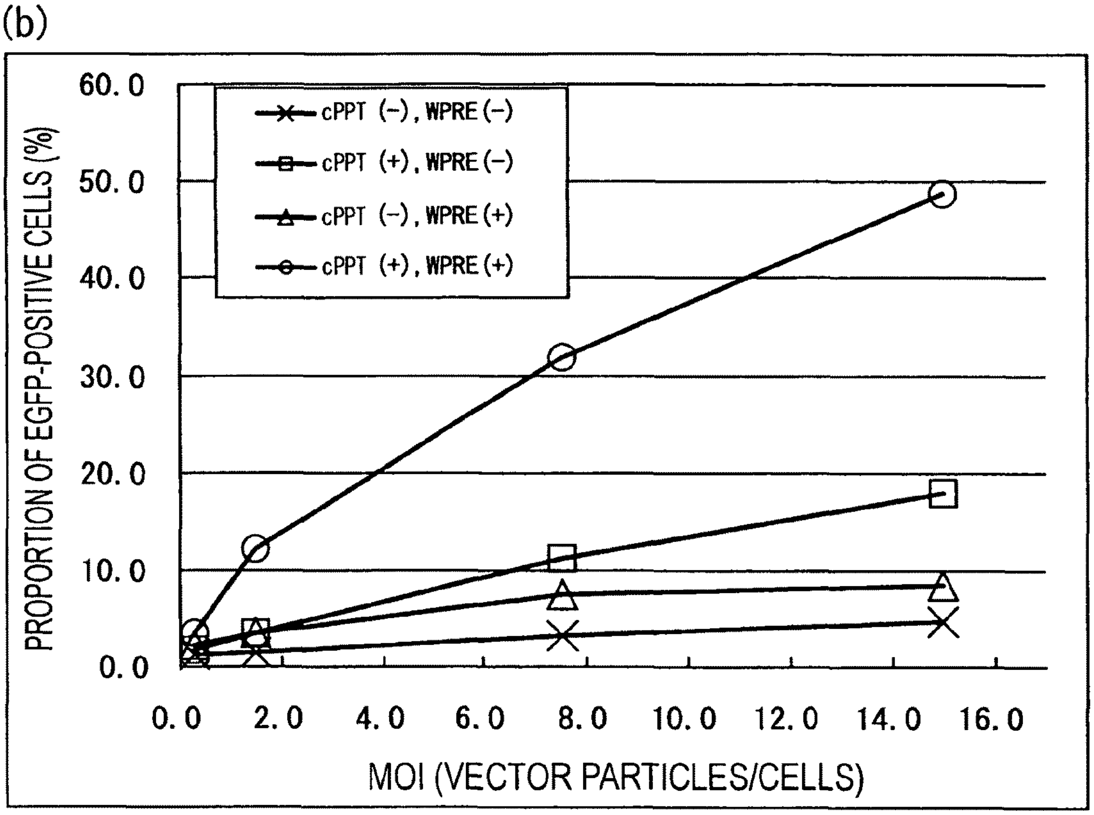
FIG. 6 presents the result of examining the productivity of SIV vectors based on the proportion of the number of foreign gene (EGFP)-positive cells when each of the gene transfer vectors carrying cPPT alone, WPRE alone, and both cPPT and WPRE was used. In part (a), MOI in the table refers to the number of vector particles infected per cell, and 0.3, 1.5, 7.5, and 15 represent the values of MOI (number of vector particles/number of cells) in the infection experiments actually carried out. (+) placed after cPPT or WPRE indicates that cPPT or WPRE is included in the vectors, and (−) indicates that cPPT or WPRE is not included in the vectors. The numbers in the table represent the proportion of EGFP-positive cells (percentage: %). Part (b) presents the values in the table of part (a) as a graph. The vertical axis of the graph indicates the proportion of EGFP-positive cells (percentage: %).

The percentages of EGFP-positive cells examined by FACS (FIG. 6) showed that although all vectors increased the rate of gene transfer in a MOI-dependent manner, the vector carrying both cPPT and WPRE elevated transfer efficiency by approximately ten times as compared to the control. In other words, the substantial functional titer (productivity) was increased ten times.

Figure 7:
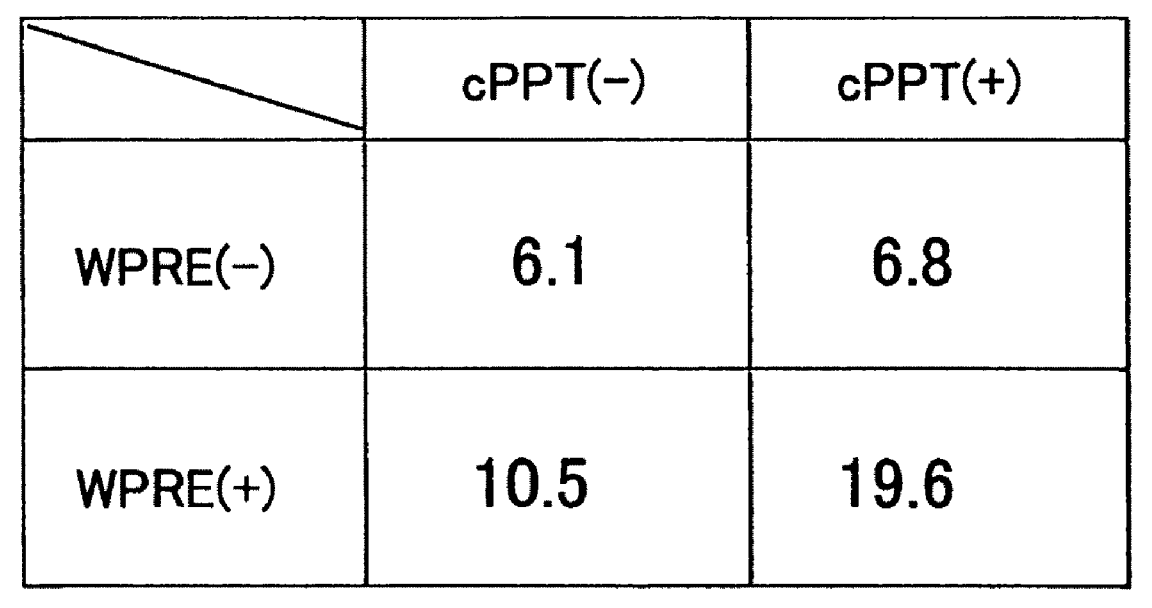

When the average fluorescence intensity of EGFP-positive cells was examined (FIG. 7), the vector carrying both cPPT and WPRE showed significantly higher intensity than the vector carrying WPRE alone, indicating that the protein expression level per cell was also increased by a large amount.

Example 3

Large-Scale Preparation and Concentration of SIV Vectors Carrying Therapeutic Genes An SIV vector was produced as described below based on four types of plasmids shown in FIG. 1: the improved gene transfer vector, packaging vector, rev expression vector, and VSV-G expression vector. The vector carrying the therapeutic gene PEDF was produced in a set of twenty 15-cm dishes.

293T cells were plated in 15-cm plastic dishes at approximately $1\times10^7$ cells per dish (a density to reach 70-80% on the following day) and cultured for 24 hours in 20 mL of D-MEM medium containing 10% fetal calf serum. After culturing the cells for 24 hours, the medium was replaced with 10 mL of OPTI-MEM medium, and the cells were used for transfection. After dissolving 10 μg of a gene transfer vector, 5 μg of packaging vector, 2 μg of rev expression vector, and 2 μg of VSV-G expression vector in 1.5 mL of OPTI-MEM medium per dish, 40 μL of PLUS Reagent (Invitrogen) was added and stirred. Then the mixture was left to stand at room temperature for 15 minutes. After adding 60 μL of LIPOFECTAMINE Reagent diluted in 1.5 mL of OPTI-MEM medium, the mixture was stirred and then left to stand at room temperature for 15 minutes. This DNA complex was added dropwise to the above-mentioned cells in the 15-cm dishes, mixed by gentle shaking, and then incubated for three hours at 37° C. in a 5% $CO_2$ incubator. 13 mL of D-MEM medium containing 20% fetal calf serum was added to the dishes mentioned above, and then the cells were cultured.

On the next day of transfection, the medium was replaced with 30 mL of fresh D-MEM medium containing 10% fetal calf serum, and the cells were cultured. Two days after transfection, the supernatant was collected and 20 mL of fresh medium was added. The collected supernatant was filtered through a 0.45 μm filter, and stored at 4° C. Three days after transfection, the supernatant was collected, filtered through a 0.45 μm filter, combined with the vector collected the day before, and concentrated using a high-speed centrifuge. The collected vector solution was dispensed into sterilized tubes, and centrifuged at 42500 G, 4° C. for one hour. This centrifugation was repeated twice to concentrate the vector solution 500-fold to 1000-fold. The vector was precipitated as a pellet. The pellet was dissolved in PBS containing 5% fetal calf serum. The concentrated vector was divided into small quantities and stored at −80° C. A portion was used to measure the particle titer. Particle titer measurements were performed as in the above-mentioned method.

Example 4

Examination of Therapeutic Effects of SIV-PEDF on Glaucoma Using an Ischemia Reperfusion Model Animal An ischemia reperfusion model was produced as a glaucoma model animal to examine the potential of the SIV-PEDF vector for treating glaucoma. First, a solution ($2.5\times10^7$ TU/mL, TU: transducing units) of the vector of the present invention (SIV-hPEDF) or an empty vector (SIV empty), which does not carry foreign genes, was administered into the subretinal space of 4-week old Wistar strain rats. After 14 days of vector introduction, retinal ganglion cells were injured under ischemic condition for 60 minutes by applying an intraocular pressure of 110 mmHg to the rats. Four days after the injury, fluorescent dye 4',6-diamidino-2-phenylindole (DAPI) was injected into both superior colliculi using a brain stereotaxic apparatus to label the ganglion cells. Seven days after the retinal ganglion cell injury (21 days after the vector introduction), the eyes were removed, prepared as a flat-mount and observed under a fluorescence microscope to measure the number of labeled ganglion cells per $mm^2$ at a site 1 mm from the optic nerve.

As controls, the "vector-unadministered/non-ischemia reperfusion injury group", in which BSS solution instead of the vector solution had been injected into the subretinal space and ischemia reperfusion injury treatment had not been performed, and the "vector-unadministered/ischemia reperfusion injury group", in which BSS solution instead of the vector solution had been administered into the subretinal space and ischemia reperfusion injury treatment had been performed, were also subjected to the same procedures of fluorescent microscopy and measurement of the number of labeled ganglion cells.

Figure 8:
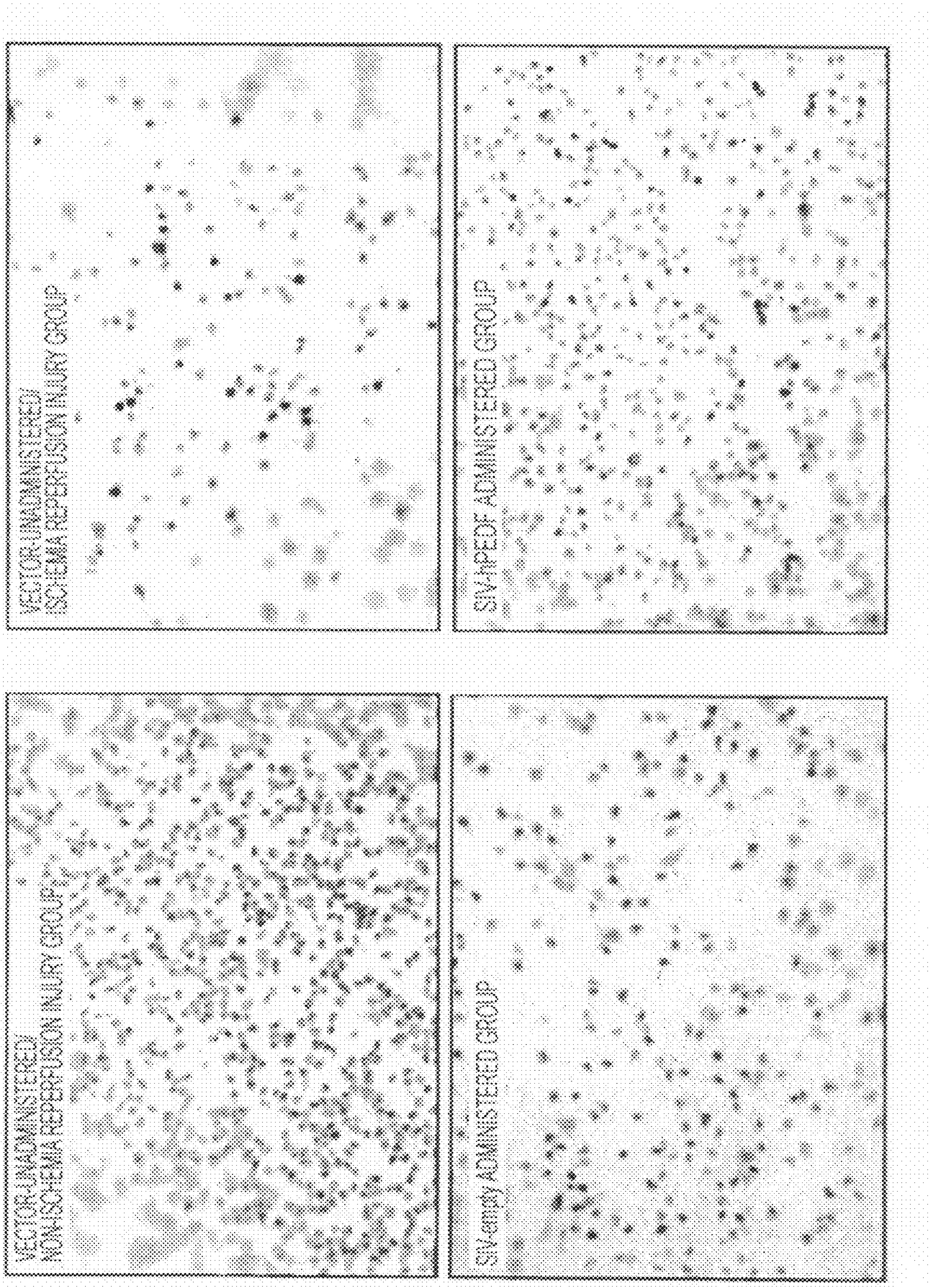
FIG. 8 is a set of photographs depicting the results of observing labeled ganglion cells when an SIV-PEDF vector was administered to the ischemia reperfusion model. Vector-unadministered/non-ischemia reperfusion injury group (rats not subjected to ischemia reperfusion injury treatment nor vector administration); vector-unadministered/ischemia reperfusion injury group (ischemia reperfusion injured rats without vector administration); SIV-empty-administered group (vector control group; ischemia reperfusion injury model rats administered with an empty vector); and SIV-hPEDF-administered group (treated group, ischemia reperfusion injury model rats administered with the SIV-hPEDF vector).
Figure 9:
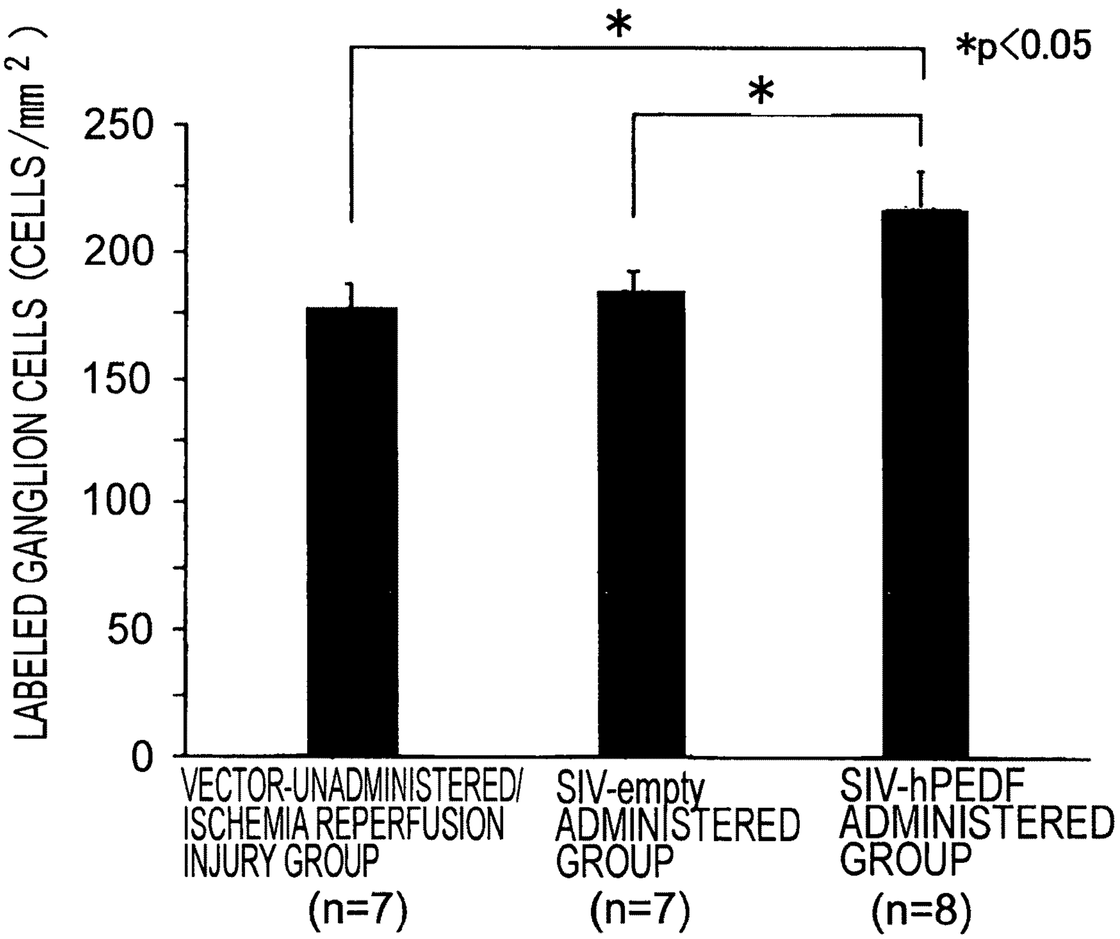
FIG. 9 presents the number of labeled ganglion cells when an SIV-PEDF vector was administered to the ischemia reperfusion model. Vector-unadministered/ischemia reperfusion injury group (ischemia reperfusion injured rats without vector administration); SIV-empty-administered group (vector control group; ischemia reperfusion injury model rats administered with an empty vector); and SIV-hPEDF-administered group (treated group, ischemia reperfusion injury model rats administered with the SIV-hPEDF vector).

Results of fluorescent microscopy are shown in FIG. 8. The numbers of labeled ganglion cells are shown in FIG. 9. The numbers of ganglion cells counted were 177.4/$mm^2$ for the vector-unadministered/ischemia reperfusion injury group, 185.3/$mm^2$ for the SUV-empty-administered group, and 217.8/$mm^2$ for the SIV-hPEDF-administered group. These results revealed the ganglion cell-protecting effect of SIV-hPEDF.

Example 5

Examination of Therapeutic Effects of SIV-PEDF on Glaucoma Using an NMDA-Induced Model An NMDA-induced model was produced as a glaucoma model animal to examine the potential of the SIV-PEDF vector for treating glaucoma. First, a solution ($2.5\times10^7$ TU/mL, TU: transducing units) of the vector SIV-hPEDF of the present invention, or an empty vector SIV-empty, which does not carry foreign genes, was administered into the subretinal space of 4-week old Wistar strain rats. After 14 days of vector introduction, 5 μL of 40 mM NMDA was administered into the vitreous body to selectively injure the ganglion cell layer. Four days after the injury, fluorescent dye 4',6-diamidino-2-phenylindole (DAPI) was injected into both superior colliculi using a brain stereotaxic apparatus to label the ganglion cells. Seven days after the retinal ganglion cell injury (21 days after vector introduction), the eyes were removed, prepared as a flat-mount, and observed under a fluorescence microscope to measure the number of labeled ganglion cells per $mm^2$ at a site 1 mm from the optic nerve.

As controls, the "vector-unadministered/non-NMDA-induced group", in which BSS solution instead of the vector solution had been injected into the subretinal space and NMDA treatment had not been performed, and the "vector-unadministered/NMDA-induced group", in which BSS solution instead of the vector solution had been administered into the subretinal space and NMDA treatment had been performed, were also subjected to the same procedures of fluorescent microscopy and measurement of the number of labeled ganglion cells.

Figure 10:
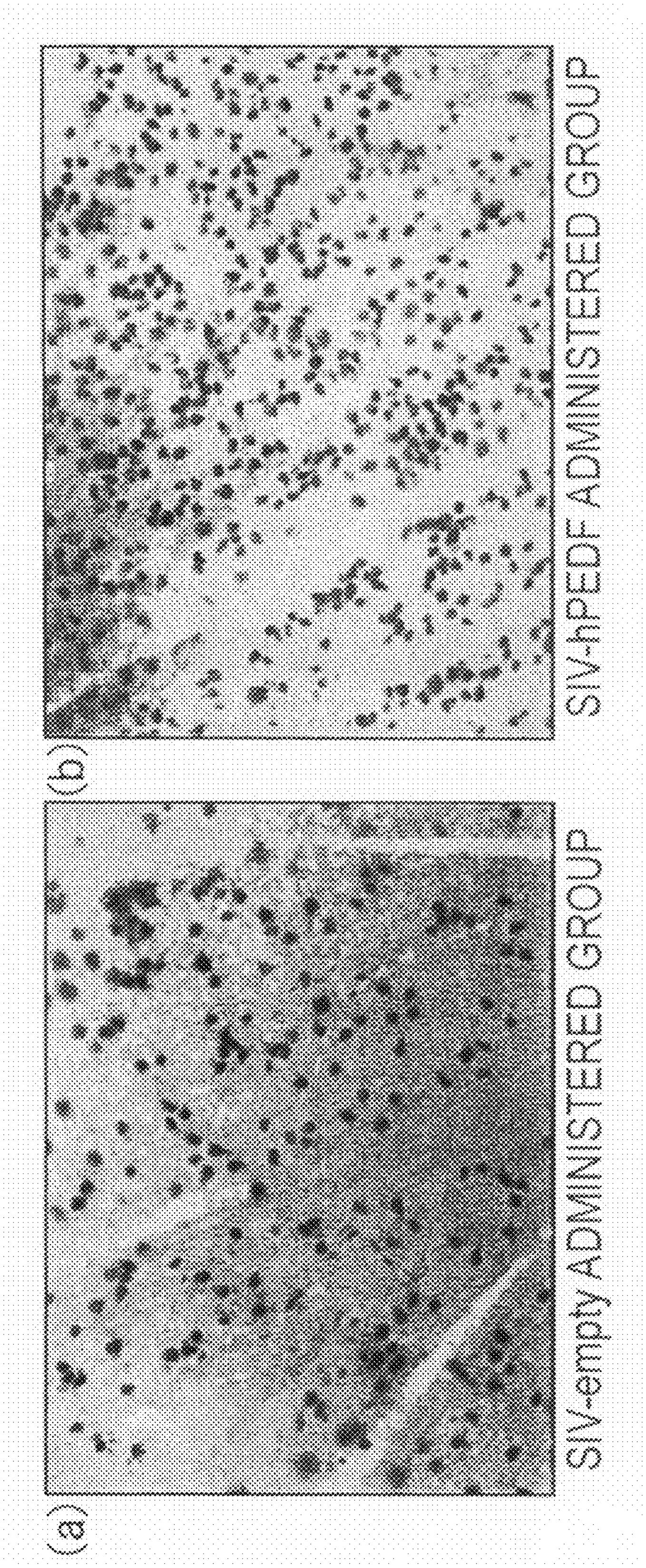
FIG. 10 is a set of photographs depicting the results of observing labeled ganglion cells when an SIV-PEDF vector was administered to the NMDA-induced model: (a) group administered subretinally with an SIV-empty vector; and (b) group administered subretinally with the SIV-hPEDF vector.
Figure 11:
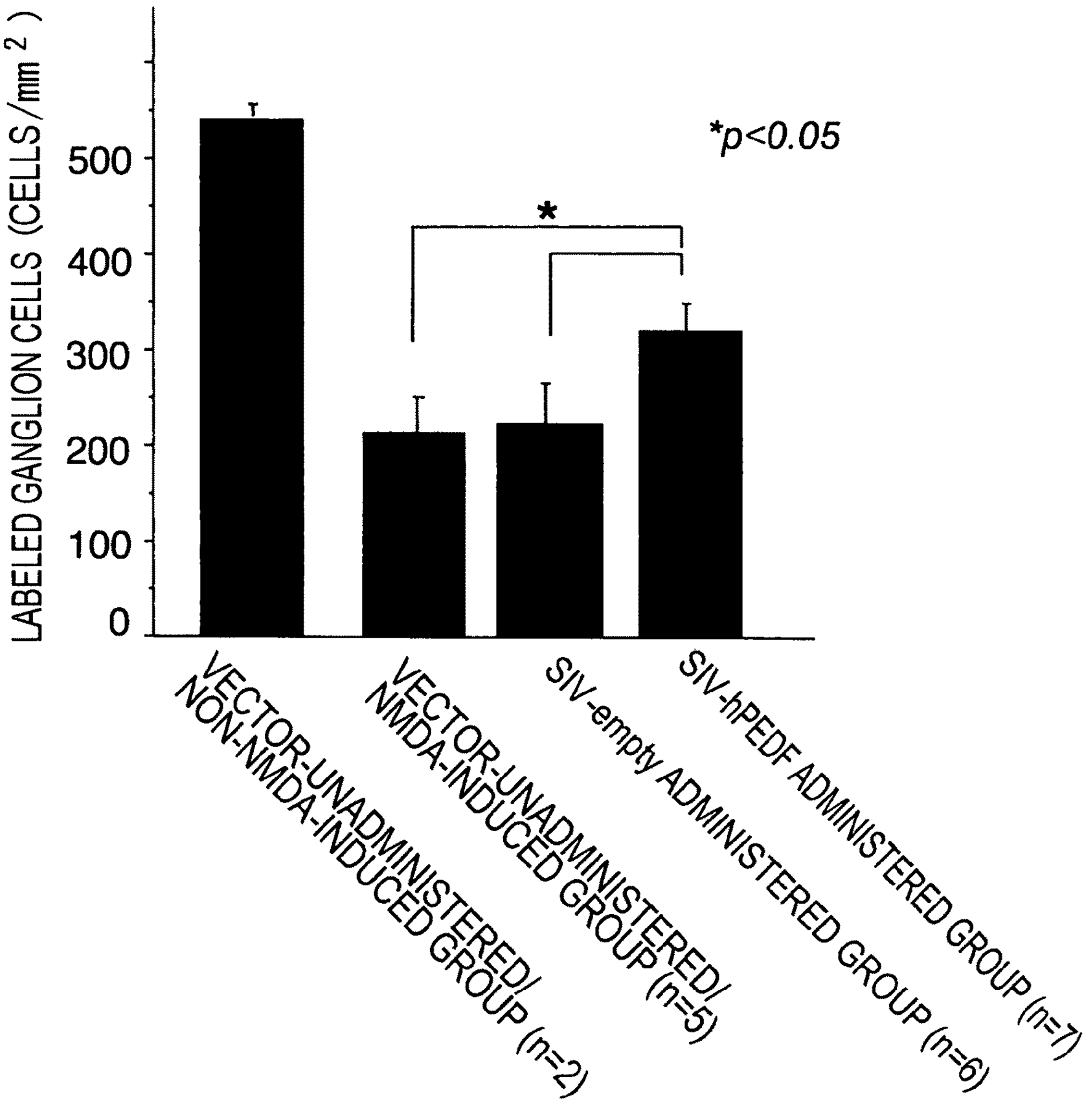
FIG. 11 presents the number of labeled ganglion cells when an SIV-PEDF vector was administered to the NMDA-induced model. Vector-unadministered/non-NMDA-induced group (rats not subjected to NMDA treatment nor vector administration); vector-unadministered/NMDA-induced group (NMDA-induced rats without vector administration); SIV-empty-administered group (vector control group; NMDA-induced model rats administered with an empty vector); and SIV-hPEDF-administered group (treated group, NMDA-induced model rats administered with the SIV-hPEDF vector).

Results of fluorescent microscopy are shown in FIG. 10. The numbers of labeled ganglion cells are shown in FIG. 11. As in the case with the ischemia reperfusion model, the number of ganglion cells counted in the NMDA-induced model also proved the ganglion cell-protecting effect of the SIV-hPEDF vector.

INDUSTRIAL APPLICABILITY

The present invention provides vectors that effectively deliver PEDF to ocular tissue cells. The SIV-PEDF vectors of the present invention afford new therapeutic measures for diseases associated with apoptotic degeneration in ocular tissue cells. More specifically, when the SIV-PEDF vectors of the present invention is administered to patients with diseases associated with apoptotic degeneration in ocular tissue cells, PEDF will be provided continuously in the cells of the patients and able to suppress apoptosis of retinal ganglion cells, the final pathology of glaucoma and such. Considering that most ocular diseases associated with apoptotic degeneration are chronic diseases, SIV-PEDF of the present invention has been proved to be a highly effective pharmaceutical agent for the above-mentioned diseases.

The invention claimed is:

1. A pharmaceutical agent for treating a disease associated with apoptotic degeneration in ocular tissue cells, which comprises a recombinant simian immunodeficiency virus vector encoding a pigment epithelium derived factor (PEDF), and a pharmaceutically acceptable vehicle, wherein said vector is encoded by the nucleotide sequence of SEQ ID NO: 2.

2. The pharmaceutical agent of claim 1, wherein the simian immunodeficiency virus vector is pseudotyped with VSV-G.

3. The pharmaceutical agent of claim 1, wherein the disease associated with apoptotic degeneration in ocular tissue cells is any one of glaucoma, retinitis pigmentosa, retinal detachment, and retinal ischemic disease.

4. A method for producing the pharmaceutical agent of claim 1, said method comprising:

obtaining a recombinant simian immunodeficiency virus vector which is encoded by the nucleotide sequence of SEQ ID NO: 2, and adding a pharmaceutically acceptable vehicle to said vector to produce the pharmaceutical agent.

5. The method of claim 4, wherein the recombinant simian immunodeficiency virus vector is produced by introducing a vector comprising the nucleotide sequence of SEQ ID NO: 2 into a packaging cell line into which a packaging vector comprising the nucleotide sequence of SEQ ID NO: 3 has been introduced.

6. A vector encoding a simian immunodeficiency virus genomic RNA, which comprises the nucleotide sequence of SEQ ID NO: 2.

7. A simian immunodeficiency virus genomic RNA encoded by the vector of claim 6.

* * * * *

SEQUENCE LISTING

<160> NUMBER OF SEQ ID NOS: 35

<210> SEQ ID NO 1
<211> LENGTH: 7062
<212> TYPE: DNA
<213> ORGANISM: Artificial
<220> FEATURE:
<223> OTHER INFORMATION: an artificially synthesized vector sequence

<400> SEQUENCE: 1
ggtacctcaa tattggccat tagccatatt attcattggt tatatagcat aaatcaatat 60
tggctattgg ccattgcata cgttgtatct atatcataat atgtacattt atattggctc 120
atgtccaata tgaccgccat gttggcattg attattgact agttattaat agtaatcaat 180
tacggggtca ttagttcata gcccatatat ggagttccgc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtccgcccc ctattgacgt 420
caatgacggt aaatggcccg cctggcatta tgcccagtac atgaccttac gggactttcc 480
tacttggcag tacatctacg tattagtcat cgctattacc atggtgatgc ggttttggca 540
gtacaccaat gggcgtggat agcggtttga ctcacgggga tttccaagtc tccaccccat 600
tgacgtcaat gggagtttgt tttggcacca aaatcaacgg gactttccaa aatgtcgtaa 660
caactgcgat cgcccgcccc gttgacgcaa atgggcggta ggcgtgtacg gtgggaggtc 720
tatataagca gagctcgctg gcttgtaact cagtctctta ctaggagacc agcttgagcc 780
tgggtgttcg ctggttagcc taacctggtt ggccaccagg ggtaaggact ccttggctta 840
gaaagctaat aaacttgcct gcattagagc ttatctgagt caagtgtcct cattgacgcc 900
tcactctctt gaacgggaat cttccttact gggttctctc tctgacccag gcgagagaaa 960
ctccagcagt ggcgcccgaa cagggacttg agtgagagtg taggcacgta cagctgagaa 1020
ggcgtcggac gcgaaggaag cgcggggtgc gacgcgacca agaaggagac ttggtgagta 1080
ggcttctcga gtgccgggaa aaagctcgag cctagttaga ggactaggag aggccgtagc 1140
cgtaactact ctgggcaagt agggcaggcg gtgggtacgc aatgggggcg gctacctcag 1200
cactaaatag gagacaatta gaccaatttg agaaaatacg acttcgcccg aacggaaaga 1260
aaaagtacca aattaaacat ttaatatggg caggcaagga gatggagcgc ttcggcctcc 1320
atgagaggtt gttggagaca gaggaggggt gtaaaagaat catagaagtc ctctaccccc 1380
tagaaccaac aggatcggag ggcttaaaaa gtctgttcaa tcttgtgtgc gtgctatatt 1440
gcttgcacaa ggaacagaaa gtgaaagaca cagaggaagc agtagcaaca gtaagacaac 1500
actgccatct agtggaaaaa gaaaaaagtg caacagagac atctagtgga caaaagaaaa 1560
atgacaaggg aatagcagcg ccacctggtg gcagtcagaa ttttccagcg caacaacaag 1620
gaaatgcctg ggtacatgta cccttgtcac cgcgcacctt aaatgcgtgg gtaaaagcag 1680
tagaggagaa aaaatttgga gcagaaatag tacccatgtt tcaagcccta tcgaattccc 1740
gtttgtgcta gggttcttag gcttcttggg ggctgctgga actgcaatgg gagcagcggc 1800
gacagccctg acggtccagt ctcagcattt gcttgctggg atactgcagc agcagaagaa 1860
tctgctggcg gctgtggagg ctcaacagca gatgttgaag ctgaccattt ggggtgttaa 1920
aaacctcaat gcccgcgtca cagcccttga gaagtaccta gaggatcagg cacgactaaa 1980

-continued

```
ctcctggggg tgcgcatgga aacaagtatg tcataccaca gtggagtggc cctggacaaa   2040

tcggactccg gattggcaaa atatgacttg gttggagtgg gaaagacaaa tagctgattt   2100

ggaaagcaac attacgagac aattagtgaa ggctagagaa caagaggaaa agaatctaga   2160

tgcctatcag aagttaacta gttggtcaga tttctggtct tggttcgatt tctcaaaatg   2220

gcttaacatt ttaaaaatgg gatttttagt aatagtagga ataatagggt taagattact   2280

ttacacagta tatggatgta tagtgagggt taggcaggga tatgttcctc tatctccaca   2340

gatccatatc cgcggcaatt ttaaaagaaa gggaggaata gggggacaga cttcagcaga   2400

gagactaatt aatataataa caacacaatt agaaatacaa catttacaaa ccaaaattca   2460

aaaaatttta aattttagag ccgcggtagt tattaatagt aatcaattac ggggtcatta   2520

gttcatagcc catatatgga gttccgcgtt acataactta cggtaaatgg cccgcctggc   2580

tgaccgccca acgacccccg cccattgacg tcaataatga cgtatgttcc catagtaacg   2640

ccaataggga ctttccattg acgtcaatgg gtggagtatt tacggtaaac tgcccacttg   2700

gcagtacatc aagtgtatca tatgccaagt acgcccccta ttgacgtcaa tgacggtaaa   2760

tggcccgcct ggcattatgc ccagtacatg accttatggg actttcctac ttggcagtac   2820

atctacgtat tagtcatcgc tattaccatg gtgatgcggt tttggcagta catcaatggg   2880

cgtggatagc ggtttgactc acggggattt ccaagtctcc accccattga cgtcaatggg   2940

agtttgtttt ggcaccaaaa tcaacgggac tttccaaaat gtcgtaacaa ctccgcccca   3000

ttgacgcaaa tgggcggtag gcgtgtacgg tgggaggtct atataagcag agctggttta   3060

gtgaaccgtc agatccagcg gccgcaagct tggatcctta agttaatcaa cctctggatt   3120

acaaaatttg tgaaagattg actggtattc ttaactatgt tgctcctttt acgctatgtg   3180

gatacgctgc tttaatgcct ttgtatcatg ctattgcttc ccgtatggct ttcattttct   3240

cctccttgta taaatcctgg ttgctgtctc tttatgagga gttgtggccc gttgtcaggc   3300

aacgtggcgt ggtgtgcact gtgtttgctg acgcaacccc cactggttgg ggcattgcca   3360

ccacctgtca gctcctttcc gggactttcg ctttccccct ccctattgcc acggcggaac   3420

tcatcgccgc ctgccttgcc cgctgctgga caggggctcg gctgttgggc actgacaatt   3480

ccgtggtgtt gtcggggaaa tcatcgtcct ttccttggct gctcgcctgt gttgccacct   3540

ggattctgcg cgggacgtcc ttctgctacg tcccttcggc cctcaatcca gcggaccttc   3600

cttcccgcgg cctgctgccg gctctgcggc ctcttccgcg tcttcgcctt cgccctcaga   3660

cgagtcggat ctccctttgg gccgcctccc cgcagatccg cactttttaa aagaaaaggg   3720

aggactggat gggatttatt actccgatag gacgctggct tgtaactcag tctcttacta   3780

ggagaccagc ttgagcctgg gtgttcgctg gttagcctaa cctggttggc caccaggggt   3840

aaggactcct tggcttagaa agctaataaa cttgcctgca ttagagctct tacgcgtgct   3900

agcccgggct cgagatccgc atctcaatta gtcagcaacc atagtcccgc ccctaactcc   3960

gcccatcccg cccctaactc cgcccagttc cgcccattct ccgccccatg gctgactaat   4020

ttttttattt tatgcagagg ccgaggccgc ctcggcctct gagctattcc agaagtagtg   4080

aggaggcttt tttggaggcc taggcttttg caaaaagcta acttgtttat tgcagcttat   4140

aatggttaca aataaagcaa tagcatcaca aatttcacaa ataaagcatt tttttcactg   4200

cattctagtt gtggtttgtc caaactcatc aatgtatctt atcatgtctg tcgaccgatg   4260

cccttgagag ccttcaaccc agtcagctcc ttccggtggg cgcggggcat gactatcgtc   4320

gccgcactta tgactgtctt ctttatcatg caactcgtag gacaggtgcc ggcagcgctc   4380
```

-continued

```
ttccgcttcc tcgctcactg actcgctgcg ctcggtcgtt cggctgcggc gagcggtatc   4440
agctcactca aaggcggtaa tacggttatc cacagaatca ggggataacg caggaaagaa   4500
catgtgagca aaaggccagc aaaaggccag gaaccgtaaa aaggccgcgt tgctggcgtt   4560
tttccatagg ctccgccccc ctgacgagca tcacaaaaat cgacgctcaa gtcagaggtg   4620
gcgaaacccg acaggactat aaagatacca ggcgtttccc cctggaagct ccctcgtgcg   4680
ctctcctgtt ccgaccctgc cgcttaccgg atacctgtcc gcctttctcc cttcgggaag   4740
cgtggcgctt tctcaatgct cacgctgtag gtatctcagt tcggtgtagg tcgttcgctc   4800
caagctgggc tgtgtgcacg aaccccccgt tcagcccgac cgctgcgcct tatccggtaa   4860
ctatcgtctt gagtccaacc cggtaagaca cgacttatcg ccactggcag cagccactgg   4920
taacaggatt agcagagcga ggtatgtagg cggtgctaca gagttcttga agtggtggcc   4980
taactacggc tacactagaa ggacagtatt tggtatctgc gctctgctga agccagttac   5040
cttcggaaaa agagttggta gctcttgatc cggcaaacaa accaccgctg gtagcggtgg   5100
tttttttgtt tgcaagcagc agattacgcg cagaaaaaaa ggatctcaag aagatccttt   5160
gatcttttct acggggtctg acgctcagtg gaacgaaaac tcacgttaag ggattttggt   5220
catgagatta tcaaaaagga tcttcaccta gatcctttta aattaaaaat gaagttttaa   5280
atcaatctaa agtatatatg agtaaacttg gtctgacagt taccaatgct taatcagtga   5340
ggcacctatc tcagcgatct gtctatttcg ttcatccata gttgcctgac tccccgtcgt   5400
gtagataact acgatacggg agggcttacc atctggcccc agtgctgcaa tgataccgcg   5460
agacccacgc tcaccggctc cagatttatc agcaataaac cagccagccg gaagggccga   5520
gcgcagaagt ggtcctgcaa ctttatccgc ctccatccag tctattaatt gttgccggga   5580
agctagagta agtagttcgc cagttaatag tttgcgcaac gttgttgcca ttgctacagg   5640
catcgtggtg tcacgctcgt cgtttggtat ggcttcattc agctccggtt cccaacgatc   5700
aaggcgagtt acatgatccc ccatgttgtg caaaaaagcg gttagctcct tcggtcctcc   5760
gatcgttgtc agaagtaagt tggccgcagt gttatcactc atggttatgg cagcactgca   5820
taattctctt actgtcatgc catccgtaag atgcttttct gtgactggtg agtactcaac   5880
caagtcattc tgagaatagt gtatgcggcg accgagttgc tcttgcccgg cgtcaatacg   5940
ggataatacc gcgccacata gcagaacttt aaaagtgctc atcattggaa aacgttcttc   6000
ggggcgaaaa ctctcaagga tcttaccgct gttgagatcc agttcgatgt aacccactcg   6060
tgcacccaac tgatcttcag catcttttac tttcaccagc gtttctgggt gagcaaaaac   6120
aggaaggcaa aatgccgcaa aaaagggaat aagggcgaca cggaaatgtt gaatactcat   6180
actcttcctt tttcaatatt attgaagcat ttatcagggt tattgtctca tgagcggata   6240
catatttgaa tgtatttaga aaaataaaca aataggggtt ccgcgcacat ttccccgaaa   6300
agtgccacct gacgcgccct gtagcggcgc attaagcgcg gcgggtgtgg tggttacgcg   6360
cagcgtgacc gctacacttg ccagcgccct agcgcccgct cctttcgctt tcttcccttc   6420
ctttctcgcc acgttcgccg gctttccccg tcaagctcta aatcgggggc tccctttagg   6480
gttccgattt agtgctttac ggcacctcga ccccaaaaaa cttgattagg gtgatggttc   6540
acgtagtggg ccatcgccct gatagacggt ttttcgccct ttgacgttgg agtccacgtt   6600
ctttaatagt ggactcttgt tccaaactgg aacaacactc aaccctatct cggtctattc   6660
ttttgattta taagggattt tgccgatttc ggcctattgg ttaaaaaatg agctgattta   6720
acaaaaattt aacgcgaatt ttaacaaaat attaacgttt acaatttccc attcgccatt   6780
```

-continued

```
caggctgcgc aactgttggg aagggcgatc ggtgcgggcc tcttcgctat tacgccagcc   6840

caagctacca tgataagtaa gtaatattaa ggtacgggag gtacttggag cggccggccg   6900

caataaaata tctttatttt cattacatct gtgtgttggt tttttgtgtg aatcgatagt   6960

actaacatac gctctccatc aaaacaaaac gaaacaaaac aaactagcaa aataggctgt   7020

ccccagtgca agtgcaggtg ccagaacatt tctctatcga ta                      7062
```

<210> SEQ ID NO 2
<211> LENGTH: 8363
<212> TYPE: DNA
<213> ORGANISM: Artificial
<220> FEATURE:
<223> OTHER INFORMATION: an artificially synthesized vector sequence

<400> SEQUENCE: 2

```
ggtacctcaa tattggccat tagccatatt attcattggt tatatagcat aaatcaatat     60

tggctattgg ccattgcata cgttgtatct atatcataat atgtacattt atattggctc    120

atgtccaata tgaccgccat gttggcattg attattgact agttattaat agtaatcaat    180

tacggggtca ttagttcata gcccatatat ggagttccgc gttacataac ttacggtaaa    240

tggcccgcct ggctgaccgc ccaacgaccc ccgcccattg acgtcaataa tgacgtatgt    300

tcccatagta acgccaatag ggactttcca ttgacgtcaa tgggtggagt atttacggta    360

aactgcccac ttggcagtac atcaagtgta tcatatgcca agtccgcccc ctattgacgt    420

caatgacggt aaatggcccg cctggcatta tgcccagtac atgaccttac gggactttcc    480

tacttggcag tacatctacg tattagtcat cgctattacc atggtgatgc ggttttggca    540

gtacaccaat gggcgtggat agcggtttga ctcacgggga tttccaagtc tccaccccat    600

tgacgtcaat gggagtttgt tttggcacca aaatcaacgg gactttccaa aatgtcgtaa    660

caactgcgat cgcccgcccc gttgacgcaa atgggcggta ggcgtgtacg gtgggaggtc    720

tatataagca gagctcgctg gcttgtaact cagtctctta ctaggagacc agcttgagcc    780

tgggtgttcg ctggttagcc taacctggtt ggccaccagg ggtaaggact ccttggctta    840

gaaagctaat aaacttgcct gcattagagc ttatctgagt caagtgtcct cattgacgcc    900

tcactctctt gaacgggaat cttccttact gggttctctc tctgacccag gcgagagaaa    960

ctccagcagt ggcgcccgaa cagggacttg agtgagagtg taggcacgta cagctgagaa   1020

ggcgtcggac gcgaaggaag cgcggggtgc gacgcgacca agaaggagac ttggtgagta   1080

ggcttctcga gtgccgggaa aaagctcgag cctagttaga ggactaggag aggccgtagc   1140

cgtaactact ctgggcaagt agggcaggcg gtgggtacgc aatgggggcg gctacctcag   1200

cactaaatag gagacaatta gaccaatttg agaaaatacg acttcgcccg aacggaaaga   1260

aaaagtacca aattaaacat ttaatatggg caggcaagga gatggagcgc ttcggcctcc   1320

atgagaggtt gttggagaca gaggaggggt gtaaaagaat catagaagtc ctctaccccc   1380

tagaaccaac aggatcggag ggcttaaaaa gtctgttcaa tcttgtgtgc gtgctatatt   1440

gcttgcacaa ggaacagaaa gtgaaagaca cagaggaagc agtagcaaca gtaagacaac   1500

actgccatct agtggaaaaa gaaaaaagtg caacagagac atctagtgga caaaagaaaa   1560

atgacaaggg aatagcagcg ccacctggtg gcagtcagaa ttttccagcg caacaacaag   1620

gaaatgcctg ggtacatgta cccttgtcac cgcgcacctt aaatgcgtgg gtaaaagcag   1680

tagaggagaa aaaatttgga gcagaaatag tacccatgtt tcaagcccta tcgaattccc   1740

gtttgtgcta gggttcttag gcttcttggg ggctgctgga actgcaatgg gagcagcggc   1800
```

-continued

```
gacagccctg acggtccagt ctcagcattt gcttgctggg atactgcagc agcagaagaa   1860
tctgctggcg gctgtggagg ctcaacagca gatgttgaag ctgaccattt ggggtgttaa   1920
aaacctcaat gcccgcgtca cagcccttga gaagtaccta gaggatcagg cacgactaaa   1980
ctcctggggg tgcgcatgga aacaagtatg tcataccaca gtggagtggc cctggacaaa   2040
tcggactccg gattggcaaa atatgacttg gttggagtgg gaaagacaaa tagctgattt   2100
ggaaagcaac attacgagac aattagtgaa ggctagagaa caagaggaaa agaatctaga   2160
tgcctatcag aagttaacta gttggtcaga tttctggtct tggttcgatt tctcaaaatg   2220
gcttaacatt ttaaaaatgg gatttttagt aatagtagga ataatagggt taagattact   2280
ttacacagta tatggatgta tagtgagggt taggcaggga tatgttcctc tatctccaca   2340
gatccatatc cgcggcaatt ttaaaagaaa gggaggaata gggggacaga cttcagcaga   2400
gagactaatt aatataataa caacacaatt agaaatacaa catttacaaa ccaaaattca   2460
aaaaatttta aattttagag ccgcggtagt tattaatagt aatcaattac ggggtcatta   2520
gttcatagcc catatatgga gttccgcgtt acataactta cggtaaatgg cccgcctggc   2580
tgaccgccca acgacccccg cccattgacg tcaataatga cgtatgttcc catagtaacg   2640
ccaataggga ctttccattg acgtcaatgg gtggagtatt tacggtaaac tgcccacttg   2700
gcagtacatc aagtgtatca tatgccaagt acgcccccta ttgacgtcaa tgacggtaaa   2760
tggcccgcct ggcattatgc ccagtacatg accttatggg actttcctac ttggcagtac   2820
atctacgtat tagtcatcgc tattaccatg gtgatgcggt tttggcagta catcaatggg   2880
cgtggatagc ggtttgactc acggggattt ccaagtctcc accccattga cgtcaatggg   2940
agtttgtttt ggcaccaaaa tcaacgggac tttccaaaat gtcgtaacaa ctccgcccca   3000
ttgacgcaaa tgggcggtag gcgtgtacgg tgggaggtct atataagcag agctggttta   3060
gtgaaccgtc agatccagcg gccgcgaatt cactagtgat taggatgcag gccctggtgc   3120
tactcctctg cattggagcc ctcctcgggc acagcagctg ccagaaccct gccagccccc   3180
cggaggaggg ctccccagac cccgacagca caggggcgct ggtggaggag gaggatcctt   3240
tcttcaaagt ccccgtgaac aagctggcag cggctgtctc caacttcggc tatgacctgt   3300
accgggtgcg atccagcatg agccccacga ccaacgtgct cctgtctcct ctcagtgtgg   3360
ccacggccct ctcggccctc tcgctgggag cggagcagcg aacagaatcc atcattcacc   3420
gggctctcta ctatgacttg atcagcagcc cagacatcca tggtacctat aaggagctcc   3480
ttgacacggt cactgccccc cagaagaacc tcaagagtgc ctcccggatc gtctttgaga   3540
agaagctgcg cataaaatcc agctttgtgg cacctctgga aaagtcatat gggaccaggc   3600
ccagagtcct gacgggcaac cctcgcttgg acctgcaaga gatcaacaac tgggtgcagg   3660
cgcagatgaa agggaagctc gccaggtcca caaaggaaat tcccgatgag atcagcattc   3720
tccttctcgg tgtggcgcac ttcaaggggc agtgggtaac aaagtttgac tccagaaaga   3780
cttccctcga ggatttctac ttggatgaag agaggaccgt gagggtcccc atgatgtcgg   3840
accctaaggc tgttttacgc tatggcttgg attcagatct cagctgcaag attgcccagc   3900
tgcccttgac cggaagcatg agtatcatct tcttcctgcc cctgaaagtg acccagaatt   3960
tgaccttgat agaggagagc ctcacctccg agttcattca tgacatagac cgagaactga   4020
agaccgtgca ggcggtcctc actgtcccca agctgaagct gagttacgaa ggcgaagtca   4080
ccaagtccct gcaggagatg aagctgcaat ccttgtttga ttcaccagac tttagcaaga   4140
tcacaggcaa acccatcaag ctgactcagg tggaacaccg ggctggcttt gagtggaacg   4200
```

-continued

```
aggatggggc gggaaccacc cccagcccag ggctgcagcc tgcccacctc accttcccgc   4260
tggactatca ccttaaccag cctttcatct tcgtactgag ggacacagac acaggggccc   4320
ttctcttcat tggcaagatt ctggacccca ggggccccta atataaaatc gaattcccgc   4380
ggccgcaagc ttggatcctt aagttaatca acctctggat tacaaaattt gtgaaagatt   4440
gactggtatt cttaactatg ttgctccttt tacgctatgt ggatacgctg ctttaatgcc   4500
tttgtatcat gctattgctt cccgtatggc tttcattttc tcctccttgt ataaatcctg   4560
gttgctgtct ctttatgagg agttgtggcc cgttgtcagg caacgtggcg tggtgtgcac   4620
tgtgtttgct gacgcaaccc ccactggttg gggcattgcc accacctgtc agctcctttc   4680
cgggactttc gctttccccc tccctattgc cacggcggaa ctcatcgccg cctgccttgc   4740
ccgctgctgg acaggggctc ggctgttggg cactgacaat tccgtggtgt tgtcggggaa   4800
atcatcgtcc tttccttggc tgctcgcctg tgttgccacc tggattctgc gcgggacgtc   4860
cttctgctac gtcccttcgg ccctcaatcc agcggacctt ccttcccgcg gcctgctgcc   4920
ggctctgcgg cctcttccgc gtcttcgcct tcgccctcag acgagtcgga tctccctttg   4980
ggccgcctcc ccgcagatcc gcactttttta aaagaaaagg gaggactgga tgggatttat   5040
tactccgata ggacgctggc ttgtaactca gtctcttact aggagaccag cttgagcctg   5100
ggtgttcgct ggttagccta acctggttgg ccaccagggg taaggactcc ttggcttaga   5160
aagctaataa acttgcctgc attagagctc ttacgcgtgc tagcccgggc tcgagatccg   5220
catctcaatt agtcagcaac catagtcccg cccctaactc cgcccatccc gcccctaact   5280
ccgcccagtt ccgcccattc tccgccccat ggctgactaa ttttttttat ttatgcagag   5340
gccgaggccg cctcggcctc tgagctattc cagaagtagt gaggaggctt ttttggaggc   5400
ctaggctttt gcaaaaagct aacttgttta ttgcagctta taatggttac aaataaagca   5460
atagcatcac aaatttcaca aataaagcat ttttttcact gcattctagt tgtggtttgt   5520
ccaaactcat caatgtatct tatcatgtct gtcgaccgat gcccttgaga gccttcaacc   5580
cagtcagctc cttccggtgg gcgcggggca tgactatcgt cgccgcactt atgactgtct   5640
tctttatcat gcaactcgta ggacaggtgc cggcagcgct cttccgcttc ctcgctcact   5700
gactcgctgc gctcggtcgt tcggctgcgg cgagcggtat cagctcactc aaaggcggta   5760
atacggttat ccacagaatc aggggataac gcaggaaaga acatgtgagc aaaaggccag   5820
caaaaggcca ggaaccgtaa aaaggccgcg ttgctggcgt ttttccatag gctccgcccc   5880
cctgacgagc atcacaaaaa tcgacgctca agtcagaggt ggcgaaaccc gacaggacta   5940
taaagatacc aggcgtttcc ccctggaagc tccctcgtgc gctctcctgt tccgaccctg   6000
ccgcttaccg gatacctgtc cgcctttctc ccttcgggaa gcgtggcgct ttctcaatgc   6060
tcacgctgta ggtatctcag ttcggtgtag gtcgttcgct ccaagctggg ctgtgtgcac   6120
gaaccccccg ttcagcccga ccgctgcgcc ttatccggta actatcgtct tgagtccaac   6180
ccggtaagac acgacttatc gccactggca gcagccactg gtaacaggat tagcagagcg   6240
aggtatgtag gcggtgctac agagttcttg aagtggtggc ctaactacgg ctacactaga   6300
aggacagtat ttggtatctg cgctctgctg aagccagtta ccttcggaaa aagagttggt   6360
agctcttgat ccggcaaaca aaccaccgct ggtagcggtg gtttttttgt ttgcaagcag   6420
cagattacgc gcagaaaaaa aggatctcaa gaagatcctt tgatcttttc tacggggtct   6480
gacgctcagt ggaacgaaaa ctcacgttaa gggattttgg tcatgagatt atcaaaaagg   6540
atcttcacct agatcctttt aaattaaaaa tgaagtttta aatcaatcta aagtatatat   6600
```

-continued gagtaaactt ggtctgacag ttaccaatgc ttaatcagtg aggcacctat ctcagcgatc 6660
tgtctatttc gttcatccat agttgcctga ctccccgtcg tgtagataac tacgatacgg 6720
gagggcttac catctggccc cagtgctgca atgataccgc gagacccacg ctcaccggct 6780
ccagatttat cagcaataaa ccagccagcc ggaagggccg agcgcagaag tggtcctgca 6840
actttatccg cctccatcca gtctattaat tgttgccggg aagctagagt aagtagttcg 6900
ccagttaata gtttgcgcaa cgttgttgcc attgctacag gcatcgtggt gtcacgctcg 6960
tcgtttggta tggcttcatt cagctccggt tcccaacgat caaggcgagt tacatgatcc 7020
cccatgttgt gcaaaaaagc ggttagctcc ttcggtcctc cgatcgttgt cagaagtaag 7080
ttggccgcag tgttatcact catggttatg gcagcactgc ataattctct tactgtcatg 7140
ccatccgtaa gatgcttttc tgtgactggt gagtactcaa ccaagtcatt ctgagaatag 7200
tgtatgcggc gaccgagttg ctcttgcccg gcgtcaatac gggataatac cgcgccacat 7260
agcagaactt taaaagtgct catcattgga aaacgttctt cggggcgaaa actctcaagg 7320
atcttaccgc tgttgagatc cagttcgatg taacccactc gtgcacccaa ctgatcttca 7380
gcatctttta ctttcaccag cgtttctggg tgagcaaaaa caggaaggca aaatgccgca 7440
aaaaagggaa taagggcgac acggaaatgt tgaatactca tactcttcct ttttcaatat 7500
tattgaagca tttatcaggg ttattgtctc atgagcggat acatatttga atgtatttag 7560
aaaaataaac aaataggggt tccgcgcaca tttccccgaa aagtgccacc tgacgcgccc 7620
tgtagcggcg cattaagcgc ggcgggtgtg gtggttacgc gcagcgtgac cgctacactt 7680
gccagcgccc tagcgcccgc tcctttcgct ttcttccctt cctttctcgc cacgttcgcc 7740
ggctttcccc gtcaagctct aaatcggggg ctccctttag ggttccgatt tagtgcttta 7800
cggcacctcg accccaaaaa acttgattag ggtgatggtt cacgtagtgg gccatcgccc 7860
tgatagacgg tttttcgccc tttgacgttg gagtccacgt tctttaatag tggactcttg 7920
ttccaaactg gaacaacact caaccctatc tcggtctatt cttttgattt ataagggatt 7980
ttgccgattt cggcctattg gttaaaaaat gagctgattt aacaaaaatt taacgcgaat 8040
tttaacaaaa tattaacgtt tacaatttcc cattcgccat tcaggctgcg caactgttgg 8100
gaagggcgat cggtgcgggc ctcttcgcta ttacgccagc ccaagctacc atgataagta 8160
agtaatatta aggtacggga ggtacttgga gcggccggcc gcaataaaat atctttattt 8220
tcattacatc tgtgtgttgg tttttgtgt gaatcgatag tactaacata cgctctccat 8280
caaaacaaaa cgaaacaaaa caaactagca aaataggctg tccccagtgc aagtgcaggt 8340
gccagaacat ttctctatcg ata 8363

<210> SEQ ID NO 3
<211> LENGTH: 10023
<212> TYPE: DNA
<213> ORGANISM: Artificial
<220> FEATURE:
<223> OTHER INFORMATION: an artificially synthesized vector sequence

<400> SEQUENCE: 3
gctcgagact agtgacttgg tgagtaggct tcgagcctag ttagaggact aggagaggcc 60
gtagccgtaa ctactctggg caagtagggc aggcggtggg tacgcaatgg gggcggctac 120
ctcagcacta aataggagac aattagacca atttgagaaa atacgacttc gcccgaacgg 180
aaagaaaaag taccaaatta aacatttaat atgggcaggc aaggagatgg agcgcttcgg 240
cctccatgag aggttgttgg agacagagga ggggtgtaaa agaatcatag aagtcctcta 300

-continued

```
ccccctagaa ccaacaggat cggagggctt aaaaagtctg ttcaatcttg tgtgcgtact    360
atattgcttg cacaaggaac agaaagtgaa agacacagag gaagcagtag caacagtaag    420
acaacactgc catctagtgg aaaaagaaaa aagtgcaaca gagacatcta gtggacaaaa    480
gaaaaatgac aagggaatag cagcgccacc tggtggcagt cagaattttc cagcgcaaca    540
acaaggaaat gcctgggtac atgtaccctt gtcaccgcgc accttaaatg cgtgggtaaa    600
agcagtagag gagaaaaaat ttggagcaga aatagtaccc atgtttcaag ccctatcaga    660
aggctgcaca ccctatgaca ttaatcagat gcttaatgtg ctaggagatc atcaaggggc    720
attacaaata gtgaaagaga tcattaatga agaagcagcc cagtgggatg taacacaccc    780
actacccgca ggacccctac cagcaggaca gctcagggac cctcgcggct cagatatagc    840
agggaccacc agctcagtac aagaacagtt agaatggatc tatactgcta acccccgggt    900
agatgtaggt gccatctacc ggagatggat tattctagga cttcaaaagt gtgtcaaaat    960
gtacaaccca gtatcagtcc tagacattag gcagggacct aaagagccct tcaaggatta   1020
tgtggacaga ttttacaagg caattagagc agaacaagcc tcaggggaag tgaaacaatg   1080
gatgacagaa tcattactca ttcaaaatgc taatccagat tgtaaggtca tcctgaaggg   1140
cctaggaatg caccccaccc ttgaagaaat gttaacggct tgtcaggggg taggaggccc   1200
aagctacaaa gcaaaagtaa tggcagaaat gatgcagacc atgcaaaatc aaaacatggt   1260
gcagcaggga ggtccaaaaa gacaaagacc cccactaaga tgttataatt gtggaaaatt   1320
tggccatatg caaagacaat gtccggaacc aaggaaaaca aaatgtctaa agtgtggaaa   1380
attgggacac ctagcaaaag actgcagggg acaggtgaat tttttagggt atggacggtg   1440
gatgggggca aaaccgagaa attttcccgc cgctactctt ggagcggaac cgagtgcgcc   1500
tccttcaccg agcggcacca ccccatacga cccagcaaag aagctcctgc agcaatatgc   1560
agagaaaggg aaacaactga gggagcaaaa gaggaatcca ccggcaatga atccggattg   1620
gaccgaggga tattctttga actccctctt tggagaagac caataaagac agtgtatata   1680
gaaggggtcc ccattaaggc actgctagac acaggggcag atgacaccat aattaaagaa   1740
aatgatttac aattatcagg tccatggaga cccaaaatta tagggggcat aggaggaggc   1800
cttaatgtaa aagaatataa cgacagggaa gtaaaaatag aagataaaat tttgagagga   1860
acaatattgt taggagcaac tcccattaat ataataggta gaaatttgct ggccccggca   1920
ggtgcccggt tagtaatggg acaattatca gaaaaaattc ctgtcacacc tgtcaaattg   1980
aaggaagggg ctcggggacc ctgtgtaaga caatggcctc tctctaaaga gaagattgaa   2040
gctttacagg aaatatgttc ccaattagag caggaaggaa aaatcagtag agtaggagga   2100
gaaaatgcat acaataccc aatattttgc ataaagaaga aggacaaatc ccagtggagg   2160
atgctagtag actttagaga gttaaataag gcaacccaag atttctttga agtgcaatta   2220
gggataccc acccagcagg attaagaaag atgagacaga taacagtttt agatgtagga   2280
gacgcctatt attccatacc attggatcca aattttagga aatatactgc ttttactatt   2340
cccacagtga ataatcaggg acccgggatt aggtatcaat tcaactgtct cccgcaaggg   2400
tggaaaggat ctcctacaat cttccaaaat acagcagcat ccattttgga ggagataaaa   2460
agaaacttgc cagcactaac cattgtacaa tacatggatg atttatgggt aggttctcaa   2520
gaaaatgaac acacccatga caaattagta gaacagttaa gaacaaaatt acaagcctgg   2580
ggcttagaaa ccccagaaaa gaaggtgcaa aaagaaccac cttatgagtg gatgggatac   2640
aaactttggc ctcacaaatg ggaactaagc agaatacaac tggaggaaaa agatgaatgg   2700
```

-continued

```
actgtcaatg acatccagaa gttagttggg aaactaaatt gggcagcaca attgtatcca   2760
ggtcttagga ccaagaatat atgcaagtta attagaggaa agaaaaatct gttagagcta   2820
gtgacttgga cacctgaggc agaagctgaa tatgcagaaa atgcagagat tcttaaaaca   2880
gaacaggaag gaacctatta caaaccagga atacctatta gggcagcagt acagaaattg   2940
gaaggaggac agtggagtta ccaattcaaa caagaaggac aagtcttgaa agtaggaaaa   3000
tacaccaagc aaaagaacac ccatacaaat gaacttcgca cattagctgg tttagtgcag   3060
aagatttgca aagaagctct agttatttgg gggatattac cagttctaga actcccgata   3120
gaaagagagg tatgggaaca atggtgggcg gattactggc aggtaagctg gattcccgaa   3180
tgggattttg tcagcacccc acctttgctc aaactatggt acacattaac aaaagaaccc   3240
atacccaagg aggacgttta ctatgtagat ggagcatgca acagaaattc aaaagaagga   3300
aaagcaggat acatctcaca atacggaaaa cagagagtag aaacattaga aaacactacc   3360
aatcagcaag cagaattaac agctataaaa atggctttgg aagacagtgg gcctaatgtg   3420
aacatagtaa cagactctca atatgcaatg ggaattttga cagcacaacc cacacaaagt   3480
gattcaccat tagtagagca aattatagcc ttaatgatac aaaagcaaca aatatatttg   3540
cagtgggtac cagcacataa aggaatagga ggaaatgagg agatagataa attagtgagt   3600
aaaggcatta gaagagtttt attcttagaa aaaatagaag aagctcaaga agagcatgaa   3660
agatatcata ataattggaa aaacctagca gatacatatg ggcttccaca aatagtagca   3720
aaagagatag tggccatgtg tccaaaatgt cagataaagg gagaaccagt gcatggacaa   3780
gtggatgcct cacctggaac atggcagatg gattgtactc atctagaagg aaaagtagtc   3840
atagttgcgg tccatgtagc cagtggattc atagaagcag aagtcatacc tagggaaaca   3900
ggaaaagaaa cggcaaagtt tctattaaaa atactgagta gatggcctat aacacagtta   3960
cacacagaca atgggcctaa ctttacctcc caagaagtgg cagcaatatg ttggtgggga   4020
aaaattgaac atacaacagg tataccatat aacccccaat ctcaaggatc aatagaaagc   4080
atgaacaaac aattaaaaga gataattggg aaaataagag atgattgcca atatacagag   4140
acagcagtac tgatggcttg ccatattcac aattttaaaa gaaagggagg aataggggga   4200
cagacttcag cagagagact aattaatata ataacaacac aattagaaat acaacattta   4260
caaaccaaaa ttcaaaaaat tttaaatttt agagtctact acagagaagg gagagaccct   4320
gtgtggaaag gaccagcaca attaatctgg aaaggggaag gagcagtggt cctcaaggac   4380
ggaagtgacc taaaggttgt accaagaagg aaagctaaaa ttattaagga ttatgaaccc   4440
aaacaaagag tgggtaatga gggtgacgtg gaaggtacca ggggatctga taactaaatg   4500
gcagggaata gtcagatatt ggatgagaca aagaaatttg aaatggaact attatatgca   4560
tcagctggcg gccgcgaatt cactagtgat tcccgtttgt gctagggttc ttaggcttct   4620
tgggggctgc tggaactgca atgggagcag cggcgacagc cctgacggtc cagtctcagc   4680
atttgcttgc tgggatactg cagcagcaga agaatctgct ggcggctgtg gaggctcaac   4740
agcagatgtt gaagctgacc atttggggtg ttaaaaacct caatgcccgc gtcacagccc   4800
ttgagaagta cctagaggat caggcacgac taaactcctg gggtgcgca tggaaacaag   4860
tatgtcatac cacagtggag tggccctgga caaatcggac tccggattgg caaaatatga   4920
cttggttgga gtgggaaaga caaatagctg atttggaaag caacattacg agacaattag   4980
tgaaggctag agaacaagag gaaaagaatc tagatgccta tcagaagtta actagttggt   5040
cagatttctg gtcttggttc gatttctcaa aatggcttaa cattttaaaa atgggatttt   5100
```

-continued

```
tagtaatagt aggaataata gggttaagat tactttacac agtatatgga tgtatagtga   5160

gggttaggca gggatatgtt cctctatctc cacagatcca tatccaatcg aattcccgcg   5220

gccgcaattc actcctcagg tgcaggctgc ctatcagaag gtggtggctg gtgtggccaa   5280

tgccctggct cacaaatacc actgagatct ttttccctct gccaaaaatt atggggacat   5340

catgaagccc cttgagcatc tgacttctgg ctaataaagg aaatttattt tcattgcaat   5400

agtgtgttgg aatttttgt gtctctcact cggaaggaca tatgggaggg caaatcattt   5460

aaaacatcag aatgagtatt tggtttagag tttggcaaca tatgcccata tgctggctgc   5520

catgaacaaa ggttggctat aaagaggtca tcagtatatg aaacagcccc ctgctgtcca   5580

ttccttattc catagaaaag ccttgacttg aggttagatt tttttatat tttgttttgt   5640

gttatttttt tctttaacat ccctaaaatt ttccttacat gttttactag ccagattttt   5700

cctcctctcc tgactactcc cagtcatagc tgtccctctt ctcttatgga gatccctcga   5760

cctgcagccc aagcttggcg taatcatggt catagctgtt tcctgtgtga aattgttatc   5820

cgctcacaat tccacacaac atacgagccg gaagcataaa gtgtaaagcc tggggtgcct   5880

aatgagtgag ctaactcaca ttaattgcgt tgcgctcact gcccgctttc cagtcgggaa   5940

acctgtcgtg ccagcggatc cgcatctcaa ttagtcagca accatagtcc cgcccctaac   6000

tccgcccatc ccgcccctaa ctccgcccag ttccgcccat tctccgcccc atggctgact   6060

aatttttttt atttatgcag aggccgaggc cgcctcggcc tctgagctat tccagaagta   6120

gtgaggaggc ttttttggag gcctaggctt ttgcaaaaag ctaacttgtt tattgcagct   6180

tataatggtt acaaataaag caatagcatc acaaatttca caaataaagc atttttttca   6240

ctgcattcta gttgtggttt gtccaaactc atcaatgtat cttatcatgt ctggatccgc   6300

tgcattaatg aatcggccaa cgcgcgggga gaggcggttt gcgtattggg cgctcttccg   6360

cttcctcgct cactgactcg ctgcgctcgg tcgttcggct gcggcgagcg gtatcagctc   6420

actcaaaggc ggtaatacgg ttatccacag aatcagggga taacgcagga aagaacatgt   6480

gagcaaaagg ccagcaaaag gccaggaacc gtaaaaaggc cgcgttgctg gcgtttttcc   6540

ataggctccg cccccctgac gagcatcaca aaaatcgacg ctcaagtcag aggtggcgaa   6600

acccgacagg actataaaga taccaggcgt ttccccctgg aagctccctc gtgcgctctc   6660

ctgttccgac cctgccgctt accggatacc tgtccgcctt tctcccttcg ggaagcgtgg   6720

cgctttctca tagctcacgc tgtaggtatc tcagttcggt gtaggtcgtt cgctccaagc   6780

tgggctgtgt gcacgaaccc cccgttcagc ccgaccgctg cgccttatcc ggtaactatc   6840

gtcttgagtc caacccggta agacacgact tatcgccact ggcagcagcc actggtaaca   6900

ggattagcag agcgaggtat gtaggcggtg ctacagagtt cttgaagtgg tggcctaact   6960

acggctacac tagaagaaca gtatttggta tctgcgctct gctgaagcca gttaccttcg   7020

gaaaaagagt tggtagctct tgatccggca aacaaaccac cgctggtagc ggtggttttt   7080

ttgtttgcaa gcagcagatt acgcgcagaa aaaaaggatc tcaagaagat cctttgatct   7140

tttctacggg gtctgacgct cagtggaacg aaaactcacg ttaagggatt ttggtcatga   7200

gattatcaaa aaggatcttc acctagatcc ttttaaatta aaaatgaagt tttaaatcaa   7260

tctaaagtat atatgagtaa acttggtctg acagttacca atgcttaatc agtgaggcac   7320

ctatctcagc gatctgtcta tttcgttcat ccatagttgc ctgactcccc gtcgtgtaga   7380

taactacgat acgggagggc ttaccatctg gccccagtgc tgcaatgata ccgcgagacc   7440

cacgctcacc ggctccagat ttatcagcaa taaaccagcc agccggaagg gccgagcgca   7500
```

```
gaagtggtcc tgcaacttta tccgcctcca tccagtctat taattgttgc cgggaagcta   7560
gagtaagtag ttcgccagtt aatagtttgc gcaacgttgt tgccattgct acaggcatcg   7620
tggtgtcacg ctcgtcgttt ggtatggctt cattcagctc cggttcccaa cgatcaaggc   7680
gagttacatg atcccccatg ttgtgcaaaa aagcggttag ctccttcggt cctccgatcg   7740
ttgtcagaag taagttggcc gcagtgttat cactcatggt tatggcagca ctgcataatt   7800
ctcttactgt catgccatcc gtaagatgct tttctgtgac tggtgagtac tcaaccaagt   7860
cattctgaga atagtgtatg cggcgaccga gttgctcttg cccggcgtca atacgggata   7920
ataccgcgcc acatagcaga actttaaaag tgctcatcat tggaaaacgt tcttcggggc   7980
gaaaactctc aaggatctta ccgctgttga gatccagttc gatgtaaccc actcgtgcac   8040
ccaactgatc ttcagcatct tttactttca ccagcgtttc tgggtgagca aaaacaggaa   8100
ggcaaaatgc cgcaaaaaag ggaataaggg cgacacggaa atgttgaata ctcatactct   8160
tcctttttca atattattga agcatttatc agggttattg tctcatgagc ggatacatat   8220
ttgaatgtat ttagaaaaat aaacaaatag gggttccgcg cacatttccc cgaaaagtgc   8280
cacctgggtc gatcgacatt gattattgac tagttattaa tagtaatcaa ttacggggtc   8340
attagttcat agcccatata tggagttccg cgttacataa cttacggtaa atggcccgcc   8400
tggctgaccg cccaacgacc cccgcccatt gacgtcaata atgacgtatg ttcccatagt   8460
aacgccaata gggactttcc attgacgtca atgggtggag tatttacggt aaactgccca   8520
cttggcagta catcaagtgt atcatatgcc aagtacgccc cctattgacg tcaatgacgg   8580
taaatggccc gcctggcatt atgcccagta catgacctta tgggactttc ctacttggca   8640
gtacatctac gtattagtca tcgctattac catggtcgag gtgagcccca cgttctgctt   8700
cactctcccc atctcccccc cctccccacc cccaattttg tatttattta tttttaatt    8760
attttgtgca gcgatggggg cgggggggggg gggggggcgc gcgccaggcg gggcggggcg   8820
gggcgagggg cggggcgggg cgaggcggag aggtgcggcg gcagccaatc agagcggcgc   8880
gctccgaaag tttcctttta tggcgaggcg gcggcggcgg cggccctata aaaagcgaag   8940
cgcgcggcgg gcgggagtcg ctgcgcgctg ccttcgcccc gtgccccgct ccgccgccgc   9000
ctcgcgccgc ccgccccggc tctgactgac cgcgttactc ccacaggtga gcgggcggga   9060
cggcccttct cctccgggct gtaattagcg cttggtttaa tgacggcttg tttcttttct   9120
gtggctgcgt gaaagccttg aggggctccg ggagggccct ttgtgcgggg ggagcggctc   9180
gggggtgcg tgcgtgtgtg tgtgcgtggg gagcgccgcg tgcggctccg cgctgcccgg    9240
cggctgtgag cgctgcgggc gcggcgcggg gctttgtgcg ctccgcagtg tgcgcgaggg   9300
gagcgcggcc gggggcggtg ccccgcggtg cgggggggggc tgcgagggga acaaaggctg   9360
cgtgcggggt gtgtgcgtgg gggggtgagc agggggtgtg ggcgcgtcgg tcgggctgca   9420
acccccctg caccccccctc cccgagttgc tgagcacggc ccggcttcgg gtgcggggct   9480
ccgtacgggg cgtggcgcgg ggctcgccgt gccgggcggg gggtggcggc aggtgggggt   9540
gccgggcggg gcggggccgc ctcgggccgg ggagggctcg gggggagggc gcggcggccc   9600
ccggagcgcc ggcggctgtc gaggcgcggc gagccgcagc cattgccttt tatggtaatc   9660
gtgcgagagg gcgcagggac ttcctttgtc ccaaatctgt gcggagccga aatctgggag   9720
gcgccgccgc acccccctcta gcgggcgcgg ggcgaagcgg tgcggcgccg gcaggaagga   9780
aatgggcggg gagggccttc gtgcgtcgcc gcgccgccgt ccccttctcc ctctccagcc   9840
tcggggctgt ccgcgggggg acggctgcct tcgggggggga cggggcaggg cggggttcgg   9900
```

-continued

```
cttctggcgt gtgaccggcg gctctagagc ctctgctaac catgttcatg ccttcttctt   9960

tttcctacag ctcctgggca acgtgctggt tattgtgctg tctcatcatt ttggcaaaga  10020

att                                                                10023
```

<210> SEQ ID NO 4
<211> LENGTH: 982
<212> TYPE: DNA
<213> ORGANISM: Simian immunodeficiency virus

<400> SEQUENCE: 4

```
cagtctctta ctaggagacc agcttgagcc tgggtgttcg ctggttagcc taacctggtt     60

ggccaccagg ggtaaggact ccttggctta gaaagctaat aaacttgcct gcattagagc    120

ttatctgagt caagtgtcct cattgacgcc tcactctctt gaacgggaat cttccttact    180

gggttctctc tctgacccag gcgagagaaa ctccagcagt ggcgcccgaa cagggacttg    240

agtgagagtg taggcacgta cagctgagaa ggcgtcggac gcgaaggaag cgcggggtgc    300

gacgcgacca agaaggagac ttggtgagta ggcttctcga gtgccgggaa aaagctcgag    360

cctagttaga ggactaggag aggccgtagc cgtaactact ctgggcaagt agggcaggcg    420

gtgggtacgc aatgggggcg gctacctcag cactaaatag gagacaatta gaccaatttg    480

agaaaatacg acttcgcccg aacggaaaga aaaagtacca aattaaacat ttaatatggg    540

caggcaagga gatggagcgc ttcggcctcc atgagaggtt gttggagaca gaggaggggt    600

gtaaaagaat catagaagtc ctctacccc tagaaccaac aggatcggag ggcttaaaaa    660

gtctgttcaa tcttgtgtgc gtgctatatt gcttgcacaa ggaacagaaa gtgaaagaca    720

cagaggaagc agtagcaaca gtaagacaac actgccatct agtggaaaaa gaaaaaagtg    780

caacagagac atctagtgga caaaagaaaa atgacaaggg aatagcagcg ccacctggtg    840

gcagtcagaa ttttccagcg caacaacaag gaaatgcctg ggtacatgta cccttgtcac    900

cgcgcacctt aaatgcgtgg gtaaaagcag tagaggagaa aaaatttgga gcagaaatag    960

tacccatgtt tcaagcccta tc                                             982
```

<210> SEQ ID NO 5
<211> LENGTH: 614
<212> TYPE: DNA
<213> ORGANISM: Simian immunodeficiency virus

<400> SEQUENCE: 5

```
cccgtttgtg ctagggttct taggcttctt gggggctgct ggaactgcaa tgggagcagc     60

ggcgacagcc ctgacggtcc agtctcagca tttgcttgct gggatactgc agcagcagaa    120

gaatctgctg gcggctgtgg aggctcaaca gcagatgttg aagctgacca tttggggtgt    180

taaaaacctc aatgcccgcg tcacagccct tgagaagtac ctagaggatc aggcacgact    240

aaactcctgg gggtgcgcat ggaaacaagt atgtcatacc acagtggagt ggccctggac    300

aaatcggact ccggattggc aaaatatgac ttggttggag tgggaaagac aaatagctga    360

tttggaaagc aacattacga gacaattagt gaaggctaga gaacaagagg aaaagaatct    420

agatgcctat cagaagttaa ctagttggtc agatttctgg tcttggttcg atttctcaaa    480

atggcttaac attttaaaaa tgggattttt agtaatagta ggaataatag ggttaagatt    540

actttacaca gtatatggat gtatagtgag ggttaggcag ggatatgttc ctctatctcc    600

acagatccat atcc                                                      614
```

<210> SEQ ID NO 6

-continued

<211> LENGTH: 185
<212> TYPE: DNA
<213> ORGANISM: Simian immunodeficiency virus

<400> SEQUENCE: 6
gcacttttta aaagaaaagg gaggactgga tgggatttat tactccgata ggacgctggc 60
ttgtaactca gtctcttact aggagaccag cttgagcctg ggtgttcgct ggttagccta 120
acctggttgg ccaccagggg taaggactcc ttggcttaga aagctaataa acttgcctgc 180
attag 185

<210> SEQ ID NO 7
<211> LENGTH: 9171
<212> TYPE: DNA
<213> ORGANISM: Simian immunodeficiency virus

<400> SEQUENCE: 7
cagtctctta ctaggagacc agcttgagcc tgggtgttcg ctggttagcc taacctggtt 60
ggccaccagg ggtaaggact ccttggctta gaaagctaat aaacttgcct gcattagagc 120
ttatctgagt caagtgtcct cattgacgcc tcactctctt gaacgggaat cttccttact 180
gggttctctc tctgacccag gcgagagaaa ctccagcagt ggcgcccgaa cagggacttg 240
agtgagagtg taggcacgta cagctgagaa ggcgtcggac gcgaaggaag cgcggggtgc 300
gacgcgacca agaaggagac ttggtgagta ggcttctcga gtgccgggaa aaagctcgag 360
cctagttaga ggactaggag aggccgtagc cgtaactact ctgggcaagt agggcaggcg 420
gtgggtacgc aatgggggcg gctacctcag cactaaatag gagacaatta gaccaatttg 480
agaaaatacg acttcgcccg aacggaaaga aaaagtacca aattaaacat ttaatatggg 540
caggcaagga gatggagcgc ttcggcctcc atgagaggtt gttggagaca gaggaggggt 600
gtaaaagaat catagaagtc ctctaccccc tagaaccaac aggatcggag ggcttaaaaa 660
gtctgttcaa tcttgtgtgc gtactatatt gcttgcacaa ggaacagaaa gtgaaagaca 720
cagaggaagc agtagcaaca gtaagacaac actgccatct agtggaaaaa gaaaaaagtg 780
caacagagac atctagtgga caaaagaaaa atgacaaggg aatagcagcg ccacctggtg 840
gcagtcagaa ttttccagcg caacaacaag gaaatgcctg ggtacatgta cccttgtcac 900
cgcgcacctt aaatgcgtgg gtaaaagcag tagaggagaa aaaatttgga gcagaaatag 960
tacccatgtt tcaagcccta tcagaaggct gcacacccta tgacattaat cagatgctta 1020
atgtgctagg agatcatcaa ggggcattac aaatagtgaa agagatcatt aatgaagaag 1080
cagcccagtg ggatgtaaca cacccactac ccgcaggacc cctaccagca ggacagctca 1140
gggaccctcg cggctcagat atagcaggga ccaccagctc agtacaagaa cagttagaat 1200
ggatctatac tgctaacccc cgggtagatg taggtgccat ctaccggaga tggattattc 1260
taggacttca aaagtgtgtc aaaatgtaca acccagtatc agtcctagac attaggcagg 1320
gacctaaaga gcccttcaag gattatgtgg acagatttta caaggcaatt agagcagaac 1380
aagcctcagg ggaagtgaaa caatggatga cagaatcatt actcattcaa aatgctaatc 1440
cagattgtaa ggtcatcctg aagggcctag gaatgcaccc cacccttgaa gaaatgttaa 1500
cggcttgtca gggggtagga ggcccaagct acaaagcaaa agtaatggca gaaatgatgc 1560
agaccatgca aaatcaaaac atggtgcagc agggaggtcc aaaaagacaa agacccccac 1620
taagatgtta taattgtgga aaatttggcc atatgcaaag acaatgtccg gaaccaagga 1680
aaacaaaatg tctaaagtgt ggaaaattgg gacacctagc aaaagactgc aggggacagg 1740

-continued

```
tgaatttttt agggtatgga cggtggatgg gggcaaaacc gagaaatttt cccgccgcta   1800
ctcttggagc ggaaccgagt gcgcctcctc caccgagcgg caccacccca tacgacccag   1860
caaagaagct cctgcagcaa tatgcagaga aagggaaaca actgagggag caaaagagga   1920
atccaccggc aatgaatccg gattggaccg agggatattc tttgaactcc ctctttggag   1980
aagaccaata aagacagtgt atatagaagg ggtccccatt aaggcactgc tagacacagg   2040
ggcagatgac accataatta aagaaaatga tttacaatta tcaggtccat ggagacccaa   2100
aattataggg ggcataggag gaggccttaa tgtaaaagaa tataacgaca gggaagtaaa   2160
aatagaagat aaaattttga gaggaacaat attgttagga gcaactccca ttaatataat   2220
aggtagaaat ttgctggccc cggcaggtgc ccggttagta atgggacaat tatcagaaaa   2280
aattcctgtc acacctgtca aattgaagga aggggctcgg ggaccctgtg taagacaatg   2340
gcctctctct aaagagaaga ttgaagcttt acaggaaata tgttcccaat tagagcagga   2400
aggaaaaatc agtagagtag gaggagaaaa tgcatacaat accccaatat tttgcataaa   2460
gaagaaggac aaatcccagt ggaggatgct agtagacttt agagagttaa ataaggcaac   2520
ccaagatttc tttgaagtgc aattagggat accccaccca gcaggattaa gaaagatgag   2580
acagataaca gttttagatg taggagacgc ctattattcc ataccattgg atccaaattt   2640
taggaaatat actgctttta ctattcccac agtgaataat cagggacccg ggattaggta   2700
tcaattcaac tgtctcccgc aagggtggaa aggatctcct acaatcttcc aaaatacagc   2760
agcatccatt ttggaggaga taaaaagaaa cttgccagca ctaaccattg tacaatacat   2820
ggatgattta tgggtaggtt ctcaagaaaa tgaacacacc catgacaaat tagtagaaca   2880
gttaagaaca aaattacaag cctggggctt agaaacccca gaaaagaagg tgcaaaaaga   2940
accaccttat gagtggatgg gatacaaact ttggcctcac aaatgggaac taagcagaat   3000
acaactggag gaaaaagatg aatggactgt caatgacatc cagaagttag ttgggaaact   3060
aaattgggca gcacaattgt atccaggtct taggaccaag aatatatgca agttaattag   3120
aggaaagaaa aatctgttag agctagtgac ttggacacct gaggcagaag ctgaatatgc   3180
agaaaatgca gagattctta aaacagaaca ggaaggaacc tattacaaac caggaatacc   3240
tattagggca gcagtacaga aattggaagg aggacagtgg agttaccaat tcaaacaaga   3300
aggacaagtc ttgaaagtag gaaaatacac caagcaaaag aacacccata caaatgaact   3360
tcgcacatta gctggtttag tgcagaagat ttgcaaagaa gctctagtta tttgggggat   3420
attaccagtt ctagaactcc cgatagaaag agaggtatgg gaacaatggt gggcggatta   3480
ctggcaggta agctggattc ccgaatggga ttttgtcagc accccacctt tgctcaaact   3540
atggtacaca ttaacaaaag aacccatacc caaggaggac gtttactatg tagatggagc   3600
atgcaacaga aattcaaaag aaggaaaagc aggatacatc tcacaatacg gaaaacagag   3660
agtagaaaca ttagaaaaca ctaccaatca gcaagcagaa ttaacagcta taaaaatggc   3720
tttggaagac agtgggccta atgtgaacat agtaacagac tctcaatatg caatgggaat   3780
tttgacagca caacccacac aaagtgattc accattagta gagcaaatta tagccttaat   3840
gatacaaaag caacaaatat atttgcagtg ggtaccagca cataaaggaa taggaggaaa   3900
tgaggagata gataaattag tgagtaaagg cattagaaga gttttattct tagaaaaaat   3960
agaagaagct caagaagagc atgaaagata tcataataat tggaaaaacc tagcagatac   4020
atatgggctt ccacaaatag tagcaaaaga gatagtggcc atgtgtccaa aatgtcagat   4080
aaagggagaa ccagtgcatg gacaagtgga tgcctcacct ggaacatggc agatggattg   4140
```

-continued

```
tactcatcta gaaggaaaag tagtcatagt tgcggtccat gtagccagtg gattcataga   4200

agcagaagtc atacctaggg aaacaggaaa agaaacggca aagtttctat taaaaatact   4260

gagtagatgg cctataacac agttacacac agacaatggg cctaacttta cctcccaaga   4320

agtggcagca atatgttggt ggggaaaaat tgaacataca acaggtatac catataaccc   4380

ccaatctcaa ggatcaatag aaagcatgaa caaacaatta aaagagataa ttgggaaaat   4440

aagagatgat tgccaatata cagagacagc agtactgatg gcttgccata ttcacaattt   4500

taaaagaaag ggaggaatag gggacagac ttcagcagag agactaatta atataataac   4560

aacacaatta gaaatacaac atttacaaac caaaattcaa aaaattttaa attttagagt   4620

ctactacaga gaagggagag accctgtgtg gaaaggacca gcacaattaa tctggaaagg   4680

ggaaggagca gtggtcctca aggacggaag tgacctaaag gttgtaccaa gaaggaaagc   4740

taaaattatt aaggattatg aacccaaaca aagagtgggt aatgagggtg acgtggaagg   4800

taccagggga tctgataact aaatggcagg gaatagtcag atattggatg agacaaagaa   4860

atttgaaatg gaactattat atgcattacc aaattacatg ggcttggtac accatgagta   4920

gatatgtaat accaatagga aaacatgggg aaatatgtgt agacctatat tggcatttaa   4980

caccagagca aggatggcta tccacatatg cagtaggtat acaatatgta agcaatttag   5040

aatctaaata tagaacagaa ttagaccctg ctacagcaga tagtataata catggtcact   5100

attttaattg ttttaaagaa agagccatcc aacaagctct gaggggccac agatttgtct   5160

tctgtcagtt tccagaaggg cataaaagca caggacaggt accatctttg cagtacctag   5220

ctctgctcgc acatcaaaat ggcctcaggg agagatccaa gagaggcaag accaggagaa   5280

gtagaaattt gggatctaag cagggagccg tgggacgaat ggctaagaga tatgttacaa   5340

gatctcaacc aggaggcgag gctgcatttt tgggagagaa ctcctgttcc aagtatggaa   5400

ctactgtcag gaggaaggag aaagacatgg tactcccatg atggaaaggg cctacaaata   5460

ttataggcta gtacaaaagg ctctctttgt gcattttcga tgtgggtgca ggagaaggca   5520

gccctttgaa ccatacgagg agaggagaga tggacaaggg ggaggcagag caaatcgtgt   5580

cccaccagga cttgagtgaa gactatcaga agcctctgca gacttgtaaa aataaatgtt   5640

tttgcaaaaa atgttgttac cactgtcagc tttgctttct gcaaaaaggc ctaggtgtta   5700

cctatcatgc ccctaggacc agaagaaaga agattgcttc gcttgatttg gctcctttac   5760

agcaccagta agtatgaggt atacaataat aaccttagga ataatagtga taggaatagg   5820

gatagtgtta agtaagcaat ggataacagt cttttatgga ataccagtat ggaaaaacag   5880

ctcggtgcag gctttctgca tgactcccac cacaagctta tgggctacta ctaattgcat   5940

accagatgat catgactata cagaagtacc tctaaatatc actgaaccat ttgaggcatg   6000

gggtgataga aacccattaa tagcacaagc agccagtaac atccatttac tctttgagca   6060

aactatgaaa ccttgtgtga agttatcacc actatgcatc aagatgaatt gtgtagagtt   6120

aaattccaca agagaaaggg cgacaacacc tacaacgacg ccgaaatcta ccggcctacc   6180

ctgtgtaggc ccgacgtcag gtgaaaatct acagtcctgt aatgcaagca ttatagaaag   6240

ggagatggag gatgagcccg cctctaattg tacattcgca atggctggct atgtaagaga   6300

tcagaagaaa aattattctg tggtgtggaa tgatgcagaa atctattgca aaaataagac   6360

taatagcact agcaaagagt gttacatgat tcattgtaat gactcagtta taaaagaagc   6420

atgtgacaaa acatattggg atcagttgag gttaaggtat tgtgctccag caggttatgc   6480

tttgctaaaa tgtaatgatg aagattataa tgggtataaa caaaattgct caaatgtatc   6540
```

-continued

```
agtagtgcat tgtacaggct taatgaatac aacagtgaca acagggttgt tgctgaatgg   6600
aagctatcat gagaatcgaa cccagatatg gcagaaacat agggtaaata ataacacagt   6660
attgatcttg ttcaacaagc actataatct atcagtcacc tgtaggagac caggaaacaa   6720
gacagtccta ccggtaacga taatggcggg actggttttc cactctcaaa aatacaacat   6780
gaagcttaga caggcttggt gtcacttcga aggcaattgg agaggtgcct ggcgggaagt   6840
aaaacaaaaa atagtagagt taccaaaaga caggtataaa ggaaccaata atacagaaca   6900
catatacctg caaagacaat ggggagaccc agaagcatcc aacttgtggt ttaattgtca   6960
aggagaattc ttttattgta agatggattg gtttttaaat tacttaaata ataaaacatg   7020
ggatgcagac cataattttt gtagcagcaa aaagaaagga cacgcaccag gaccatgtgt   7080
acaaaggacg tatgttgctt gccatatcag gtctgtaata aatgattggt ataccctatc   7140
aaagaaaact tatgctccgc caagagaagg acatttgcaa tgcaggtcca cagtcactgg   7200
gatgacagtt gagcttaatt ataatagtaa aaacagaacc aacgtgacac taagtcccca   7260
gatagaatct atctgggcgg ctgaattggg cagatacaaa ttagtggaaa tcacaccaat   7320
tggctttgca cccacagaag taaggcgtta tacgggagga catgagaggc aaaagagagt   7380
cccgtttgtg ctagggttct taggcttctt gggggctgct ggaactgcaa tgggagcagc   7440
ggcgacagcc ctgacggtcc agtctcagca tttgcttgct gggatactgc agcagcagaa   7500
gaatctgctg gcggctgtgg aggctcaaca gcagatgttg aagctgacca tttggggtgt   7560
taaaaacctc aatgcccgcg tcacagccct tgagaagtac ctagaggatc aggcacgact   7620
aaactcctgg gggtgcgcat ggaaacaagt atgtcatacc acagtggagt ggccctggac   7680
aaatcggact ccggattggc aaaatatgac ttggttggag tgggaaagac aaatagctga   7740
tttggaaagc aacattacga gacaattagt gaaggctaga gaacaagagg aaaagaatct   7800
agatgcctat cagaagttaa ctagttggtc agatttctgg tcttggttcg atttctcaaa   7860
atggcttaac attttaaaaa tgggattttt agtaatagta ggaataatag ggttaagatt   7920
actttacaca gtatatggat gtatagtgag ggttaggcag ggatatgttc ctctatctcc   7980
acagatccat atccaccaag tggggaaggg acggccagac aacgccgacg agccaggaga   8040
aggtggagac aacagcagga tcaaattaga gtcttggtag aaagactcca agagcaggtg   8100
tatgcagttg accgcctggc tgacgaggct caacacttgg ctatacaaca gttgcctgac   8160
cctcctcatt cagcttagga aagcttttca atacctgcaa tatgggctcg cagaactcaa   8220
aaccggcgca caagaaatac tccaaactct ggcaggcgtt gcacaaaacg catgtcacca   8280
gatatggctt gcttgcagat ccgcttatag gaacatcgtc aacagtccaa gaagagtgcg   8340
acaaggcctt gaggaaatcc ttaattagga aacaaaatgg caacatgacg gaagagggaa   8400
ggaggcttca agaaggagac acctgggaag agtggtcgga tgatgaggaa gaagtgggat   8460
ttccagtgag accaagagta cccttaaggc aaatgactta taaacttgca gtggattttt   8520
cgcacttttt aaaagaaaag ggaggactgg atgggattta ttactccgat aggagaaata   8580
agatcctgaa tctgtatgct cttaatgaat gggggataat tgatgattgg aatgcctggt   8640
cgaagggacc aggaataaga ttccctaaat gctttgggtt ctgctttaag ctagtgccag   8700
tggacttaca tgaggaagca caaacatgtg aaagacattg cctagtccat ccagcgcaga   8760
tgggagaaga tccagatggt atcagccatg gagagatctt ggtgtggaag tttgatccta   8820
tgttggcaat acagtacgac cccaatcggg agtactttac tgacatgcat gggctggtga   8880
agaggaagta gccagaccgc aagcctgcgg ttagaacatc accatggaga tgacattaaa   8940
```

-continued

```
aactgctgac gggactttcc agcgaaggga ctttccaagg cgggacatgg gcggtccggg   9000

gagtggcttt accctcagaa ctgcataaaa gcagatgctc gctggcttgt aactcagtct   9060

cttactagga gaccagcttg agcctgggtg ttcgctggtt agcctaacct ggttggccac   9120

caggggtaag gactccttgg cttagaaagc taataaactt gcctgcatta g            9171
```

<210> SEQ ID NO 8
<211> LENGTH: 1257
<212> TYPE: DNA
<213> ORGANISM: Homo sapiens

<400> SEQUENCE: 8

```
atgcaggccc tggtgctact cctctgcatt ggagccctcc tcgggcacag cagctgccag     60

aaccctgcca gccccccgga ggagggctcc ccagaccccg acagcacagg ggcgctggtg    120

gaggaggagg atcctttctt caaagtcccc gtgaacaagc tggcagcggc tgtctccaac    180

ttcggctatg acctgtaccg ggtgcgatcc agcatgagcc ccacgaccaa cgtgctcctg    240

tctcctctca gtgtggccac ggccctctcg gccctctcgc tgggagcgga gcagcgaaca    300

gaatccatca ttcaccgggc tctctactat gacttgatca gcagcccaga catccatggt    360

acctataagg agctccttga cacggtcact gccccccaga agaacctcaa gagtgcctcc    420

cggatcgtct ttgagaagaa gctgcgcata aaatccagct ttgtggcacc tctggaaaag    480

tcatatggga ccaggcccag agtcctgacg ggcaaccctc gcttggacct gcaagagatc    540

aacaactggg tgcaggcgca gatgaaaggg aagctcgcca ggtccacaaa ggaaattccc    600

gatgagatca gcattctcct tctcggtgtg gcgcacttca aggggcagtg ggtaacaaag    660

tttgactcca gaaagacttc cctcgaggat ttctacttgg atgaagagag gaccgtgagg    720

gtccccatga tgtcggaccc taaggctgtt ttacgctatg gcttggattc agatctcagc    780

tgcaagattg cccagctgcc cttgaccgga agcatgagta tcatcttctt cctgcccctg    840

aaagtgaccc agaatttgac cttgatagag gagagcctca cctccgagtt cattcatgac    900

atagaccgag aactgaagac cgtgcaggcg gtcctcactg tccccaagct gaagctgagt    960

tacgaaggcg aagtcaccaa gtccctgcag gagatgaagc tgcaatcctt gtttgattca   1020

ccagacttta gcaagatcac aggcaaaccc atcaagctga ctcaggtgga acaccgggct   1080

ggctttgagt ggaacgagga tggggcggga accaccccca gcccagggct gcagcctgcc   1140

cacctcacct tcccgctgga ctatcacctt aaccagcctt tcatcttcgt actgagggac   1200

acagacacag ggcccttct cttcattggc aagattctgg accccagggg cccctaa       1257
```

<210> SEQ ID NO 9
<211> LENGTH: 590
<212> TYPE: DNA
<213> ORGANISM: CMV

<400> SEQUENCE: 9

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420
```

atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cgtcagatcc 590

<210> SEQ ID NO 10
<211> LENGTH: 125
<212> TYPE: DNA
<213> ORGANISM: Simian immunodeficiency virus

<400> SEQUENCE: 10
caattttaaa agaaagggag gaataggggg acagacttca gcagagagac taattaatat 60
aataacaaca caattagaaa tacaacattt acaaaccaaa attcaaaaaa ttttaaattt 120
tagag 125

<210> SEQ ID NO 11
<211> LENGTH: 591
<212> TYPE: DNA
<213> ORGANISM: woodchuck hepatitis virus

<400> SEQUENCE: 11
ttaatcaacc tctggattac aaaatttgtg aaagattgac tggtattctt aactatgttg 60
ctccttttac gctatgtgga tacgctgctt taatgccttt gtatcatgct attgcttccc 120
gtatggcttt cattttctcc tccttgtata aatcctggtt gctgtctctt tatgaggagt 180
tgtggcccgt tgtcaggcaa cgtggcgtgg tgtgcactgt gtttgctgac gcaaccccca 240
ctggttgggg cattgccacc acctgtcagc tcctttccgg gactttcgct ttccccctcc 300
ctattgccac ggcggaactc atcgccgcct gccttgcccg ctgctggaca ggggctcggc 360
tgttgggcac tgacaattcc gtggtgttgt cggggaaatc atcgtccttt ccttggctgc 420
tcgcctgtgt tgccacctgg attctgcgcg ggacgtcctt ctgctacgtc ccttcggccc 480
tcaatccagc ggaccttcct tcccgcggcc tgctgccggc tctgcggcct cttccgcgtc 540
ttcgccttcg ccctcagacg agtcggatct ccctttgggc cgcctccccg c 591

<210> SEQ ID NO 12
<211> LENGTH: 255
<212> TYPE: DNA
<213> ORGANISM: Simian immunodeficiency virus

<400> SEQUENCE: 12
atgcccctag gaccagaaga aagaagattc gttcgcttaa tttggctcct ttacagcacc 60
aatccatatc caccaagtgg ggaagggacg gccagacaac gccgacgagc caggagaagg 120
tggagacaac agcaggatca aattagagtc ttggtagaaa gactccaaga gcaggtgtat 180
gcagttgacc gcctggctga cgaggctcaa cacttggcta tacaacagtt gcctgaccct 240
cctcattcag cttag 255

<210> SEQ ID NO 13
<211> LENGTH: 7060
<212> TYPE: DNA
<213> ORGANISM: Artificial
<220> FEATURE:
<223> OTHER INFORMATION: an artificially synthesized vector sequence

<400> SEQUENCE: 13
ggtacctcaa tattggccat tagccatatt attcattggt tatatagcat aaatcaatat 60
tggctattgg ccattgcata cgttgtatct atatcataat atgtacattt atattggctc 120

-continued

```
atgtccaata tgaccgccat gttggcattg attattgact agttattaat agtaatcaat    180
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca agtccgcccc ctattgacgt    420
caatgacggt aaatggcccg cctggcatta tgcccagtac atgaccttac gggactttcc    480
tacttggcag tacatctacg tattagtcat cgctattacc atggtgatgc ggttttggca    540
gtacaccaat gggcgtggat agcggtttga ctcacgggga tttccaagtc tccaccccat    600
tgacgtcaat gggagtttgt tttggcacca aaatcaacgg gactttccaa aatgtcgtaa    660
caactgcgat cgcccgcccc gttgacgcaa atgggcggta ggcgtgtacg gtgggaggtc    720
tatataagca gagctcgctg gcttgtaact cagtctctta ctaggagacc agcttgagcc    780
tgggtgttcg ctggttagcc taacctggtt ggccaccagg ggtaaggact ccttggctta    840
gaaagctaat aaacttgcct gcattagagc ttatctgagt caagtgtcct cattgacgcc    900
tcactctctt gaacgggaat cttccttact gggttctctc tctgacccag gcgagagaaa    960
ctccagcagt ggcgcccgaa cagggacttg agtgagagtg taggcacgta cagctgagaa   1020
ggcgtcggac gcgaaggaag cgcggggtgc gacgcgacca agaaggagac ttggtgagta   1080
ggcttctcga gtgccgggaa aaagctcgag cctagttaga ggactaggag aggccgtagc   1140
cgtaactact ctgggcaagt agggcaggcg gtgggtacgc aatgggggcg gctacctcag   1200
cactaaatag gagacaatta gaccaatttg agaaaatacg acttcgcccg aacggaaaga   1260
aaaagtacca aattaaacat ttaatatggg caggcaagga gatggagcgc ttcggcctcc   1320
atgagaggtt gttggagaca gaggaggggt gtaaaagaat catagaagtc ctctaccccc   1380
tagaaccaac aggatcggag ggcttaaaaa gtctgttcaa tcttgtgtgc gtgctatatt   1440
gcttgcacaa ggaacagaaa gtgaaagaca cagaggaagc agtagcaaca gtaagacaac   1500
actgccatct agtggaaaaa gaaaaaagtg caacagagac atctagtgga caaaagaaaa   1560
atgacaaggg aatagcagcg ccacctggtg gcagtcagaa ttttccagcg caacaacaag   1620
gaaatgcctg ggtacatgta cccttgtcac cgcgcacctt aaatgcgtgg gtaaaagcag   1680
tagaggagaa aaaatttgga gcagaaatag tacccatgtt tcaagcccta tcgaattccc   1740
gtttgtgcta gggttcttag gcttcttggg ggctgctgga actgcaatgg gagcagcggc   1800
gacagccctg acggtccagt ctcagcattt gcttgctggg atactgcagc agcagaagaa   1860
tctgctggcg gctgtggagg ctcaacagca gatgttgaag ctgaccattt ggggtgttaa   1920
aaacctcaat gcccgcgtca cagcccttga gaagtaccta gaggatcagg cacgactaaa   1980
ctcctggggg tgcgcatgga aacaagtatg tcataccaca gtggagtggc cctggacaaa   2040
tcggactccg gattggcaaa atatgacttg gttggagtgg gaaagacaaa tagctgattt   2100
ggaaagcaac attacgagac aattagtgaa ggctagagaa caagaggaaa agaatctaga   2160
tgcctatcag aagttaacta gttggtcaga tttctggtct tggttcgatt tctcaaaatg   2220
gcttaacatt ttaaaaatgg gatttttagt aatagtagga ataatagggt taagattact   2280
ttacacagta tatggatgta tagtgagggt taggcaggga tatgttcctc tatctccaca   2340
gatccatatc cgcggtagtt attaatagta atcaattacg gggtcattag ttcatagccc   2400
atatatggag ttccgcgtta cataacttac ggtaaatggc ccgcctggct gaccgcccaa   2460
cgacccccgc ccattgacgt caataatgac gtatgttccc atagtaacgc caatagggac   2520
```

-continued

```
tttccattga cgtcaatggg tggagtattt acggtaaact gcccacttgg cagtacatca   2580

agtgtatcat atgccaagta cgccccctat tgacgtcaat gacggtaaat ggcccgcctg   2640

gcattatgcc cagtacatga ccttatggga ctttcctact tggcagtaca tctacgtatt   2700

agtcatcgct attaccatgg tgatgcggtt ttggcagtac atcaatgggc gtggatagcg   2760

gtttgactca cggggatttc caagtctcca ccccattgac gtcaatggga gtttgttttg   2820

gcaccaaaat caacgggact ttccaaaatg tcgtaacaac tccgccccat tgacgcaaat   2880

gggcggtagg cgtgtacggt gggaggtcta tataagcaga gctggtttag tgaaccgtca   2940

gatccgctag cgctaccggt cgccaccatg gtgagcaagg gcgaggagct gttcaccggg   3000

gtggtgccca tcctggtcga gctggacggc gacgtaaacg gccacaagtt cagcgtgtcc   3060

ggcgagggcg agggcgatgc cacctacggc aagctgaccc tgaagttcat ctgcaccacc   3120

ggcaagctgc ccgtgccctg gcccaccctc gtgaccaccc tgacctacgg cgtgcagtgc   3180

ttcagccgct accccgacca catgaagcag cacgacttct tcaagtccgc catgcccgaa   3240

ggctacgtcc aggagcgcac catcttcttc aaggacgacg gcaactacaa gacccgcgcc   3300

gaggtgaagt tcgagggcga caccctggtg aaccgcatcg agctgaaggg catcgacttc   3360

aaggaggacg gcaacatcct ggggcacaag ctggagtaca actacaacag ccacaacgtc   3420

tatatcatgg ccgacaagca gaagaacggc atcaaggtga acttcaagat ccgccacaac   3480

atcgaggacg gcagcgtgca gctcgccgac cactaccagc agaacacccc catcggcgac   3540

ggccccgtgc tgctgcccga caaccactac ctgagcaccc agtccgccct gagcaaagac   3600

cccaacgaga agcgcgatca catggtcctg ctggagttcg tgaccgccgc cgggatcact   3660

ctcggcatgg acgagctgta caagtaagcg gccgcggatc cgcacttttt aaaagaaaag   3720

ggaggactgg atgggattta ttactccgat aggacgctgg cttgtaactc agtctcttac   3780

taggagacca gcttgagcct gggtgttcgc tggttagcct aacctggttg gccaccaggg   3840

gtaaggactc cttggcttag aaagctaata aacttgcctg cattagagct cttacgcgtg   3900

ctagcccggg ctcgagatcc gcatctcaat tagtcagcaa ccatagtccc gcccctaact   3960

ccgcccatcc cgcccctaac tccgcccagt tccgcccatt ctccgcccca tggctgacta   4020

attttttta tttatgcaga ggccgaggcc gcctcggcct ctgagctatt ccagaagtag   4080

tgaggaggct tttttggagg cctaggcttt tgcaaaaagc taacttgttt attgcagctt   4140

ataatggtta caaataaagc aatagcatca caaatttcac aaataaagca tttttttcac   4200

tgcattctag ttgtggtttg tccaaactca tcaatgtatc ttatcatgtc tgtcgaccga   4260

tgcccttgag agccttcaac ccagtcagct ccttccggtg ggcgcggggc atgactatcg   4320

tcgccgcact tatgactgtc ttctttatca tgcaactcgt aggacaggtg ccggcagcgc   4380

tcttccgctt cctcgctcac tgactcgctg cgctcggtcg ttcggctgcg gcgagcggta   4440

tcagctcact caaaggcggt aatacggtta tccacagaat caggggataa cgcaggaaag   4500

aacatgtgag caaaaggcca gcaaaaggcc aggaaccgta aaaaggccgc gttgctggcg   4560

tttttccata ggctccgccc ccctgacgag catcacaaaa atcgacgctc aagtcagagg   4620

tggcgaaacc cgacaggact ataaagatac caggcgtttc cccctggaag ctccctcgtg   4680

cgctctcctg ttccgaccct gccgcttacc ggatacctgt ccgcctttct cccttcggga   4740

agcgtggcgc tttctcaatg ctcacgctgt aggtatctca gttcggtgta ggtcgttcgc   4800

tccaagctgg gctgtgtgca cgaacccccc gttcagcccg accgctgcgc cttatccggt   4860

aactatcgtc ttgagtccaa cccggtaaga cacgacttat cgccactggc agcagccact   4920
```

-continued

```
ggtaacagga ttagcagagc gaggtatgta ggcggtgcta cagagttctt gaagtggtgg   4980

cctaactacg gctacactag aaggacagta tttggtatct gcgctctgct gaagccagtt   5040

accttcggaa aaagagttgg tagctcttga tccggcaaac aaaccaccgc tggtagcggt   5100

ggtttttttg tttgcaagca gcagattacg cgcagaaaaa aaggatctca agaagatcct   5160

ttgatctttt ctacggggtc tgacgctcag tggaacgaaa actcacgtta agggattttg   5220

gtcatgagat tatcaaaaag gatcttcacc tagatccttt taaattaaaa atgaagtttt   5280

aaatcaatct aaagtatata tgagtaaact tggtctgaca gttaccaatg cttaatcagt   5340

gaggcaccta tctcagcgat ctgtctattt cgttcatcca tagttgcctg actccccgtc   5400

gtgtagataa ctacgatacg ggagggctta ccatctggcc ccagtgctgc aatgataccg   5460

cgagacccac gctcaccggc tccagattta tcagcaataa accagccagc cggaagggcc   5520

gagcgcagaa gtggtcctgc aactttatcc gcctccatcc agtctattaa ttgttgccgg   5580

gaagctagag taagtagttc gccagttaat agtttgcgca acgttgttgc cattgctaca   5640

ggcatcgtgg tgtcacgctc gtcgtttggt atggcttcat tcagctccgg ttcccaacga   5700

tcaaggcgag ttacatgatc ccccatgttg tgcaaaaaag cggttagctc cttcggtcct   5760

ccgatcgttg tcagaagtaa gttggccgca gtgttatcac tcatggttat ggcagcactg   5820

cataattctc ttactgtcat gccatccgta agatgctttt ctgtgactgg tgagtactca   5880

accaagtcat tctgagaata gtgtatgcgg cgaccgagtt gctcttgccc ggcgtcaata   5940

cgggataata ccgcgccaca tagcagaact ttaaaagtgc tcatcattgg aaaacgttct   6000

tcggggcgaa aactctcaag gatcttaccg ctgttgagat ccagttcgat gtaacccact   6060

cgtgcaccca actgatcttc agcatctttt actttcacca gcgtttctgg gtgagcaaaa   6120

acaggaaggc aaaatgccgc aaaaaaggga ataagggcga cacggaaatg ttgaatactc   6180

atactcttcc tttttcaata ttattgaagc atttatcagg gttattgtct catgagcgga   6240

tacatatttg aatgtattta gaaaaataaa caaatagggg ttccgcgcac atttccccga   6300

aaagtgccac ctgacgcgcc ctgtagcggc gcattaagcg cggcgggtgt ggtggttacg   6360

cgcagcgtga ccgctacact tgccagcgcc ctagcgcccg ctcctttcgc tttcttccct   6420

tcctttctcg ccacgttcgc cggctttccc cgtcaagctc taaatcgggg gctcccttta   6480

gggttccgat ttagtgcttt acggcacctc gaccccaaaa aacttgatta gggtgatggt   6540

tcacgtagtg ggccatcgcc ctgatagacg gtttttcgcc ctttgacgtt ggagtccacg   6600

ttctttaata gtggactctt gttccaaact ggaacaacac tcaaccctat ctcggtctat   6660

tcttttgatt tataagggat tttgccgatt tcggcctatt ggttaaaaaa tgagctgatt   6720

taacaaaaat ttaacgcgaa ttttaacaaa atattaacgt ttacaatttc ccattcgcca   6780

ttcaggctgc gcaactgttg ggaagggcga tcggtgcggg cctcttcgct attacgccag   6840

cccaagctac catgataagt aagtaatatt aaggtacggg aggtacttgg agcggccgca   6900

ataaaatatc tttattttca ttacatctgt gtgttggttt tttgtgtgaa tcgatagtac   6960

taacatacgc tctccatcaa aacaaaacga aacaaaacaa actagcaaaa taggctgtcc   7020

ccagtgcaag tgcaggtgcc agaacatttc tctatcgata                         7060
```

<210> SEQ ID NO 14
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 14
atatccgcgg tagttattaa tagtaatc 28

<210> SEQ ID NO 15
<211> LENGTH: 39
<212> TYPE: DNA
<213> ORGANISM: Artificial
<220> FEATURE:
<223> OTHER INFORMATION: an artificially synthesized primer sequence

<400> SEQUENCE: 15
tggccgcggc cgctggatct gacggttcac taaaccagc 39

<210> SEQ ID NO 16
<211> LENGTH: 13
<212> TYPE: DNA
<213> ORGANISM: Artificial
<220> FEATURE:
<223> OTHER INFORMATION: an artificially synthesized primer sequence

<400> SEQUENCE: 16
ggccgcaagc ttg 13

<210> SEQ ID NO 17
<211> LENGTH: 13
<212> TYPE: DNA
<213> ORGANISM: Artificial
<220> FEATURE:
<223> OTHER INFORMATION: an artificially synthesized primer sequence

<400> SEQUENCE: 17
gatccaagct tgc 13

<210> SEQ ID NO 18
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 18
ttgccgcggc aattttaaaa gaaagggagg a 31

<210> SEQ ID NO 19
<211> LENGTH: 31
<212> TYPE: DNA
<213> ORGANISM: Artificial
<220> FEATURE:
<223> OTHER INFORMATION: an artificially synthesized primer sequence

<400> SEQUENCE: 19
gagccgcggc tctaaaattt aaaatttttt g 31

<210> SEQ ID NO 20
<211> LENGTH: 35
<212> TYPE: DNA
<213> ORGANISM: Artificial
<220> FEATURE:
<223> OTHER INFORMATION: an artificially synthesized primer sequence

<400> SEQUENCE: 20
taaggatcct taagttaatc aacctctgga ttaca 35

<210> SEQ ID NO 21
<211> LENGTH: 28
<212> TYPE: DNA

<213> ORGANISM: Artificial
<220> FEATURE:
<223> OTHER INFORMATION: an artificially synthesized primer sequence

<400> SEQUENCE: 21
cgcagatctg cggggaggcg gcccaaag 28

<210> SEQ ID NO 22
<211> LENGTH: 720
<212> TYPE: DNA
<213> ORGANISM: Artificial
<220> FEATURE:
<223> OTHER INFORMATION: an artificially synthesized nucleotide sequence

<400> SEQUENCE: 22
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 23
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 23
ccatggcggc cgccatggtg agcaagggcg agga 34

<210> SEQ ID NO 24
<211> LENGTH: 36
<212> TYPE: DNA
<213> ORGANISM: Artificial
<220> FEATURE:
<223> OTHER INFORMATION: an artificially synthesized primer sequence

<400> SEQUENCE: 24
agtagcggcc gctacttact tgtacagctc gtccat 36

<210> SEQ ID NO 25
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 25
aggatgcagg ccctggtgct actcct 26

<210> SEQ ID NO 26

<211> LENGTH: 27
<212> TYPE: DNA
<213> ORGANISM: Artificial
<220> FEATURE:
<223> OTHER INFORMATION: an artificially synthesized primer sequence

<400> SEQUENCE: 26
ttatattagg ggcccctggg gtccaga 27

<210> SEQ ID NO 27
<211> LENGTH: 11471
<212> TYPE: DNA
<213> ORGANISM: Artificial
<220> FEATURE:
<223> OTHER INFORMATION: an artificially synthesized vector sequence

<400> SEQUENCE: 27
gctcgagact agtgacttgg tgagtaggct tcgagcctag ttagaggact aggagaggcc 60
gtagccgtaa ctactctggg caagtagggc aggcggtggg tacgcaatgg gggcggctac 120
ctcagcacta aataggagac aattagacca atttgagaaa atacgacttc gcccgaacgg 180
aaagaaaaag taccaaatta aacatttaat atgggcaggc aaggagatgg agcgcttcgg 240
cctccatgag aggttgttgg agacagagga ggggtgtaaa agaatcatag aagtcctcta 300
ccccctagaa ccaacaggat cggagggctt aaaaagtctg ttcaatcttg tgtgcgtact 360
atattgcttg cacaaggaac agaaagtgaa agacacagag gaagcagtag caacagtaag 420
acaacactgc catctagtgg aaaaagaaaa aagtgcaaca gagacatcta gtggacaaaa 480
gaaaaatgac aagggaatag cagcgccacc tggtggcagt cagaattttc cagcgcaaca 540
acaaggaaat gcctgggtac atgtaccctt gtcaccgcgc accttaaatg cgtgggtaaa 600
agcagtagag gagaaaaaat ttggagcaga aatagtaccc atgtttcaag ccctatcaga 660
aggctgcaca ccctatgaca ttaatcagat gcttaatgtg ctaggagatc atcaaggggc 720
attacaaata gtgaaagaga tcattaatga agaagcagcc cagtgggatg taacacaccc 780
actacccgca ggacccctac cagcaggaca gctcagggac cctcgcggct cagatatagc 840
agggaccacc agctcagtac aagaacagtt agaatggatc tatactgcta acccccgggt 900
agatgtaggt gccatctacc ggagatggat tattctagga cttcaaaagt gtgtcaaaat 960
gtacaaccca gtatcagtcc tagacattag gcagggacct aaagagccct tcaaggatta 1020
tgtggacaga ttttacaagg caattagagc agaacaagcc tcaggggaag tgaaacaatg 1080
gatgacagaa tcattactca ttcaaaatgc taatccagat tgtaaggtca tcctgaaggg 1140
cctaggaatg caccccaccc ttgaagaaat gttaacggct tgtcaggggg taggaggccc 1200
aagctacaaa gcaaaagtaa tggcagaaat gatgcagacc atgcaaaatc aaaacatggt 1260
gcagcaggga ggtccaaaaa gacaaagacc cccactaaga tgttataatt gtggaaaatt 1320
tggccatatg caaagacaat gtccggaacc aaggaaaaca aaatgtctaa agtgtggaaa 1380
attgggacac ctagcaaaag actgcagggg acaggtgaat tttttagggt atggacggtg 1440
gatgggggca aaaccgagaa attttcccgc cgctactctt ggagcggaac cgagtgcgcc 1500
tccttcaccg agcggcacca ccccatacga cccagcaaag aagctcctgc agcaatatgc 1560
agagaaaggg aaacaactga gggagcaaaa gaggaatcca ccggcaatga atccggattg 1620
gaccgaggga tattctttga actccctctt tggagaagac caataaagac agtgtatata 1680
gaaggggtcc ccattaaggc actgctagac acaggggcag atgacaccat aattaaagaa 1740
aatgatttac aattatcagg tccatggaga cccaaaatta tagggggcat aggaggaggc 1800

-continued

```
cttaatgtaa aagaatataa cgacagggaa gtaaaaatag aagataaaat tttgagagga   1860
acaatattgt taggagcaac tcccattaat ataataggta gaaatttgct ggccccggca   1920
ggtgcccggt tagtaatggg acaattatca gaaaaaattc ctgtcacacc tgtcaaattg   1980
aaggaagggg ctcggggacc ctgtgtaaga caatggcctc tctctaaaga gaagattgaa   2040
gctttacagg aaatatgttc ccaattagag caggaaggaa aaatcagtag agtaggagga   2100
gaaaatgcat acaatacccc aatattttgc ataaagaaga aggacaaatc ccagtggagg   2160
atgctagtag actttagaga gttaaataag gcaacccaag atttctttga agtgcaatta   2220
gggatacccc acccagcagg attaagaaag atgagacaga taacagtttt agatgtagga   2280
gacgcctatt attccatacc attggatcca aattttagga aatatactgc ttttactatt   2340
cccacagtga ataatcaggg acccgggatt aggtatcaat tcaactgtct cccgcaaggg   2400
tggaaaggat ctcctacaat cttccaaaat acagcagcat ccattttgga ggagataaaa   2460
agaaacttgc cagcactaac cattgtacaa tacatggatg atttatgggt aggttctcaa   2520
gaaaatgaac acacccatga caaattagta gaacagttaa gaacaaaatt acaagcctgg   2580
ggcttagaaa ccccagaaaa gaaggtgcaa aaagaaccac cttatgagtg gatgggatac   2640
aaactttggc ctcacaaatg ggaactaagc agaatacaac tggaggaaaa agatgaatgg   2700
actgtcaatg acatccagaa gttagttggg aaactaaatt gggcagcaca attgtatcca   2760
ggtcttagga ccaagaatat atgcaagtta attagaggaa agaaaaatct gttagagcta   2820
gtgacttgga cacctgaggc agaagctgaa tatgcagaaa atgcagagat tcttaaaaca   2880
gaacaggaag gaacctatta caaaccagga atacctatta gggcagcagt acagaaattg   2940
gaaggaggac agtggagtta ccaattcaaa caagaaggac aagtcttgaa agtaggaaaa   3000
tacaccaagc aaaagaacac ccatacaaat gaacttcgca cattagctgg tttagtgcag   3060
aagatttgca aagaagctct agttatttgg gggatattac cagttctaga actcccgata   3120
gaaagagagg tatgggaaca atggtgggcg gattactggc aggtaagctg gattcccgaa   3180
tgggattttg tcagcacccc acctttgctc aaactatggt acacattaac aaaagaaccc   3240
atacccaagg aggacgttta ctatgtagat ggagcatgca acagaaattc aaaagaagga   3300
aaagcaggat acatctcaca atacggaaaa cagagagtag aaacattaga aaacactacc   3360
aatcagcaag cagaattaac agctataaaa atggctttgg aagacagtgg gcctaatgtg   3420
aacatagtaa cagactctca atatgcaatg ggaattttga cagcacaacc cacacaaagt   3480
gattcaccat tagtagagca aattatagcc ttaatgatac aaaagcaaca aatatatttg   3540
cagtgggtac cagcacataa aggaatagga ggaaatgagg agatagataa attagtgagt   3600
aaaggcatta gaagagtttt attcttagaa aaaatagaag aagctcaaga agagcatgaa   3660
agatatcata ataattggaa aaacctagca gatacatatg ggcttccaca aatagtagca   3720
aaagagatag tggccatgtg tccaaaatgt cagataaagg gagaaccagt gcatggacaa   3780
gtggatgcct cacctggaac atggcagatg gattgtactc atctagaagg aaaagtagtc   3840
atagttgcgg tccatgtagc cagtggattc atagaagcag aagtcatacc tagggaaaca   3900
ggaaaagaaa cggcaaagtt tctattaaaa atactgagta gatggcctat aacacagtta   3960
cacacagaca atgggcctaa ctttacctcc caagaagtgg cagcaatatg ttggtgggga   4020
aaaattgaac atacaacagg tataccatat aacccccaat ctcaaggatc aatagaaagc   4080
atgaacaaac aattaaaaga gataattggg aaaataagag atgattgcca atatacagag   4140
acagcagtac tgatggcttg ccatattcac aattttaaaa gaaagggagg aatagggga    4200
```

-continued

```
cagacttcag cagagagact aattaatata ataacaacac aattagaaat acaacattta   4260
caaaccaaaa ttcaaaaaat tttaaatttt agagtctact acagagaagg gagagaccct   4320
gtgtggaaag gaccagcaca attaatctgg aaaggggaag gagcagtggt cctcaaggac   4380
ggaagtgacc taaaggttgt accaagaagg aaagctaaaa ttattaagga ttatgaaccc   4440
aaacaaagag tgggtaatga gggtgacgtg gaaggtacca ggggatctga taactaaatg   4500
gcagggaata gtcagatatt ggatgagaca aagaaatttg aaatggaact attatatgca   4560
ttaccaaatt acatgggctt ggtacaccat gagtagatat gtaataccaa taggaaaaca   4620
tggggaaata tgtgtagacc tatattggca tttaacacca gagcaaggat ggctatccac   4680
atatgcagta ggtatacaat atgtaagcaa tttagaatct aaatatagaa cagaattaga   4740
ccctgctaca gcagatagta taatacatgg tcactatttt aattgtttta aagaaagagc   4800
catccaacaa gctctgaggg gccacagatt tgtcttctgt cagtttccag aagggcataa   4860
aagcacagga caggtaccat ctttgcagta cctagctctg ctcgcacatc aaaatggcct   4920
cagggagaga tccaagagag gcaagaccag gagaagtaga aatttgggat ctaagcaggg   4980
agccgtggga cgaatggcta agagatatgt tacaagatct caaccaggag gcgaggctgc   5040
attttgggag agaactcctg ttccaagtat ggaactactg tcaggaggaa ggagaaagac   5100
atggtactcc catgatggaa agggcctaca aatattatag gctagtacaa aaggctctct   5160
ttgtgcattt tcgatgtggg tgcaggagaa ggcagccctt tgaaccatac gaggagagga   5220
gagatggaca agggggaggc agagcaaatc gtgtcccacc aggacttgag tgaagactat   5280
cagaagcctc tgcagacttg taaaaataaa tgtttttgca aaaaatgttg ttaccactgt   5340
cagctttgct ttctgcaaaa aggcctaggt gttacctatc atgcccctag gaccagaaga   5400
aagaagattg cttcgcttga tttggctcct ttacagcacc agtaagtaga attcttttat   5460
tgtaagatgg attggttttt aaattactta aataataaaa catgggatgc agaccataat   5520
ttttgtagca gcaaaaagaa aggacacgca ccaggaccat gtgtacaaag gacgtatgtt   5580
gcttgccata tcaggtctgt aataaatgat tggtataccc tatcaaagaa aacttatgct   5640
ccgccaagag aaggacattt gcaatgcagg tccacagtca ctgggatgac agttgagctt   5700
aattataata gtaaaaacag aaccaacgtg acactaagtc cccagataga atctatctgg   5760
gcggctgaat tgggcagata caaattagtg gaaatcacac caattggctt tgcacccaca   5820
gaagtaaggc gttatacggg aggacatgag aggcaaaaga gagtcccgtt tgtgctaggg   5880
ttcttaggct tcttgggggc tgctggaact gcaatggaag cagcggcgac agccctgacg   5940
gtccagtctc agcatttgct tgctgggata ctgcagcagc agaagaatct gctggcggct   6000
gtggaggctc aacagcagat gttgaagctg accatttggg gtgttaaaaa cctcaatgcc   6060
cgcgtcacag cccttgagaa gtacctagag gatcaggcac gactaaactc ctgggggtgc   6120
gcatggaaac aagtatgtca taccacagtg gagtggccct ggacaaatcg gactccggat   6180
tggcaaaata tgacttggtt ggagtgggaa agacaaatag ctgatttgga aagcaacatt   6240
acgagacaat tagtgaaggc tagagaacaa gaggaaaaga atctagatgc ctatcagaag   6300
ttaactagtt ggtcagattt ctggtcttgg ttcgatttct caaaatggct taacatttta   6360
aaaatgggat ttttagtaat agtaggaata atagggttaa gattacttta cacagtatat   6420
ggatgtatag tgagggttag gcagggatat gttcctctat ctccacagat ccatatccac   6480
caagtgggga agggacggcc agacaacgcc gacgagccag gagaaggtgg agacaacagc   6540
aggatcaaat tagagtcttg gtagaaagac tccaagagca ggtgtatgca gttgaccgcc   6600
```

-continued

```
tggctgacga ggctcaacac ttggctatac aacagttgcc tgaccctcct cattcagctt   6660
agctagcggc cgcaattcac tcctcaggtg caggctgcct atcagaaggt ggtggctggt   6720
gtggccaatg ccctggctca caaataccac tgagatcttt ttccctctgc caaaaattat   6780
ggggacatca tgaagcccct tgagcatctg acttctggct aataaaggaa atttattttc   6840
attgcaatag tgtgttggaa tttttttgtgt ctctcactcg gaaggacata tgggagggca   6900
aatcatttaa aacatcagaa tgagtatttg gtttagagtt tggcaacata tgcccatatg   6960
ctggctgcca tgaacaaagg ttggctataa agaggtcatc agtatatgaa acagcccct    7020
gctgtccatt ccttattcca tagaaaagcc ttgacttgag gttagatttt ttttatattt   7080
tgttttgtgt tattttttc tttaacatcc ctaaaatttt ccttacatgt tttactagcc    7140
agatttttcc tcctctcctg actactccca gtcatagctg tccctcttct cttatggaga   7200
tccctcgacc tgcagcccaa gcttggcgta atcatggtca tagctgtttc ctgtgtgaaa   7260
ttgttatccg ctcacaattc cacacaacat acgagccgga agcataaagt gtaaagcctg   7320
gggtgcctaa tgagtgagct aactcacatt aattgcgttg cgctcactgc ccgctttcca   7380
gtcgggaaac ctgtcgtgcc agcggatccg catctcaatt agtcagcaac catagtcccg   7440
cccctaactc cgcccatccc gcccctaact ccgcccagtt ccgcccattc tccgccccat   7500
ggctgactaa ttttttttat ttatgcagag gccgaggccg cctcggcctc tgagctattc   7560
cagaagtagt gaggaggctt ttttggaggc ctaggctttt gcaaaaagct aacttgttta   7620
ttgcagctta taatggttac aaataaagca atagcatcac aaatttcaca aataaagcat   7680
ttttttcact gcattctagt tgtggtttgt ccaaactcat caatgtatct tatcatgtct   7740
ggatccgctg cattaatgaa tcggccaacg cgcggggaga ggcggtttgc gtattgggcg   7800
ctcttccgct tcctcgctca ctgactcgct gcgctcggtc gttcggctgc ggcgagcggt   7860
atcagctcac tcaaaggcgg taatacggtt atccacagaa tcaggggata acgcaggaaa   7920
gaacatgtga gcaaaaggcc agcaaaaggc caggaaccgt aaaaaggccg cgttgctggc   7980
gtttttccat aggctccgcc cccctgacga gcatcacaaa aatcgacgct caagtcagag   8040
gtggcgaaac ccgacaggac tataaagata ccaggcgttt ccccctggaa gctccctcgt   8100
gcgctctcct gttccgaccc tgccgcttac cggatacctg tccgcctttc tcccttcggg   8160
aagcgtggcg ctttctcata gctcacgctg taggtatctc agttcggtgt aggtcgttcg   8220
ctccaagctg ggctgtgtgc acgaaccccc cgttcagccc gaccgctgcg ccttatccgg   8280
taactatcgt cttgagtcca acccggtaag acacgactta tcgccactgg cagcagccac   8340
tggtaacagg attagcagag cgaggtatgt aggcggtgct acagagttct tgaagtggtg   8400
gcctaactac ggctacacta gaagaacagt atttggtatc tgcgctctgc tgaagccagt   8460
taccttcgga aaaagagttg gtagctcttg atccggcaaa caaaccaccg ctggtagcgg   8520
tggttttttt gtttgcaagc agcagattac gcgcagaaaa aaaggatctc aagaagatcc   8580
tttgatcttt tctacggggt ctgacgctca gtggaacgaa aactcacgtt aagggatttt   8640
ggtcatgaga ttatcaaaaa ggatcttcac ctagatcctt ttaaattaaa aatgaagttt   8700
taaatcaatc taaagtatat atgagtaaac ttggtctgac agttaccaat gcttaatcag   8760
tgaggcacct atctcagcga tctgtctatt tcgttcatcc atagttgcct gactccccgt   8820
cgtgtagata actacgatac gggagggctt accatctggc cccagtgctg caatgatacc   8880
gcgagaccca cgctcaccgg ctccagattt atcagcaata aaccagccag ccggaagggc   8940
cgagcgcaga agtggtcctg caactttatc cgcctccatc cagtctatta attgttgccg   9000
```

-continued

```
ggaagctaga gtaagtagtt cgccagttaa tagtttgcgc aacgttgttg ccattgctac   9060
aggcatcgtg gtgtcacgct cgtcgtttgg tatggcttca ttcagctccg gttcccaacg   9120
atcaaggcga gttacatgat cccccatgtt gtgcaaaaaa gcggttagct ccttcggtcc   9180
tccgatcgtt gtcagaagta agttggccgc agtgttatca ctcatggtta tggcagcact   9240
gcataattct cttactgtca tgccatccgt aagatgcttt tctgtgactg gtgagtactc   9300
aaccaagtca ttctgagaat agtgtatgcg gcgaccgagt tgctcttgcc cggcgtcaat   9360
acgggataat accgcgccac atagcagaac tttaaaagtg ctcatcattg gaaaacgttc   9420
ttcggggcga aaactctcaa ggatcttacc gctgttgaga tccagttcga tgtaacccac   9480
tcgtgcaccc aactgatctt cagcatcttt tactttcacc agcgtttctg ggtgagcaaa   9540
aacaggaagg caaaatgccg caaaaaaggg aataagggcg acacggaaat gttgaatact   9600
catactcttc ctttttcaat attattgaag catttatcag ggttattgtc tcatgagcgg   9660
atacatattt gaatgtattt agaaaaataa acaaataggg gttccgcgca catttccccg   9720
aaaagtgcca cctgggtcga tcgacattga ttattgacta gttattaata gtaatcaatt   9780
acggggtcat tagttcatag cccatatatg gagttccgcg ttacataact tacggtaaat   9840
ggcccgcctg gctgaccgcc caacgacccc cgcccattga cgtcaataat gacgtatgtt   9900
cccatagtaa cgccaatagg gactttccat tgacgtcaat gggtggagta tttacggtaa   9960
actgcccact tggcagtaca tcaagtgtat catatgccaa gtacgccccc tattgacgtc  10020
aatgacggta aatggcccgc ctggcattat gcccagtaca tgaccttatg ggactttcct  10080
acttggcagt acatctacgt attagtcatc gctattacca tggtcgaggt gagccccacg  10140
ttctgcttca ctctccccat ctcccccccc tccccacccc caattttgta tttatttatt  10200
ttttaattat tttgtgcagc gatgggggcg gggggggggg gggggcgcgc gccaggcggg  10260
gcggggcggg gcgaggggcg gggcggggcg aggcggagag gtgcggcggc agccaatcag  10320
agcggcgcgc tccgaaagtt tccttttatg gcgaggcggc ggcggcggcg gccctataaa  10380
aagcgaagcg cgcggcgggc gggagtcgct gcgcgctgcc ttcgccccgt gccccgctcc  10440
gccgccgcct cgcgccgccc gccccggctc tgactgaccg cgttactccc acaggtgagc  10500
gggcgggacg gcccttctcc tccgggctgt aattagcgct tggtttaatg acggcttgtt  10560
tcttttctgt ggctgcgtga aagccttgag gggctccggg agggcccttt gtgcgggggg  10620
agcggctcgg ggggtgcgtg cgtgtgtgtg tgcgtgggga gcgccgcgtg cggctccgcg  10680
ctgcccggcg gctgtgagcg ctgcgggcgc ggcgcggggc tttgtgcgct ccgcagtgtg  10740
cgcgagggga gcgcggccgg gggcggtgcc ccgcggtgcg gggggggctg cgaggggaac  10800
aaaggctgcg tgcggggtgt gtgcgtgggg gggtgagcag ggggtgtggg cgcgtcggtc  10860
gggctgcaac cccccctgca cccccctccc cgagttgctg agcacggccc ggcttcgggt  10920
gcggggctcc gtacggggcg tggcgcgggg ctcgccgtgc cgggcggggg gtggcggcag  10980
gtgggggtgc cgggcggggc ggggccgcct cgggccgggg agggctcggg ggaggggcgc  11040
ggcggccccc ggagcgccgg cggctgtcga ggcgcggcga gccgcagcca ttgcctttta  11100
tggtaatcgt gcgagagggc gcagggactt cctttgtccc aaatctgtgc ggagccgaaa  11160
tctgggaggc gccgccgcac cccctctagc gggcgcgggg cgaagcggtg cggcgccggc  11220
aggaaggaaa tgggcgggga gggccttcgt gcgtcgccgc gccgccgtcc ccttctccct  11280
ctccagcctc ggggctgtcc gcggggggac ggctgccttc ggggggacg gggcagggcg  11340
gggttcggct tctggcgtgt gaccggcggc tctagagcct ctgctaacca tgttcatgcc  11400
```

ttcttctttt tcctacagct cctgggcaac gtgctggtta ttgtgctgtc tcatcatttt 11460
ggcaaagaat t 11471

<210> SEQ ID NO 28
<211> LENGTH: 9
<212> TYPE: DNA
<213> ORGANISM: Artificial
<220> FEATURE:
<223> OTHER INFORMATION: an artificially synthesized primer sequence

<400> SEQUENCE: 28 tcagctggc 9

<210> SEQ ID NO 29
<211> LENGTH: 17
<212> TYPE: DNA
<213> ORGANISM: Artificial
<220> FEATURE:
<223> OTHER INFORMATION: an artificially synthesized primer sequence

<400> SEQUENCE: 29
ggccgccagc tgatgca 17

<210> SEQ ID NO 30
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 30
cccgtttgtg ctagggttct tagg 24

<210> SEQ ID NO 31
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 31
ggatatggat ctgtggagat agag 24

<210> SEQ ID NO 32
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 32
atgcccctag gaccagaaga aag 23

<210> SEQ ID NO 33
<211> LENGTH: 37
<212> TYPE: DNA
<213> ORGANISM: Artificial
<220> FEATURE:
<223> OTHER INFORMATION: an artificially synthesized primer sequence

<400> SEQUENCE: 33
acttggtgga tatggattgg tgctgtaaag gagccaa 37

<210> SEQ ID NO 34
<211> LENGTH: 37
<212> TYPE: DNA

-continued

```
<213> ORGANISM: Artificial
<220> FEATURE:
<223> OTHER INFORMATION: an artificially synthesized primer sequence

<400> SEQUENCE: 34

ttggctcctt tacagcacca atccatatcc accaagt                               37


<210> SEQ ID NO 35
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 35

ctaagctgaa tgaggagggt cag                                              23
```